United States Patent
Sakamoto et al.

(10) Patent No.: US 9,371,389 B2
(45) Date of Patent: Jun. 21, 2016

(54) ANTI-HUMAN XCR1 ANTIBODIES

(75) Inventors: Yoshimasa Sakamoto, Kobe (JP); Miyuki Nishimura, Kobe (JP); Tetsu Kawano, Kobe (JP); Yukihisa Sawa, Kobe (JP); Toshio Imai, Kobe (JP)

(73) Assignee: Eisai R&D Management Co., Ltd., Tokyo (JP)

(*) Notice: Subject to any disclaimer, the term of this patent is extended or adjusted under 35 U.S.C. 154(b) by 0 days.

(21) Appl. No.: 14/240,090

(22) PCT Filed: Aug. 30, 2012

(86) PCT No.: PCT/JP2012/072667
§ 371 (c)(1),
(2), (4) Date: Feb. 21, 2014

(87) PCT Pub. No.: WO2013/032032
PCT Pub. Date: Mar. 7, 2013

(65) Prior Publication Data
US 2014/0193421 A1 Jul. 10, 2014

Related U.S. Application Data

(60) Provisional application No. 61/530,194, filed on Sep. 1, 2011, provisional application No. 61/659,637, filed on Jun. 14, 2012.

(51) Int. Cl.
| | | |
|---|---|---|
| C07K 16/00 | (2006.01) | |
| C12P 21/08 | (2006.01) | |
| C07K 16/28 | (2006.01) | |
| A61K 39/00 | (2006.01) | |

(52) U.S. Cl.
CPC ....... *C07K 16/2866* (2013.01); *A61K 2039/505* (2013.01); *C07K 2317/24* (2013.01); *C07K 2317/34* (2013.01); *C07K 2317/55* (2013.01); *C07K 2317/76* (2013.01); *C07K 2319/55* (2013.01)

(58) Field of Classification Search
None
See application file for complete search history.

(56) References Cited

U.S. PATENT DOCUMENTS

| | | | |
|---|---|---|---|
| 4,816,567 | A | 3/1989 | Cabilly et al. |
| 5,786,210 | A | 7/1998 | Kelner et al. |
| 5,877,285 | A | 3/1999 | Kelner et al. |
| 5,985,580 | A | 11/1999 | Kelner et al. |
| 6,245,329 | B1 | 6/2001 | Kelner et al. |
| 2003/0186889 | A1* | 10/2003 | Forssmann et al. ............. 514/14 |
| 2004/0033209 | A1 | 2/2004 | Mack et al. |
| 2010/0303808 | A1 | 12/2010 | Williams |

FOREIGN PATENT DOCUMENTS

| | | |
|---|---|---|
| EP | 2149582 | 2/2010 |
| WO | 02/59608 | 8/2002 |
| WO | 2009/065561 | 5/2009 |

OTHER PUBLICATIONS

Gavilondo, Biotech. 2000, vol. 29: 128-145.*
Dryberg et al., 1986: J. Exp. Med. vol. 164: 1344-1349.*
Kringelum et al., 2013, Mol. Immunol. vol. 53: 24-34.*
Office Action issued in NZ Application No. 621320 dated Dec. 9, 2014, 2 pages.
EP Communication from European application No. 12761822.1-1412, Apr. 8, 2014.
Response to EP Communication from European application No. 12761822.1-1412, Oct. 14, 2014.
Response to Office Action filed in NZ Application No. 621320 dated Jun. 16, 2015, 21 pages.
Office Action issued in corresponding New Zealand Application No. 621320 dated Jul. 2, 2015, 2 pages.
Office Action issued in CN Application No. 201280041366.2, dated Jul. 27, 2015, 13 pages, with English translation.
Office Action issued in EP Application Ser. No. 12761822.1, dated Aug. 6, 2015, 6 pages.
Khurram et al., "Functional expression of the chemokine receptor XCR1 on oral epithelial cells", Journal of Pathology, 2010, vol. 221, pp. 153-163.
"XCRI Goat anti-Human Polyclonal (N-Terminus) (PE) Antibody", Catalog ID: LS-C76885, LifeSpan BioSciences, Inc., 2013, 1 page.
"Polyclonal Anti-human XCR1-Phycoerythrin", Catalog No: FAB857P, R&D Systems, Inc., 2012, 2 pages.
Yoshida et al., "Identification of Single C Motif-1/Lymphotactin Receptor XCR1," The Journal of Biological Chemistry, 1998, vol. 273, No. 26, pp. 16551-16554.
Crozat et al., "The XC chemokine receptor 1 is a conserved selective marker of mammalian cells homolgous to mouse $CD8\alpha^+$ dendritic cells", The Journal of Experimental Medicine, 2010, vol. 207, No. 6, pp. 1283-1292.
Dorner et al., "Selective Expression of the Chemokine Receptor XCR1 on Cross-presenting Dendritic Cells Determines Cooperation with $CD8^+$ T Cells", Immunity, 2009, vol. 31, pp. 823-833.
Bachem et al., "Superior antigen cross-presentation and XCR1 expression define human $CD11c^+CD141^+$ cells as homologues of mouse $CD8^+$ dendritic cells", The Journal of Experimental Medicine, 2010, vol. 207, No. 6, pp. 1273-1281.

(Continued)

*Primary Examiner* — Amy Juedes
(74) *Attorney, Agent, or Firm* — Fish & Richardson P.C.

(57) ABSTRACT

An object of the present invention is to provide a monoclonal antibody binding to human XCR1, wherein the antibody binds to linear or discontinuous epitopes which comprise at least three amino acids selected from the group consisting of the 8th, 11th, 12th, 13th, 14th, 16th, 17th, 22nd, 23rd, 176th, and 177th amino acids in the amino acid sequence of SEQ ID NO: 91.

21 Claims, 26 Drawing Sheets

(56) References Cited

OTHER PUBLICATIONS

Kurts et al., "Cross-priming in health and disease", Nature Reviews Immunology, 2010, vol. 10, pp. 403-414.
Cravens and Lipsky, "Dendritic cells, chemokine receptors and autoimmune inflammatory diseases", Immunology and Cell Biology, 2002, vol. 80, pp. 497-505.
Waldner, H., "The role of innate immune responses in autoimmune disease development," Autoimmunity Reviews, 2009, vol. 8, pp. 400-404.
Köhler and Milstein, "Continuous cultures of fused cells secreting antibody of predefined specificity", Nature, 1975, vol. 256, pp. 495-497.
Clackson et al., "Making antibody fragments using phage display libraries", Nature, 1991, vol. 352, pp. 624-628.
Marks et al., "By-passing Immunization Human Antibodies from V-gene Libraries Displayed on Phage", Journal of Molecular Biology, 1991, vol. 222, pp. 581-597.
Karlin and Altschul, "Methods for assessing the statistical significance of molecular sequence features by using general scoring schemes", Proceedings of the National Academy of Sciences USA, 1990, vol. 87, pp. 2264-2268.
Karlin and Altschul, "Applications and statistics for multiple high-scoring segments in molecular Sequences", Proceedings of the National Academy of Sciences USA, 1993, vol. 90, pp. 5873-5877.
Altschul et al., "Basic Local Alignment Search Tool", Journal of Molecular Biology, 1990, vol. 215, pp. 403-410.
Lazar et al., "Engineered antibody Fc variants with enhanced effector function", Proceedings of the National Academy of Sciences USA, 2006, vol. 103, No. 11, pp. 4005-4010.
Shields et al., "High Resolution Mapping of the Binding Site . . . with Improved Binding to the FcγR" The Journal of Biological Chemistry, 2001, vol. 276, No. 9, pp. 6591-6604.
Moore et al., "Engineered FC variant antibodies with enhanced ability to recruit complement and mediate effector functions", mAbs, 2010, vol. 2, No. 2, pp. 181-189.
Cole et al., "Human IgG2 Variants of Chimeric Anti-CD3 Are Nonmitogenic to T Cells", The Journal of Immunology, 1997, vol. 159, pp. 3613-3621.
An et al., "IgG2m4, an engineered antibody isotype with reduced Fc function", mAbs, 2009, vol. 1, No. 6, pp. 572-579.
Wu and Kabat, "An Analysis of the Sequences of the Variable Regions . . . Their Implications for Anti-Body Complementarity," The Journal of Experimental Medicine, 1970, vol. 132, pp. 211-250.
Kehren et al., "Cytotoxicity Is Mandatory for CD8+ T Cell-mediated Contact Hypersensitivity", The Journal of Experimental Medicine, 1999, vol. 189, No. 5, pp. 779-786.
Middel et al., "Expression of the T-Cell Chemoattractant Chemokine Lymphotactin in Crohn's Disease", American Journal of Pathology, 2001, vol. 159, No. 5, pp. 1751-1761.
Sugihara et al., "A New Murine Model to Define the Critical Pathologic and Therapeutic Mediators of Polymyositis," Arthritis & Rheumatism, 2007, vol. 56, No. 4, pp. 1304-1314.
Wang et al., "Up-regulation of XCR1 expression in rheumatoid joints," Rheumatology, 2004, vol. 43: pp. 569-573.
Muroi et al., "Elevation of Serum Lymphotactin Levels in Patients with Systemic Sclerosis," The Journal of Rheumatology, 2008, vol. 35, No. 5, pp. 834-838.
Torrence et al., "Serum Biomarkers in a Mouse Model of Bacterial-Induced Inflammatory Bowel Disease," Inflammatory Bowel Diseases, 2008, vol. 14, No. 4, pp. 480-490.
Yeh et al., "Expressions of lymphotactin and its receptor, SCR, in Lewis rats with experimental autoimmune anterior uveitis," Graefe's Archive for Clinical and Experimental Ophthalmology, 2010, vol. 248, pp. 1737-1747.
Blaschke et al., "Expression and Function of the C-Class Chemokine Lymphotactin (XCL1) in Wegener's Granulomatosis", The Journal of Rheumatology, 2009, vol. 36, No. 11, pp. 2491-2500.
Yasuoka et al., "Autoreactive CD8+ Cytotoxic T Lymphocytes to Major Histocompatibility . . . in Patients with Behcet's Disease," Arthritis & Rheumatism, 2004, vol. 50, No. 11, pp. 3658-3662.
Serody et al., "T-lymphocyte production of macrophage inflammatory protein-1α is critical . . . during graft-versus-host disease," Blood, 2000, vol. 96, No. 9, pp. 2973-2980.
Dalakas, M.C., "Review: An update on inflammatory and autoimmune myopathies", Neuropathology and Applied Neurobiology, 2011, vol. 37, pp. 226-242.
Fabrizi et al., "Heterogeneity of atopic dermatitis defined by the immune response to inhalant and food allergens", European Journal of Dermatology, 1999, vol. 9, pp. 380-384.
Fonacier et al., "Allergic skin diseases", Journal of Allergy and Clinical Immunology, 2010, vol. 125, No. 2, pp. S138-S149.
Mody et al., "CD8 Cells Play a Critical role in Delayed Type Hypersensitivity to Intact *Cryptococcus neoformans*[1]", Journal of Immunology, 1994, vol. 152, pp. 3970-3979.
Gudjonsson et al , "Immunopathogenic mechanisms in psoriasis", Clinical and Experimental Immunology, 2004, vol. 135, pp. 1-8.
Friese and Fugger, "Autoreactive CD8+ T cells in multiple sclerosis: a new target for therapy", Brain, 2005, vol. 128, pp. 1747-1763.
Wang et al., "The role of CD8+ T cells in the initiation of insulin-dependent diabetes mellitus," European Journal of Immunology, 1996, vol. 26, pp. 1762-1769.
Heymann et al., "Kidney dendritic cells activation is required for progression of renal disease in a mouse model of glomerular injury", The Journal of Clinical Investigation, 2009, vol. 119, No. 5, pp. 1286-1297.
Couzi et al., "Predominance of CD8+ T Lymphocytes Among Periglomerular Infiltrating Cells and Link to the Prognosis of Class III and Class IV Lupus Nephritis", Arthritis & Rheumatism, 2007, vol. 56, No. 7, pp. 2362-2370.
Kammer et al., "Molecular Mimicry of Human Cytochrome P450 by Hepatitis C Virus at the Level of Cytotoxic T Cell Recognition", The Journal of Experimental Medicine, 1999, vol. 190, No. 2, pp. 169-176.
Brazillet et al., "Induction of experimental autoimmune thyroiditis by heat-denatured porcine thyroglobulin: a Tc1-mediated disease", European Journal of Immunology, 1999, vol. 29, pp. 1342-1352.
Bueno and Pestana, "The role of CD8+ T cells during allograft rejection", Brazilian Journal of Medical and Biological Research, 2002, vol. 35, pp. 1247-1258.
Hohlfeld and Engel, "Coculture with Autologous Myotubes of Cytotoxic T Cells Isolated from Muscle in Inflammatory Myopathies", Annals of Neurology, 1991, vol. 29, pp. 498-507.
Yamazaki et al., "Conservation of a chemokine system, SCR1 and its ligand, SCL1, between human and mice," Biochemical and Biophysical Research Communications, 2010, vol. 397, No. 4, pp. 756-761.
Jongbloed et al., "Human CD141+ (BDCA-3)+ dendritic cells (CDs) represent a unique myeloid DC subset that cross-presents necrotic cell antigens", The Journal of Experimental Medicine, 2010, vol. 207, No. 6, pp. 1247-1260.
Poulin et al., "Characterization of human DNGR-1+ BDCA3+ leukocytes as putative equivalents of mouse CD8α+ dendritic cells," The Journal of Experimental Medicine, 2010, vol. 207, No. 6, pp. 1261-1271.
Bachem et al., "Expression of XCR1 characterizes the Batf3-dependent lineage of dendritic cells capable of antigen cross-presentation", Frontiers in Immunology, 2012, vol. 3, Article 214, pp. 1-12.
Lei and Takahama, "XCL1 and XCR1 in the immune system", Microbes and Infection, 2012, vol. 14, No. 3, pp. 262-267.
European Patent Office, International Search Report for PCT/JP2012/072667 dated Dec. 6, 2012.
European Patent Office, Written Opinion for PCT/JP2012/072667 dated Dec. 6, 2012.
Response to Office Action in New Zealand Application Ser. No. 621320, dated Oct. 2, 2015.
Notice of Acceptance issued in New Zealand Application Ser. No. 621320, dated Nov. 12, 2015.

(56) References Cited

OTHER PUBLICATIONS

Response to Office Action filed in CN Application No. 201280041366.2, dated Dec. 4, 2015, 20 pages, with English Translation.

Response to Office Action filed in EP Application No. 12761822.1, dated Dec. 4, 2015, 15 pages.

Office Action issued in Chinese Application No. 201280041366.2, dated Mar. 25, 2016, 6 pages (with English translation).

Office Action in Taiwan Application No. 101131633, dated Apr. 15, 2016, 7 pages (with English Translation).

Office Action issued in Japanese Application No. 2014-509528, dated Apr. 26, 2016, 5 pages (with English translation).

* cited by examiner

<VH CDRs>
CDR1
5G7 :SHNLH(SEQ ID No: 17)
2H6 :SHNMH(SEQ ID No: 29)
11H2:DYYVN(SEQ ID No: 41)
     SHNXH(Seq ID No: 53)
CDR2
5G7 :AIYPGNGNTAYNQKFKG(SEQ ID No: 18)
2H6 :AIYPGKGNTSYNQKFKG(SEQ ID No: 30)
11H2:VSNPKNGDKSYNQKFKG(SEQ ID No: 42)
     AIYPGXGNTXYNQKFKG(Seq ID No: 54)
CDR3
5G7 :WGSVVGDW•YFDV(SEQ ID No: 19)
2H6 :WGSVVGDW•YFDV(SEQ ID No: 31)
11H2:GLYYAGTYGYFDV(SEQ ID No: 43)
     WGSVVGDW•YFDV(SEQ ID No: 55)

<VL CDRs>
CDR1
2H6 :RSSQSLVHSNGNTYLH(SEQ ID No: 20)
5G7 :RSSLGLVHRNGNTYLH(SEQ ID No: 32)
11H2:RASQDISNYLN      (SEQ ID No: 44)
     RSSXXLVHXNGNTYLH(SEQ ID No: 56)
CDR2
5G7 :KVSHRFS(SEQ ID No: 21)
2H6 :RVSNRFS(SEQ ID No: 33)
11H2:YTSRLHS(SEQ ID No: 45)
     XVSXRFS(SEQ ID No: 57)
CDR3
5G7 :SQSTHVPWT(SEQ ID No: 22)
2H6 :SQSTFVPWT(SEQ ID No: 34)
11H2:QQGKTLPRT(SEQ ID No: 46)
     SQSTXVPWT(SEQ ID No: 58)

```
<211>   333
<212>   PRT
<213>   Abramis brama
```

| | | | | | | | | | | | | | | |
|---|---|---|---|---|---|---|---|---|---|---|---|---|---|---|
| Met | Glu | Ser | Ser | Gly | Asn | Pro | Glu | Ser | Thr | Thr | Phe | Phe | Tyr | Tyr | Asp |
| 1 | | | | 5 | | | | | 10 | | | | | 15 | |
| Leu | Gln | Ser | Gln | Pro | Cys | Glu | Asn | Gln | Ala | Trp | Val | Phe | Ala | Thr | Leu |
| | | | 20 | | | | | 25 | | | | | 30 | | |
| Ala | Thr | Thr | Val | Leu | Tyr | Cys | Leu | Val | Phe | Leu | Leu | Ser | Leu | Val | Gly |
| | | 35 | | | | | 40 | | | | | 45 | | | |
| Asn | Ser | Leu | Val | Leu | Trp | Val | Leu | Val | Lys | Tyr | Glu | Ser | Leu | Glu | Ser |
| | 50 | | | | | 55 | | | | | 60 | | | | |
| Leu | Thr | Asn | Ile | Phe | Ile | Leu | Asn | Leu | Cys | Leu | Ser | Asp | Leu | Val | Phe |
| 65 | | | | | 70 | | | | | 75 | | | | | 80 |
| Ala | Cys | Leu | Leu | Pro | Val | Trp | Ile | Ser | Pro | Tyr | His | Trp | Gly | Trp | Val |
| | | | | 85 | | | | | 90 | | | | | 95 | |
| Leu | Gly | Asp | Phe | Leu | Cys | Lys | Leu | Leu | Asn | Met | Ile | Phe | Ser | Ile | Ser |
| | | | | 100 | | | | | 105 | | | | | 110 | |
| Leu | Tyr | Ser | Ser | Ile | Phe | Phe | Leu | Thr | Ile | Met | Thr | Ile | His | Arg | Tyr |
| | | | 115 | | | | | 120 | | | | | 125 | | |
| Leu | Ser | Val | Val | Ser | Pro | Leu | Ser | Thr | Leu | Arg | Val | Pro | Thr | Leu | Arg |
| | | 130 | | | | | 135 | | | | | 140 | | | |
| Cys | Arg | Val | Leu | Val | Thr | Met | Ala | Val | Trp | Val | Ala | Ser | Ile | Leu | Ser |
| 145 | | | | | 150 | | | | | 155 | | | | | 160 |
| Ser | Ile | Leu | Asp | Thr | Ile | Phe | His | Lys | Val | Leu | Ser | Ser | Gly | Cys | Asp |
| | | | | 165 | | | | | 170 | | | | | 175 | |
| Tyr | Ser | Glu | Leu | Thr | Trp | Tyr | Leu | Thr | Ser | Val | Tyr | Gln | His | Asn | Leu |
| | | | 180 | | | | | 185 | | | | | 190 | | |
| Phe | Phe | Leu | Leu | Ser | Leu | Gly | Ile | Ile | Leu | Phe | Cys | Tyr | Val | Glu | Ile |
| | | | 195 | | | | | 200 | | | | | 205 | | |
| Leu | Arg | Thr | Leu | Phe | Arg | Ser | Arg | Ser | Lys | Arg | Arg | His | Arg | Thr | Val |
| | | 210 | | | | | 215 | | | | | 220 | | | |
| Lys | Leu | Ile | Phe | Ala | Ile | Val | Val | Ala | Tyr | Phe | Leu | Ser | Trp | Gly | Pro |
| 225 | | | | | 230 | | | | | 235 | | | | | 240 |
| Tyr | Asn | Phe | Thr | Leu | Phe | Leu | Gln | Thr | Leu | Phe | Arg | Thr | Gln | Ile | Ile |
| | | | | 245 | | | | | 250 | | | | | 255 | |
| Arg | Ser | Cys | Glu | Ala | Lys | Gln | Gln | Leu | Glu | Tyr | Ala | Leu | Leu | Ile | Cys |
| | | | 260 | | | | | 265 | | | | | 270 | | |
| Arg | Asn | Leu | Ala | Phe | Ser | His | Cys | Cys | Phe | Asn | Pro | Val | Leu | Tyr | Val |
| | | 275 | | | | | 280 | | | | | 285 | | | |
| Phe | Val | Gly | Val | Lys | Phe | Arg | Thr | His | Leu | Lys | His | Val | Leu | Arg | Gln |
| | 290 | | | | | 295 | | | | | 300 | | | | |
| Phe | Trp | Phe | Cys | Arg | Leu | Gln | Ala | Pro | Ser | Pro | Ala | Ser | Ile | Pro | His |
| 305 | | | | | 310 | | | | | 315 | | | | | 320 |
| Ser | Pro | Gly | Ala | Phe | Ala | Tyr | Glu | Gly | Ala | Ser | Phe | Tyr | | | |
| | | | | 325 | | | | | 330 | | | | | | |

* P<0.05 significant difference from control in t-test

Fig.26
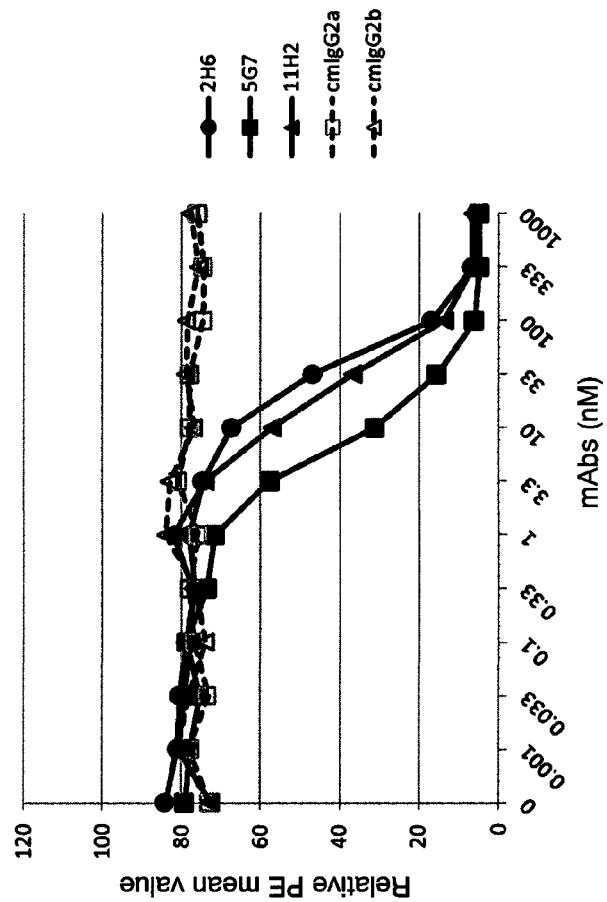
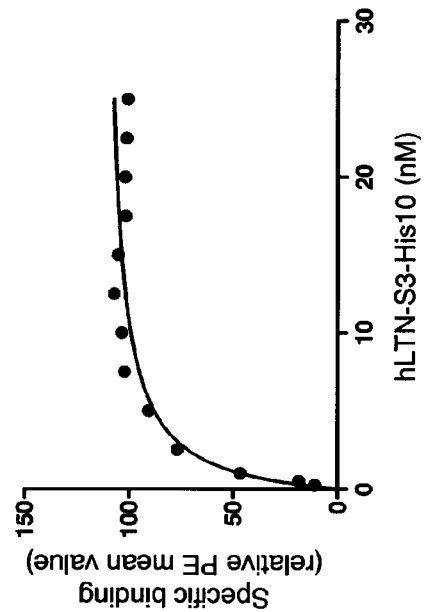

ANTI-HUMAN XCR1 ANTIBODIES

TECHNICAL FIELD

The present invention relates to an antibody that binds to human XCR1.

BACKGROUND ART

Chemokine is a collective term for basic heparin-binding proteins that have effects on leukocyte chemotaxis and leukocyte activation. Based on a comparison of the primary structures of various chemokines, the chemokines are classified into CXC, CC, C, and CX3C subfamilies according to the positions of conserved cysteine residues. XCL1 (also referred to as lymphotactin (Ltn) or lymphotactin α (Ltn-α)) and XCL2 (also referred to as lymphotactin β (Ltn-β)) are chemokines classified into the subfamily C described above. XCR1 (also referred to as GPR5, SCM-1α, or ATAC) is a G protein-coupled chemokine receptor, which specifically binds to XCL1 and XCL2.

Expression of XCR1 in various human tissues has been examined at the mRNA level. Expression of XCR1 is reportedly high in placenta, but low in spleen and thymus gland (NON PATENT LITERATURE 1). Further, XCR1 is mainly expressed in dendritic cells. In mice, XCR1 is highly expressed, particularly in CD8α+ dendritic cells (NON PATENT LITERATURE 2; and NON PATENT LITERATURE 3). The CD8α+ dendritic cells are normally present in secondary lymphoid tissues such as spleen and lymph nodes, and are known to perform "cross-presentation," which serves an important role in reactions against infection and immunological responses to tumor cells. XCR1 is also known to be highly expressed in human CD141+ dendritic cells, which are considered to be homologues of mouse CD8α+ dendritic cells (NON PATENT LITERATURE 4).

Antigen taken up from the outside of cells into antigen-presenting cells is usually degraded into peptide, presented on class II major histocompatibility antigen (MHC class II), and recognized by CD4+ T-cells. In contrast, there is a case where the antigen taken up from the outside of cells is presented on class I major histocompatibility antigen (MHC class I) via a pathway different from the usual pathway described above. This antigen presentation process is referred to as "cross-presentation." In this process, the antigen presented on MHC class I is recognized by the CD8+ T-cells, and then differentiated into cytotoxic T-cells (CTL) that play a role in phylaxis and the elimination of tumor cells in the host (Non Patent Literature 5).

Migration of various immune-related cells occurs during inflammation reaction. In particular, migration of dendritic cells to a local inflammatory site occurs for phagocytosis of antigens. Chemokines and chemokine receptors play important roles in causing such migration of dendritic cells. After migration to a local inflammatory site, the dendritic cells present antigens to T-cells, and activate T-cells. Subsequently, the information is transmitted from T-cells to many more immune-related cells, amplifying the immune reaction (Non Patent Literature 6).

Among antigen presenting cells, the dendritic cells have particularly excellent antigen-presenting ability, and play a very important role in the activation of the T-cells. It has been suggested that because T-cells are involved in the development and exacerbation of various immune diseases including autoimmune diseases, to control dendritic cells is to control the activation of T-cells, which may lead to the amelioration of various immune diseases (Non Patent Literature 6; and Non Patent Literature 7).

Further, it has been shown that a rabbit-derived polyclonal antibody against human XCR1 has an effect of inhibiting XCL-induced migration of normal oral keratinocytes and oral cancer cells (Non Patent Literature 8).

CITATION LIST

Non Patent Literature

NPL 1: Yoshida T, Imai T, Kakizaki M, Nishimura M, Takagi S, Yoshie O. "Identification of Single C motif-1/lymphotactin receptor XCR1," J. Biol. Chem. 273: 16551-16554 (1998)

NPL 2: Crozat K, Guiton R, Contreras V, Feuillet V, Dutertre C A, Ventre E, Vu Manh T P, Baranek T, Storset A K, Marvel J, Boudinot P, Hosmalin A, Schwartz-Cornil I, Dalod M "The XC chemokine receptor 1 is a conserved selective marker of mammalian cells homologous to mouse CD8α+ dendritic cells," J Exp Med, 207: 1283-1292 (2010)

NPL 3: Dorner B G, Dorner M B, Zhou X, Opitz C, Mora A, Güttler S, Hutloff A, Mages H W, Ranke K, Schaefer M, Jack R S, Henn V, Kroczek R A "Selective expression of the chemokine receptor XCR1 on cross-presenting dendritic cells determines cooperation with CD8+ T-cells," Immunity, 31: 823-833 (2009)

NPL 4: Bachem A, Güttler S, Hartung E, Ebstein F, Schaefer M, Tannert A, Salama A, Movassaghi K, Opitz C, Mages H W, Henn V, Kloetzel P M, Gurka S, Kroczek R A, "Superior antigen cross-presentation and XCR1 expression define human CD11c$^+$CD141$^+$ cells as homologues of mouse CD8$^+$ dendritic cells," J Exp Med, 207: 1273-1281 (2010)

NPL 5: Kurts C, Robinson B W, Knolle P A, "Cross-priming in health and disease," Nat Rev Immunol, 10: 403-414 (2010)

NPL 6: Kurts C, Robinson B W, Knolle P A, "Cross-priming in health and disease," Nat Rev Immunol, 10: 403-414 (2010)

NPL 7: Waldner H, "The role of innate immune responses in autoimmune disease development," Autoimmun, Rev 8: 400-404 (2009)

NPL 8: Khurram S A, Whawell S A, Bingle L, Murdoch C, McCabe B M, Farthing P M, "Functional expression of the chemokine receptor XCR1 on oral epithelial cells," J Pathol, 221: 153-63 (2010)

SUMMARY OF INVENTION

Technical Problem

Knowledge that dendritic cells are involved in the development, exacerbation, and the like of immune diseases has been thus far accumulated using disease animal models. However, at present, neither an effective treatment method nor a prevention method has been developed for many immune diseases. Further, although an anti-human XCR1 antibody having an effect of inhibiting cell migration is known (Khurram S A, Whawell S A, Bingle L, Murdoch C, McCabe B M, Farthing P M, "Functional expression of the chemokine receptor XCR1 on oral epithelial cells," J Pathol, 221: 153-63 (2010)), because such an antibody is a rabbit-derived polyclonal antibody, it is unlikely to be immediately clinically applicable as a pharmaceutical product. In addition, the above document does not suggest that such an antibody inhibits cell migration of dendritic cells, and it is impossible to even predict that such an antibody will be effective in the treatment or prevention of immune diseases.

An object of the present invention is to provide a monoclonal antibody that selectively binds to human XCR1; preferably, a monoclonal antibody that selectively binds to human XCR1 and inhibits cell migration; further preferably an antibody that is effective in the treatment or prevention of immune diseases, in particular, immune diseases of the skin, based on the above-described effect.

Solution to Problem

The present inventors conducted intensive studies in an attempt to solve the above problem. As a result, they developed antibodies that bind to human XCR1, and found that such antibodies have an effect of inhibiting cell migration as well as a significant effect in the treatment or prevention of immune diseases, such as immune diseases of the skin, associated with migration of dendritic cells.

Hereinafter, in the present specification, the above-described antibodies are sometimes simply referred to as the "antibodies," "antibodies of the present invention," or "anti-human XCR1 antibodies."

Advantageous Effects of Invention

The antibodies of the present invention bind to human XCR1. The antibodies of the present invention include an antibody that inhibits binding between human XCR1 and human XCL1. Such an antibody has potential as an active ingredient to be added to a human XCR1-human XCL1 binding inhibitor.

The antibodies of the present invention also include an antibody that inhibits cell migration, particularly that of dendritic cells. Such an antibody has potential as an active ingredient to be added to a cell migration inhibitor, particularly a dendritic cell migration inhibitor. Further, the antibodies of the present invention also include an antibody that specifically recognizes BDCA3 (also referred to as CD141) positive cells. Therefore, a pharmaceutical composition comprising the antibodies of the present invention has potential as a therapeutic agent for the treatment of immune diseases associated with cell migration, particularly dendritic cell migration. In particular, the pharmaceutical composition has potential as a therapeutic agent for the treatment of immune diseases of the skin such as delayed-type hypersensitivity, psoriasis, parapsoriasis, atopic dermatitis, contact dermatitis, dermatomyositis, polymyositis, inclusion body myositis, autoimmune blistering disease (e.g., pemphigus, pemphigoid, or acquired epidermolysis bullosa), pustulosis, systemic scleroderma, herpes gestationis, linear IgA bullous dermatosis, alopecia greata, vitiligo vulgaris, skin diseases associated with collagenosis (e.g., systemic lupus erythematosus, Sjögren syndrome, or mixed connective tissue disease), skin diseases associated with Addison's disease, skin diseases associated with graft-versus-host disease (GVHD), eczema, and urticaria.

In addition to these immune diseases of the skin, the antibodies of the present invention also has potential as therapeutic agents for the treatment of immune diseases such as diabetes mellitus type 1, glomerulonephritis, autoimmune hepatitis, multiple sclerosis, ankylosing spondylitis, thyroiditis, graft rejection, Crohn's disease, rheumatoid arthritis, inflammatory bowel disease, anterior uveitis, Wegener's granulomatosis, or Behçet's disease.

BRIEF DESCRIPTION OF DRAWINGS

FIG. 7 shows the comparison of amino acid sequences of heavy chain CDRs 1 to 3 and light chain CDRs 1 to 3 of the antibodies of the present invention. The figure also shows the generalized amino acid sequences of heavy chain CDRs 1 to 3 and light chain CDRs 1 to 3.

FIGS. 8A and 8B respectively show the results obtained by comparing the degree of ear swelling (mm) 24 hours and 48 hours after induction by DNFB between the mouse anti-human XCR1 antibody (5G7) of the present invention and the control antibody.

FIG. 10 shows amino acid sequences of human XCR1 to which the antibodies of the present invention bind.

FIG. 26 shows the analysis of the result of the competitive ligand binding assay of mouse anti-human XCR1 antibodies of the present invention.

DESCRIPTION OF EMBODIMENTS

Figure 1:
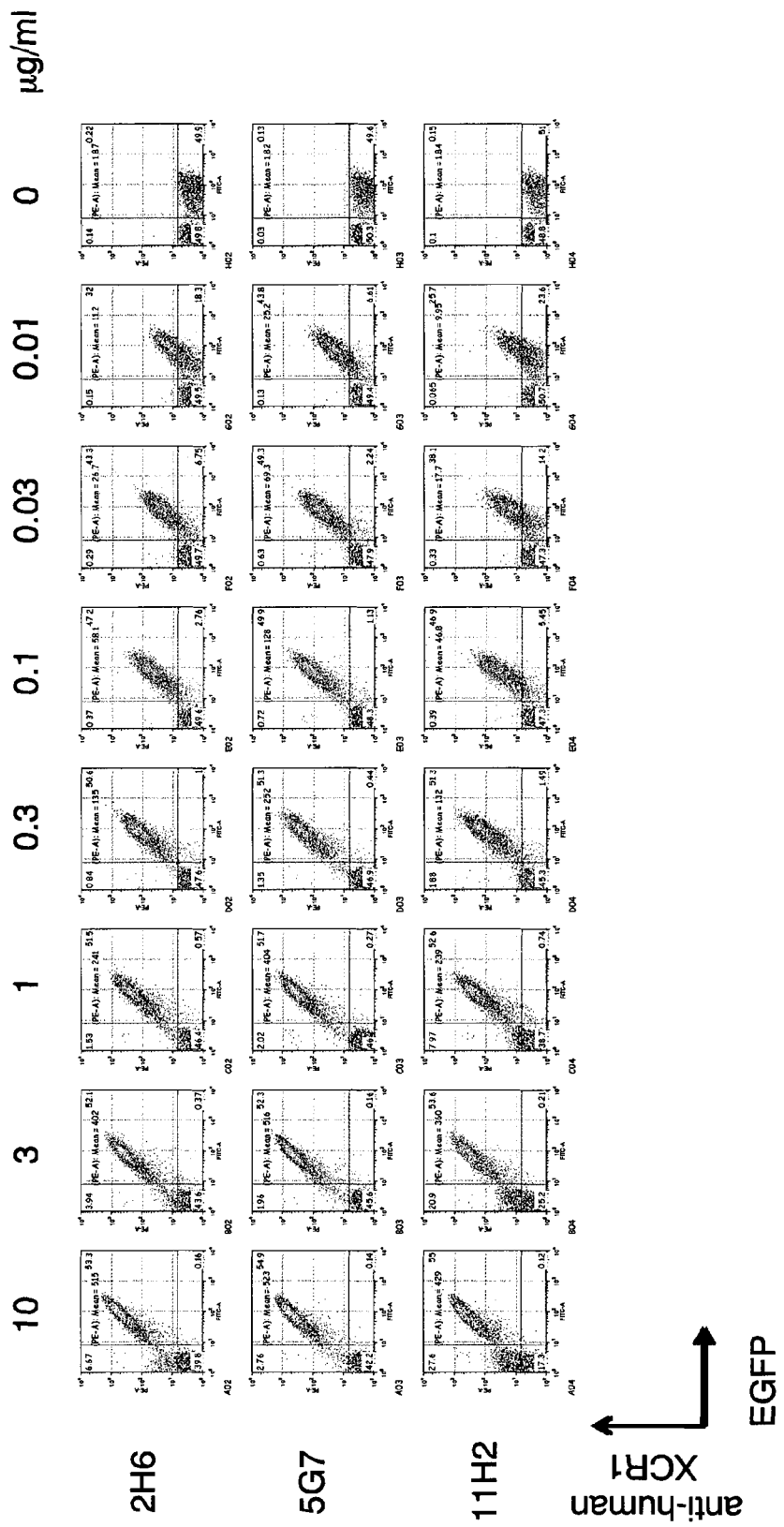
FIG. 1 shows the results of FACS analysis of the reactivity of mouse anti-human XCR1 antibodies (2H6, 5G7, and 11H2) to human XCR1-EGFP-expressing B300.19 cells.

Various techniques used to practice the present invention are easily and reliably enabled for a person skilled in the art based on known documents and the like, except for those techniques whose sources are clearly identified herein. For example, in regard to genetic engineering and molecular biological techniques, reference may be made to documents such as Sambrook and Russell, "Molecular Cloning: A Laboratory Manual," Cold Spring Harbor Laboratory Press, New York, (2001); and Ausubel, F M et al., "Current Protocols in Molecular Biology," John Wiley & Sons, New York, N.Y.

Further, in regard to antibody engineering techniques, reference may be made to documents such as Kabat et al., "Sequences of Proteins of Immunological Interest," U.S. Department of Health and Human Services, (1983); and Konterman and Dübel, "Antibody Engineering," Springer.

EXPLANATION OF THE TERMS

The term "nucleic acid" encompasses, for example, ribonucleotides, deoxyribonucleotides, and their modified forms. The nucleic acid may be either single- or double-stranded, and either polynucleotide or oligonucleotide.

The term "protein" refers to a compound in which two or more amino acids are linked by peptide bonds.

The term "monoclonal antibody" refers to an antibody obtained from a population of substantially homogeneous antibodies. In other words, the individual antibodies included in the population are identical except for naturally occurring mutations that may be present in minor amounts. Monoclonal antibodies are highly specific, and directed to a single antigenic site. Further, in contrast to polyclonal antibody preparations comprising different antibodies directed to different determinants (epitopes), each monoclonal antibody is directed to a single determinant on the antigen. In addition to their specificities, monoclonal antibodies are also advantageous in that they can be synthesized without contamination by other antibodies. The modifier "monoclonal" refers to a characteristic of an antibody obtained from a population of substantially homogeneous antibodies, and should not be interpreted to mean that antibodies must be produced by any specific method.

For example, a monoclonal antibody that should be used in accordance with the present invention can be prepared by the hybridoma method first described by Köhler G and Milstein C, "Continuous cultures of fused cells secreting antibody of predefined specificity," Nature, 256: 495-7 (1975), or by a recombinant DNA method (see U.S. Pat. No. 4,816,567).

Further, "monoclonal antibodies" can be isolated from phage antibody library by using a technique, for example, described by Clackson T, Hoogenboom H R, Griffiths A D, and Winter G, "Making antibody fragments using phage display libraries," Nature, 352: 624-8 (1991); or Marks J D, Hoogenboom H R, and Bonnert T P, McCafferty J, Griffiths A D, Winter G, "By-passing immunization: Human antibodies from V-gene libraries displayed on phage," J Mol Biol, 222: 581-97 (1991).

The "identity" between amino acid sequences or nucleotide sequences refers to the degree of identical amino acid sequences or nucleotide sequences between two or more comparable amino acid sequences or nucleotide sequences. Accordingly, when the identity between two amino acid sequences or nucleotide sequences is high, the identity or similarity of these sequences is high. The level of identity between amino acid sequences or nucleotide sequences is determined, for example, using FASTA, which is a sequence analysis tool, based on default parameters.

Alternatively, it can be determined using the algorithm BLAST by Karlin and Altschul (Karlin S, Altschul S F, "Methods for assessing the statistical significance of molecular sequence features by using general scoring schemes," Proc Natl Acad Sci USA, 87: 2264-2268 (1990); and Karlin S, Altschul S F, "Applications and statistics for multiple high-scoring segments in molecular sequences," Proc Natl Acad Sci USA, 90: 5873-7 (1993)). Programs such as BLASTN and BLASTX based on the above-described BLAST algorithm have been developed (Altschul S F, Gish W, Miller W, Myers E W, Lipman D J, "Basic local alignment search tool," J Mol Biol, 215: 403-10 (1990)). For example, BLASTN may be used when analyzing the nucleotide sequence, by setting, for example, the score to 100 and the word length to 12, as parameters.

In addition, BLASTX may be used when analyzing the amino acid sequence, by setting, for example, the score to 50 and the word length to 3, as parameters.

When BLAST and Gapped BLAST programs are used, default parameters of each program may be used. Specific techniques of these analysis methods are known. Reference may be made to the website of the National Center of Biotechnology Information (NCBI) (http://www.ncbi.nlm.nih.gov/).

Anti-Human XCR1 Antibody

The antibodies of the present invention are isolated antibodie's.

The antibodies of the present invention bind to human XCR1. The amino acid sequence of human XCR1 is an amino acid sequence shown by NCBI Reference Sequence: NP_001019815.1 or NP_005274.1. In regard to these amino acid sequences, reference may be made to the NCBI websites (respectively, http://www.ncbi.nlm.nih.gov/protein/NP_001019815.1 and http://www.ncbi.nlm.nih.gov/protein/NP_005274.1).

A specific antibody of a first embodiment of the present invention is an antibody comprising a heavy chain variable region comprising
a heavy chain CDR 1 described in (A) or (a) below,
a heavy chain CDR 2 described in (B) or (b) below, and
a heavy chain CDR 3 described in (C) or (c) below; and
a light chain variable region comprising
a light chain CDR 1 described in (D) or (d) below,
a light chain CDR 2 described in (E) or (e) below, and
a light chain CDR 3 described in (F) or (f) below.
(A) A heavy chain CDR 1 consisting of the amino acid sequence of SEQ ID NO: 53,
(B) a heavy chain CDR 2 consisting of the amino acid sequence of SEQ ID NO: 54,
(C) a heavy chain CDR 3 consisting of the amino acid sequence of SEQ ID NO: 55;
(D) a light chain CDR 1 consisting of the amino acid sequence of SEQ ID NO: 56,
(E) a light chain CDR 2 consisting of the amino acid sequence of SEQ ID NO: 57, and
(F) a light chain CDR 3 consisting of the amino acid sequence of SEQ ID NO: 58.
(a) A heavy chain CDR 1 consisting of the amino acid sequence of SEQ ID NO: 41,
(b) a heavy chain CDR 2 consisting of the amino acid sequence of SEQ ID NO: 42,
(c) a heavy chain CDR 3 consisting of the amino acid sequence of SEQ ID NO: 43;
(d) a light chain CDR 1 consisting of the amino acid sequence of SEQ ID NO: 44,
(e) a light chain CDR 2 consisting of the amino acid sequence of SEQ ID NO: 45, and
(f) a light chain CDR 3 consisting of the amino acid sequence of SEQ ID NO: 46.

The term "CDR" defined in relation to the antibodies of the present invention is an abbreviation for Complementarity Determining Region, and is also referred to as a complementarity determining region. CDRs are present in the variable region of immunoglobulin, and are deeply involved in the specific binding of an antibody to an antigen. Further, "light chain CDR" refers to a CDR that is present in the variable region of the light chains of immunoglobulin, and "heavy chain CDR" refers to a CDR that is present in the variable region of the heavy chains of immunoglobulin.

In addition, "variable region" refers to a region that includes the above-described CDR 1 to CDR 3 (hereinafter simply referred to as "CDRs 1 to 3"). Although the order of arrangement of the CDRs 1 to 3 is not particularly limited, preferably, CDR 1, CDR 2, and CDR 3 are arranged in that order or in the opposite order from N-terminus to C-terminus in a sequential manner or via other amino acid sequences called framework regions (FRs). Further, the "heavy chain variable region" is a region where the above-described heavy chain CDRs 1 to 3 are located, and the "light chain variable region" is a region where the above-described light chain CDRs 1 to 3 are located.

As described above, the region other than the above-described CDRs 1 to 3 in the each variable region is called a framework region (FR). In particular, the region between the N-terminus and CDR 1 in each variable region is defined as FR 1, the region between CDR 1 and CDR 2 is defined as FR 2, the region between CDR 2 and CDR 3 is defined as FR 3, and the region between CDR3 and the C-terminus in each variable region is defined as FR 4.

The FRs also have a function as linker sequences for linking the CDRs 1 to 3 that are particularly important as the antigen recognition sequences. The FRs are the regions that contribute to the formation of the three-dimensional structure of the entire variable region.

A preferable antibody of the first embodiment according to the present invention is an antibody comprising a heavy chain variable region comprising
a heavy chain CDR 1 of (g) below, (m) below, or (a) above,
a heavy chain CDR 2 of (h) below, (n) below, or (b) above, and
a heavy chain CDR 3 of (i) below, (o) below, or (c) above; and
a light chain variable region comprising
a light chain CDR 1 of (j) below, (p) below, or (d) above,
a light chain CDR 2 of (k) below, (q) below, or (e) above, and
a light chain CDR 3 of (l) below, (r) below, or (f) above.
(g) A heavy chain CDR 1 consisting of the amino acid sequence of SEQ ID NO: 17,
(h) a heavy chain CDR 2 consisting of the amino acid sequence of SEQ ID NO: 18,
(i) a heavy chain CDR 3 consisting of the amino acid sequence of SEQ ID NO: 19;
(j) a light chain CDR 1 consisting of the amino acid sequence of SEQ ID NO: 20,
(k) a light chain CDR 2 consisting of the amino acid sequence of SEQ ID NO: 21,
(l) a light chain CDR 3 consisting of the amino acid sequence of SEQ ID NO: 22;
(m) a heavy chain CDR 1 consisting of the amino acid sequence of SEQ ID NO: 29,
(n) a heavy chain CDR 2 consisting of the amino acid sequence of SEQ ID NO: 30,
(o) a heavy chain CDR 3 consisting of the amino acid sequence of SEQ ID NO: 31;
(p) a light chain CDR 1 consisting of the amino acid sequence of SEQ ID NO: 32,
(q) a light chain CDR 2 consisting of the amino acid sequence of SEQ ID NO: 33, and
(r) a light chain CDR 3 consisting of the amino acid sequence of SEQ ID NO: 34.

The heavy chain CDR 3 described in (i) and the heavy chain CDR 3 described in (o) comprise identical amino acid sequences.

An antibody of a second embodiment of the present invention is an antibody comprising
a heavy chain variable region comprising the heavy chain CDRs 1 to 3 described in (A)-(C) above or
a heavy chain variable region comprising the heavy chain CDRs 1 to 3 described in (a)-(c) above; and
a light chain variable region comprising the light chain CDRs 1 to 3 described in (D)-(F) above or
a light chain variable region comprising the light chain CDRs 1 to 3 described in (d)-(f) above.

A more preferable antibody of the second embodiment is an antibody comprising any one of
a heavy chain variable region comprising the heavy chain CDRs 1 to 3 described in (g)-(i) above, a heavy chain variable region comprising the heavy chain CDRs 1 to 3 described in (m)-(o) above, and
a heavy chain variable region comprising the heavy chain CDRs 1 to 3 described in (a)-(c) above; and
any one of
a light chain variable region comprising the light chain CDRs 1 to 3 described in (j)-(l) above,
a light chain variable region comprising the light chain CDRs 1 to 3 described in (p)-(r) above, and
a light chain variable region comprising the light chain CDRs 1 to 3 described in (d)-(f) above.

An antibody of a third embodiment of the present invention is an antibody comprising
a heavy chain variable region comprising the heavy chain CDRs 1 to 3 described in (A)-(C) above, and
a light chain variable region comprising the light chain CDRs 1 to 3 described in (D)-(F) above, or
an antibody comprising
a heavy chain variable region comprising the heavy chain CDRs 1 to 3 described in (a)-(c) above, and
a light chain variable region comprising the light chain CDRs 1 to 3 described in (d)-(f) above.

A more preferable antibody of the third embodiment is an antibody comprising
a heavy chain variable region comprising the heavy chain CDRs 1 to 3 described in (g)-(i) above, and
a light chain variable region comprising the light chain CDRs 1 to 3 described in (j)-(l) above;
an antibody comprising
a heavy chain variable region comprising the heavy chain CDRs 1 to 3 described in (m)-(o) above, and
a light chain variable region comprising the light chain CDRs 1 to 3 described in (p)-(r) above; or
an antibody comprising
a heavy chain variable region comprising the heavy chain CDRs 1 to 3 described in (a)-(c) above, and
a light chain variable region comprising the light chain CDRs 1 to 3 described in (d)-(f) above.

The molecular structures of the antibodies of the present invention are not limited to that of immunoglobulin insofar as the antibodies have the above-described heavy and light chain variable regions. Examples of specific structures include molecular structures of $F(ab')_2$ that does not comprise the Fc region; Fab formed by papain digestion of immunoglobulin and composed of CH1 and CL domains as well as the heavy and light chain variable regions; Fv that does not comprise the immunoglobulin constant region; and scFv, which is a single-chain Fv antibody.

The antibodies of the present invention may also be multivalent, in which the above molecular structures are combined. Such a multivalent antibody is formed by a technique of accumulating scFv constructs, as in an scFv-Fc construct formed by the combination of the Fc region and scFv construct described above; and a construct called a minibody, formed by the combination of CH3 domain of the constant region and the scFv construct described above. The term "multivalent" refers to the presence of multiple antigen-binding sites. In regard to the antibodies of the present invention, the term is used in the same meaning as the presence of multiple sites that bind to human XCR1. The antibodies of the present invention may also have a human constant region in addition to the above-described heavy and light chain variable regions.

In immunoglobulin, the "constant region" of the heavy chains comprises domains called CH1, CH2, and CH3; and the "constant region" of the light chains comprises a domain called CL.

As described above, when the antibodies of the present invention have the constant region, it is preferable that the heavy chain variable region is linked to at least one of the CH1, CH2, and CH3 domains, and that the light chain variable region is linked to CL. Further, the heavy chain variable region is preferably directly linked to CH1.

The constant region of the antibodies of the present invention is a constant region derived from human immunoglobulin, preferably, a constant region derived from human immunoglobulin IgG. The subtype of human immunoglobulin IgG is not particularly limited, and may be suitably selected, for example, according to whether to impart ADCC activity, CDC activity, and the like described below to the antibodies.

The term "ADCC activity" is an abbreviation for Antibody-Dependent Cellular Cytotoxicity activity. It is an activity in which cells such as NK cells expressing receptors specific for the antibody Fc region bind to the antibodies and damage cells present in the vicinity of the antibodies. Additionally, the term "CDC activity" is an abbreviation for Complement-Dependent Cytotoxicity activity. In the case of humans, the subtype of IgG having a high ADCC and/or CDC activity is IgG1, and the subtype of IgG having a low ADCC and/or CDC activity is IgG2 or IgG4.

Amino acid residues in the Fc region of the antibodies of the present invention may be mutated in order to induce a change in ADCC and/or CDC activity. Mutations to be introduced are not particularly limited, and known mutations may be introduced. For example, the following mutations may be introduced into the constant region of IgG1 for the purpose of increasing ADCC activity: S239D, I332E, S239D/I332E, S239D/I332E/A330L, and the like (Lazar G A, Dang W, Karki S, Vafa O, Peng J S, Hyun L, Chan C, Chung H S, Eivazi A, Yoder S C, Vielmetter J, Carmichael D F, Hayes R J, Dahiyat B I, "Engineered antibody Fc variants with enhanced effector function," Proc Natl Acad Sci USA, 103: 4005-10 (2006)); and S298A, K334A, S298A/K334A, S298A/E333A/K334A, etc., (Shields R L, Namenuk A K, Hong K, Meng Y G, Rae J, Briggs J, Xie D, Lai J, Stadlen A, Li B, Fox J A, Presta L G, "High resolution mapping of the binding site on human IgG1 for Fc gamma RI, Fc gamma RII, Fc gamma RIII, and FcRn and design of IgG1 variants with improved binding to the Fc gamma R," J Biol Chem, 276: 6591-604 (2001)).

Examples of mutations that increase CDC activity include S267E, H268F, S324T, S267E/H268F, S267E/S324T, H268F/S324T, S267E/H268F/S324T (Moore G L, Chen H, Karki S, Lazar G A, "Engineered Fc variant antibodies with enhanced ability to recruit complement and mediate effector functions," MAbs, 2:181-9 (2010)).

Additionally, for the purpose of lowering ADCC activity, known mutations may be introduced; for example, V234A/G237A (Cole M S, Anasetti C, Tso J Y, "Human IgG2 variants of chimeric anti-CD3 are nonmitogenic to T cells," J Immunol, 159:3613-21 (1997)), H268Q/V309L/A330S/P331S (An Z, Forrest G, Moore R, Cukan M, Haytko P, Huang L, Vitelli S, Zhao J Z, Lu P, Hua J, Gibson C R, Harvey B R, Montgomery D, Zaller D, Wang F, Strohl W, "IgG2 m4, an engineered antibody isotype with reduced Fc function," MAbs, 1:572-9 (2009)), and the like.

The numbering of the above-described amino acids to be mutated is in accordance with the Eu numbering (see Sequences of proteins of immunological interest, NIH Publication No. 91-3242).

Chimeric Antibody

Among the antibodies of the present invention, an antibody in which the heavy and light chain variable regions comprise amino acid sequences derived from non-human species and the constant region comprises amino acid sequences derived from human is defined as a "chimeric antibody."

A first embodiment of the chimeric antibody of the present invention is a chimeric antibody comprising a heavy chain consisting of the amino acid sequence of SEQ ID NO: 13 and a light chain of SEQ ID NO: 14.

As shown in Table 5, the amino acid sequence of SEQ ID NO: 13 comprises the heavy chain CDRs 1 to 3 of SEQ ID NOs: 17 to 19 among the heavy chain CDRs 1 to 3 described above in the heavy chain variable region. Further, as shown in Table 5, the amino acid sequence of SEQ ID NO: 14 comprises the light chain CDRs 1 to 3 of SEQ ID NOs: 20 to 22 among the light chain CDRs 1 to 3 described above in the light chain variable region.

The chimeric antibody of the present invention comprises variants caused by mutations in the heavy chain consisting of the amino acid sequence of SEQ ID NO: 13 and/or the light chain consisting of the amino acid sequence of SEQ ID NO: 14, insofar as such mutations do not abolish the binding ability of the chimeric antibody to human XCR1.

Such variants in the heavy and light chains are preferably obtained by introducing mutations into at least any one of FR 1 to FR 4 (hereinafter simply referred to as "FRs 1 to 4") of the variable region, or at least one site in the constant region of the respective amino acid sequences of SEQ ID NOs: 13 and 14.

The specific number of mutations introduced into the heavy and light chains is not particularly limited. Mutations are usually introduced to obtain a variant having 85% or higher identity, preferably 90% or higher identity, more preferably 95% or higher identity, and most preferably 99% or higher identity with the amino acid sequence before mutation.

The term "mutation" used herein includes substitution, deletion, insertion, and the like. A known method without specific limitation can be employed as a specific method for introducing mutations. For example, in the case of substitution, conservative substitution may be employed. The term "conservative substitution" refers to a substitution of an amino acid residue with another amino acid residue having a similar side chain.

For example, a substitution between amino acid residues with basic side chains such as lysine, arginine, and histidine corresponds to a conservative substitution. In addition, the following substitutions between the amino acid residues also correspond to conservative substitutions: substitutions between amino acid residues with acid side chains such as aspartic acid and glutamic acid; substitutions between amino acid residues with non-charged polar side chains such as glycine, asparagine, glutamine, serine, threonine, tyrosine, and cysteine; substitutions between amino acid residues with non-polar side chains such as alanine, valine, leucine, isoleucine, proline, phenylalanine, methionine, and tryptophan; substitutions between amino acid residues with β-branched side chains such as threonine, valine, and isoleucine; and substitutions between amino acid residues with aromatic side chains such as tyrosine, phenylalanine, tryptophan, and histidine.

Humanized Antibodies

Among the antibodies of the present invention, the antibody comprising the above-described CDRs 1 to 3 in the heavy and light chain variable regions, in which the FRs 1-4 comprise a human-derived amino acid sequence or a variant thereof, is defined as a "humanized antibody."

Such FRs comprising a human-derived amino acid sequence are not particularly limited, and may be determined based on a known technique.

Examples of such FRs include fully human framework regions or sub-regions, with FRs derived from human germline sequences being preferable. Reference may be suitably made to, for example, the NCBI website, which shows a list of currently known sequences of FRs as examples of fully human framework regions or sub-regions.

Non-limiting examples of the sequences of the human heavy chain variable region include VH1-18, VH1-2, VH1-24, VH1-3, VH1-45, VH1-46, VH1-58, VH1-69, VH1-8, VH2-26, VH2-5, VH2-70, VH3-11, VH3-13, VH3-15, VH3-16, VH3-20, VH3-21, VH3-23, VH3-30, VH3-33, VH3-35, VH3-38, VH3-43, VH3-48, VH3-49, VH3-53, VH3-64, VH3-66, VH3-7, VH3-72, VH3-73, VH3-74, VH3-9, VH4-28, VH4-31, VH4-34, VH4-39, VH4-4, VH4-59, VH4-61, VH5-51, VH6-1, and VH7-81.

Non-limiting examples of the sequences of the human light chain variable region include VL1-11, VL1-13, VL1-16, VL1-17, VL1-18, VL1-19, VL1-2, VL1-20, VL1-22, VL1-3, VL-4, VL1-5, VL1-7, VL1-9, VL2-1, VL2-11, VL2-13, VL2-14, VL2-15, VL2-17, VL2-19, VL2-6, VL2-7, VL-8, VL3-2, VL3-3, VL3-4, VL4-1, VL4-2, VL4-3, VL4-4, VL4-6, VL5-1, VL5-2, VL5-4, and VL5-6.

Fully human FRs are selected from these functional germline genes. Each of these FRs is usually different because of the modification of a limited number of amino acids. These FRs may be used in a combination with the CDRs described in the present specification. Non-limiting additional examples of human FRs to be used in combination with the above-described CDRs include KOL, NEWM, REI, EU, TUR, TEI, LAY, and POM. In regard to the examples of these human FRs, reference may be made to the following documents: Kabat, et al., "Sequences of Proteins of Immunological Interest," US Department of Health and Human Services, NIH (1991) USA; Wu T T, Kabat E A, "An analysis of the sequences of the variable regions of Bence Jones proteins and myeloma light chains and their implications for antibody complementarity," J Exp Med, 132: 211-50 (1970); and the like.

A first embodiment of the humanized antibody of the present invention is a humanized antibody comprising a heavy chain variable region comprising the amino acid sequence of either SEQ ID NO: 60 or SEQ ID NO: 64, and a light chain variable region of either SEQ ID NO: 68 or SEQ ID NO: 72.

A more preferable embodiment is a humanized antibody comprising a heavy chain variable region comprising the amino acid sequence of SEQ ID NO: 60 and a light chain variable region comprising the amino acid sequence of SEQ ID NO: 68, or a humanized antibody comprising a heavy chain variable region comprising the amino acid sequence of SEQ ID NO: 64 and a light chain variable region comprising the amino acid sequence of SEQ ID NO: 72.

As respectively shown in Tables 11-1 and 12-1, the amino acid sequences of SEQ ID NO: 60 and SEQ ID NO: 64 comprise the heavy chain CDRs 1 to 3 of SEQ ID NOs: 17 to 19 among the above-described heavy chain CDRs 1 to 3 in the heavy chain variable region. As respectively shown in Tables 13-1 and 14-1, the amino acid sequences of SEQ ID NO: 68 and SEQ ID NO: 72 comprise the light chain CDRs 1 to 3 of SEQ ID NOs: 20-22 among the above-described light chain CDRs 1 to 3 in the light chain variable region.

The humanized antibody of the present invention comprises variants caused by mutations in the heavy chain variable region comprising the amino acid sequence of SEQ ID NO: 60 or 64 and/or the light chain variable region comprising the amino acid sequence of SEQ ID NO: 68 or 72, insofar as such mutation do not abolish the binding ability to human XCR1. Such variants in the heavy and light chain variable regions are preferably obtained by introducing mutations into the respective FRs 1 to 4.

The specific number of mutations into the heavy and light chain variable regions is not particularly limited. Mutations are usually introduced to obtain a variant having 85% or higher identity, preferably 90% or higher identity, more preferably 95% or higher identity, and most preferably 99% or higher identity with the amino acid sequence before mutation.

The term "mutation" used herein includes substitution, deletion, insertion, and the like. As is the case with the chimeric antibody described above, conservative substitution and the like may be employed as a specific method for introducing mutations.

The second embodiment of the humanized antibody of the present invention includes an antibody comprising a human constant region. Examples thereof include a humanized antibody comprising a heavy chain comprising the amino acid sequence of either SEQ ID NO: 59 or 63, and a light chain comprising the amino acid sequence of either SEQ ID NO: 67 or 71.

A more preferable embodiment is a humanized antibody comprising a heavy chain comprising the amino acid sequence of SEQ ID NO: 59 and a light chain comprising the amino acid sequence of SEQ ID NO: 67, or a humanized antibody comprising a heavy chain comprising the amino acid sequence of SEQ ID NO: 63 and a light chain comprising the amino acid sequence of SEQ ID NO: 71.

As shown in Table 11-1, the amino acid sequence of SEQ ID NO: 59 comprises an amino acid sequence corresponding to the heavy chain variable region of SEQ ID NO: 60, and therefore comprises the heavy chain CDRs 1 to 3 of SEQ ID NO: 17-19 among the heavy chain CDRs 1 to 3 described above. Further, as shown in Table 13-1, the amino acid sequence of SEQ ID NO: 67 comprises an amino acid sequence corresponding to the light chain variable region of SEQ ID NO: 68, and therefore comprises the light chain CDRs 1 to 3 of SEQ ID NO: 20-22 among the light chain CDRs 1 to 3 described above.

The heavy and/or light chain described above comprises variants caused by mutations insofar as such mutations do not abolish the binding ability to human XCR1. Such variants in the heavy and light chains are preferably obtained by introducing mutations into the FRs 1 to 4 or the constant region.

The specific number of mutations into the heavy and light chains is not particularly limited. Mutations are usually introduced to obtain a variant having 85% or higher identity, preferably 90% or higher identity, more preferably 95% or higher identity, and most preferably 99% or higher identity with the amino acid sequence before mutation.

The term "mutation" used herein includes substitution, deletion, insertion, and the like. As is the case with the chimeric antibody described above, conservative substitution and the like may be employed as a specific method for introducing mutations.

Function of the Antibodies

The antibodies of the present invention bind to human XCR1. The meaning of the term "bind" used herein encompasses, at least, binding through hydrophobic bonds and the like as seen in the case of an interaction between proteins. In other words, antibodies that bind to human XCR1 at least by hydrophobic binding are sufficient as the antibodies of the present invention. Further, the antibodies of the present invention and human XCR1 may or may not be dissociated after binding.

The antibodies of the present invention preferably specifically bind to human XCR1. The term "specific binding" as used herein refers to specific binding to human XCR1, meaning that the antibodies preferentially bind to human XCR1 when human XCR1 is present concurrently with molecules other than human XCR1, in particular, molecules having a structure similar to that of human XCR1, such as a homologue of human XCR1 or an orthologue of human XCR1.

That the antibodies of the present invention specifically bind to human XCR1 does not mean that the ability of binding to the above-described homologue or orthologue of human XCR1 is excluded.

The degree of binding of the antibodies of the present invention to human XCR1 can be evaluated by a reaction rate constant such as a Kd, Koff, or Kon value. A Kd value is a value obtained by dividing a Koff value by a Kon value.

The reaction rate constant between the antibodies of the present invention and human XCR1 is not particularly limited.

The antibodies of the present invention bind to the extracellular domain of human XCR1. Specifically, the antibodies bind to one or more of amino acid regions 1 to 31, 90 to 103, 168 to 190, and 251 to 267, which corresponds to the extracellular domain region of the amino acid sequence (SEQ ID NO: 91; FIG. 10) of the above-described NCBI Reference Sequence: NP_001019815.1 or NP_005274.1.

More preferably, in the amino acid sequence of SEQ ID NO: 91, the antibodies bind to at least three amino acids selected from the group consisting of the $8^{th}$, $11^{th}$, $12^{th}$, $13^{th}$, $14^{th}$, $16^{th}$, $17^{th}$, $22^{nd}$, $23^{rd}$, $176^{th}$, and $177^{th}$ amino acids.

Said "at least three amino acids" includes, for example, three or more amino acids, four or more amino acids, five or more amino acids, six or more amino acids, seven or more amino acids, eight or more amino acids, nine or more amino acids, ten or more amino acids, or eleven amino acids.

Note that the "epitope" in the present invention is also referred to as an "antigenic determinant," and includes "linear epitope" and "discontinuous epitope." A "linear epitope" is an epitope that is recognized by antibodies by the primary structure of the amino acid sequence, rather than by its conformational structure. A "discontinuous epitope" is an epitope that is recognized by antibodies by the conformational structure of the amino acid sequence, based on the higher-order structure Note that a person skilled in the art can determine the epitope of the antibodies of the present invention by suitably modifying the methods described in the Examples of the present invention. For example, the epitope can be determined by synthesizing a protein or peptide consisting of a desirable amino acid sequence that falls within the extracellular domain of the amino acid sequence of human XCR1 using a known method, and confirming the binding between the obtained protein or peptide and the antibody by a known method. Alternatively, the epitope can be determined by preparing a mutant by introducing an appropriate mutation to desired amino acids in the amino acid sequence of human XCR1 by a known method, and confirming whether the binding between the prepared mutant and the antibody is reduced.

As described above, because the antibodies of the present invention bind to human XCR1, the antibodies of the present invention also include an antibody that inhibits binding between human XCR1 and human XCL1. Human XCL1 is also referred to as human lymphotactin (Ltn) or human lymphotactin α (Ltn-α). Such an inhibitory activity is sometimes referred to as "neutralizing activity" induced by the antibodies of the present invention. Because human XCR1 is present on the cellular surface as a receptor protein in vivo, inhibition of binding between human XCR1 and XCL1 by the antibodies of the present invention is preferably performed on the cellular surface. It does not matter whether the antibodies of the present invention have an inhibitory activity against binding between human XCR1 and XCL2 insofar as the antibodies have activity to at least inhibit binding between human XCR1 and XCL1. Accordingly, the antibodies of the present invention also include an antibody that inhibits binding not only between human XCR1 and XCL1, but also between human XCR1 and XCL2.

Examples of preferred cells include cells associated with an immune system activated by the binding between human XCR1 and human XCL1, with dendritic cells being particularly preferable. In particular, as shown by the later-described examples, because the antibodies of the present invention specifically recognize BDCA3+ dendritic cells, which are dendritic cells expressing a significant amount of human XCR1 proteins, it is preferable that the antibodies have an effect of inhibiting binding between human XCR1 and human XCL1 on BDCA3+ dendritic cells.

Binding between human XCR1 and human XCL1 is inhibited by the antibodies of the present invention. Non-limiting examples of forms of such inhibition include:

(1) The antibodies of the present invention bind to XCR1 at a site to which human XCL1 originally should bind, causing a steric obstruction to binding to human XCL1, and resulting in the inhibition of binding between human XCR1 and human XCL1.

(2) The antibodies of the present invention bind to human XCR1, causing a change in the three-dimensional structure of human XCR1, which consequently causes a change in the structure of human XCR1 to which human XCL1 should bind, thus resulting in the inhibition of binding between human XCR1 and human XCL1.

(3) The antibodies of the present invention bind to XCR1, causing an internalization of the receptor, which leads to the inhibition of binding between human XCR1 and human XCL1.

The inhibitory activity of the antibodies of the present invention against binding between human XCR1 and human XCL1 is evaluated based on $IC_{50}$ or $IC_{90}$ values. These values can be obtained, for example, by performing a competitive inhibition experiment or the like of binding of human XCL1 to human XCR1, using cells those express human XCR1 proteins in the presence of the antibodies of the present invention. A known method may be employed as a specific method of such a competitive inhibition experiment.

The antibodies of the present invention include an antibody that has an effect of inhibiting cell migration. The term "cell migration" refers to the phenomenon in which cells actively migrate as a result of external stimuli given to the cells and stimulus-induced activation of the intracellular signal transduction mechanism. Effects produced by the active cell migration vary depending on the functions of the cells. For example, in the case of cell migration of dendritic cells, such cell migration is a phenomenon that serves as one of the mechanisms in the immune system. In the present invention, inhibitory activity against cell migration is sometimes referred to as "neutralizing activity."

As described above, because the antibodies of the present invention suitably inhibit binding between human XCR1 and human XCL1 in dendritic cells, particularly BDCA3+ dendritic cells, the antibodies particularly preferably inhibit migration of dendritic cells, particularly BDCA3+ dendritic cells.

Human XCR1 is a seven-transmembrane G protein-coupled receptor. When human XCL1 binds to human XCR1, the three-dimensional structure of human XCR1 changes; and, as a result, a G protein coupled to the intracellular domain of human XCR1 is released, and a signal is transduced into the cells.

G proteins is prevented from release by the antibodies of the present invention inhibiting the binding between human XCR1 and XCL1 in accordance with the above-described forms (1), (2) or the like. As a result, no signal is transduced, thereby inhibiting the phenomena of cell migration.

Alternatively, the phenomena of cell migration may be inhibited as a result of a mechanism in which binding of the antibodies of the present invention to human XCR1 strengthens the bond between human XCR1 and G protein coupled to the intracellular domain of human XCR1, the release of G proteins consequently does not occur, thereby inhibiting intracellular signal transduction.

The inhibitory activity of the antibodies of the present invention against cell migration of human cells is evaluated based on an $IC_{50}$ or $IC_{90}$ value. Specific values are not particularly limited. For example, an $IC_{50}$ value is usually about 0.36 nM or less, preferably about 0.27 nM or less, and more preferably about 0.16 nM or less. For example, an $IC_{90}$ value is usually about 2.38 nM or less, preferably about 1.52 nM or less, and more preferably about 0.86 nM or less.

The antibodies of the present invention include, as an embodiment, an antibody that has an effect of decreasing cytotoxic T lymphocyte (CTL) activity. The mechanism of decreasing the CTL activity is, for example, the antibodies of the present invention inhibiting the interaction between human XCR1 and human XCL1 in dendritic cells. Among the dendritic cells, the above-described BDCA3+ dendritic cells are preferable.

Method for Preparing the Antibodies of the Present Invention

The antibodies of the present invention can be prepared by a method comprising the following three steps, although it is not limited thereto.

(i) Step 1 of introducing a vector into the host to transform the host, the vector comprising a nucleic acid comprising a nucleotide sequence encoding the antibodies of the present invention;

(ii) Step 2 of culturing the transformed host obtained in step 1 and collecting a fraction containing antibodies that bind to human XCR1; and (iii) Step 3 of isolating or purifying the above antibodies from the fraction obtained in step 2.

Step 1

The nucleic acid used in step 1 is a nucleic acid that encodes the antibodies of the present invention. The nucleotide sequence of the above nucleic acid can be determined using the in silico technique based on the amino acid sequence information of the antibodies of the present invention. At that time, it is preferable to determine the nucleotide sequence with reference to the codon frequency in the host employed in step 2. Specific examples of nucleotide sequences include the nucleotide sequence of SEQ ID NO: 3, 4, 7, 8, 11, 12, 15, 16, 61, 62, 65, 66, 69, 70, 73, or 74; or a variant thereof.

The above variant is preferably generated by introducing mutations (deletion, substitution, insertion, or the like) in the FR or constant region of the antibodies.

The specific number of mutations introduced into the variant is not particularly limited. Mutations are usually introduced to obtain a variant having 85% or higher identity, preferably 90% or higher identity, more preferably 95% or higher identity, and most preferably 99% or higher identity with the amino acid sequence before mutation.

Further, the above nucleic acid may comprise a nucleotide sequence that encodes a secretion signal peptide at the 5'-terminus. A specific nucleotide sequence encoding a secretion signal peptide is preferably a nucleotide sequence that effectively functions as a secretion signal peptide in the host cells employed in step 2. The term "secretion signal peptide" refers to a peptide comprising an amino acid sequence that acts as a recognition sequence for introducing proteins or peptides produced in the host into a pathway for secretion of the proteins or peptides to the outside of the host.

Examples of nucleotide sequences encoding a secretion signal peptide include:

(SEQ ID NO: 75)
ATGGGATTCAGCAGGATCTTTCTCTTCCTCCTGTCAGTAACTACAGG
TGTCCACTCC, (SEQ ID NO: 76)
ATGAAGTTGCCTGTTAGGCTGTTGGTGCTGCTGTTCTGGTTTCCTGC
TTCCAACACT, (SEQ ID NO: 77)
ATGGAATGGTCATGGGTCTTTCTGTTCTTTCTGAGTGTCACAACCGG
GGTGCATAGC, (SEQ ID NO: 78)
ATGGAATGGTCTTGGGTCTTTCTGTTCTTTCTGTCCGTCACTACCGG
GGTCCACTCT, (SEQ ID NO: 79)
ATGTCCGTGCCTACTCAGGTGCTGGGGCTGCTGCTGCTGTGGCTGA
CCGATGCTCGTTGC,
and (SEQ ID NO: 80)
ATGTCCGTGCCTACTCAGGTGCTGGGGCTGCTGCTGCTGTGGCTGA
CCGATGCTCGTTGT.

The vector used in step 1 comprises at least one of the above nucleic acids.

Such a vector may be one of the following vectors:

(I) a vector comprising a nucleic acid comprising a nucleotide sequence encoding at least one member selected from the group consisting of heavy chains, heavy chain variable region, and heavy chain CDRs 1 to 3 of the antibodies of the present invention;

(II) a vector comprising a nucleic acid comprising a nucleotide sequence encoding at least one member selected from the group consisting of light chains, light chain variable region, and light chain CDRs 1 to 3 of the antibodies of the present invention; or (III) a vector comprising a nucleic acid comprising a nucleotide sequence encoding at least one member selected from the group consisting of heavy chains, heavy chain variable region, and heavy chain CDRs 1 to 3 of the antibodies of the present invention, and a nucleic acid comprising a nucleotide sequence encoding at least one member selected from the group consisting of light chains, light chain variable region, and light chain CDRs 1 to 3 the antibodies of the present invention.

The above vector may be a gene expression vector. The "gene expression vector" is a vector having a function to cause expression of the nucleotide sequence of the above nucleic acid. The gene expression vector may contain a promoter sequence, enhancer sequence, repressor sequence, insulator sequence, and the like to control the expression of the nucleotide sequence. These sequences are not particularly limited insofar as they function in the above-described host.

The host used in step 1 is not particularly limited insofar as the above gene is expressed. Examples thereof include insect cells, eukaryotic cells, and mammalian cells. Of these cells, HEK cells, CHO cells, NSO cells or SP2/O cells, which are mammalian cells, are particularly preferable in terms of more efficient expression of the nucleotide sequence that encodes antibodies.

A technique for introducing the above vector into the host in step 1 is not particularly limited. A known technique may be used. The vectors shown in (I) to (III) above may be introduced singly or in a combination of two or more into the host.

A host with the above vector can be produced by such a technique. The vector may be maintained as is in the host, or in such a manner that the nucleic acid comprising the nucleotide sequence encoding antibodies in the vector is incorporated into the genome of the host. The prepared host may be maintained using a known technique, and can be stored for a long period of time, if necessary.

Step 2

Step 2 is a step of culturing the above-described host obtained in step 1 and collecting a fraction containing the antibodies of the present invention, which bind to human XCR1. Culturing the host maintaining the above-described vector allows the host to express the nucleotide sequence encoding the antibodies of the present invention based on the nucleic acid in the vector, resulting in the production of the antibodies of the present invention. The produced antibodies are stored in the host or in the medium used for culturing the host.

In step 2, a known method may be employed as a technique for collecting a fraction containing the antibodies of the present invention. For example, for collecting a fraction containing the antibodies of the present invention from the host, the host is disrupted by physical or chemical means, and the solution obtained by disruption is subjected to solid-liquid separation treatment, thereby obtaining a liquid fraction. The obtained liquid fraction may be used as the fraction containing the antibodies of the present invention.

On the other hand, for collecting a fraction containing the antibodies of the present invention from the medium used for culturing the host, the medium, i.e., the culture solution of the host obtained in step 1, is subjected to solid-liquid separation treatment, thereby obtaining a liquid fraction. The obtained liquid fraction may be used as the fraction containing the antibodies of the present invention.

In view of simplification of the isolation or purification step in the subsequent step 3, it is preferable to collect a fraction containing the antibodies of the present invention from the culture solution of the host.

The medium used for cultivation in step 2 is not particularly limited insofar as the medium allows the host to express the nucleotide sequence encoding the antibodies of the present invention, thereby producing the antibodies of the present invention. However, when collecting a fraction containing the antibodies of the present invention from the culture solution of the host as described above, it is preferable to employ serum-free medium in view of simplifying the isolation or purification step as much as possible in the subsequent step 3.

In regard to various conditions employed during cultivation of the host, such as container, temperature, time, host concentration in the medium, and culture conditions, the conditions used in a known method for producing antibodies may be employed.

Step 3

Step 3 is a step of isolating or purifying the antibodies of the present invention, which bind to human XCR1, from the fraction obtained in step 2. The method for isolating and purifying the antibodies of the present invention is not particularly limited. A generally used method for isolating or purifying protein is widely applicable.

Medicinal Use of the Antibodies of the Present Invention
(1) Use as Therapeutic Agents for Immune Diseases As described above, the antibodies of the present invention have an effect of inhibiting the phenomena of cell migration of dendritic cells associated with the immune system.

Based on this effect, the antibodies of the present invention, in particular, the humanized antibody, have potential as an active ingredient of a pharmaceutical composition that is clinically applicable to human.

Diseases to which the antibodies of the present invention are applicable are explained below.

Applicable Diseases (Immune Diseases)

XCR1 is highly expressed in CD141+ dendritic cells in the case of humans, and in CD8α+ dendritic cells in the case of mice. These dendritic cells activate T-cells using the above-described antigen presentation method called cross-presentation (Bachem A, Güttler S, Hartung E, Ebstein F, Schaefer M, Tannert A, Salama A, Movassaghi K, Opitz C, Mages H W, Henn V, Kloetzel P M, Gurka S, Kroczek R A, "Superior antigen cross-presentation and XCR1 expression define human CD11c$^+$CD141$^+$ cells as homologues of mouse CD8$^+$ dendritic cells," J Exp Med, 207: 1273-1281 (2010)).

Further, because the source of production of XCL1, which is a ligand for human XCR1, comprises T-cells, in particular, CD8+ T-cells, the chemokine system in which XCL1-XCR1 is involved controls dendritic cell-induced activation of CD8+ T-cells (Crozat K, Guiton R, Contreras V, Feuillet V, Dutertre C A, Ventre E, Vu Manh T P, Baranek T, Storset A K, Marvel J, Boudinot P, Hosmalin A, Schwartz-Cornil I, Dalod M, "The XC chemokine receptor 1 is a conserved selective marker of mammalian cells homologous to mouse CD8α+ dendritic cells," J Exp Med, 207: 1283-1292 (2010); and Dorner B G, Dorner M B, Zhou X, Opitz C, Mora A, Güttler S, Hutloff A, Mages H W, Ranke K, Schaefer M, Jack R S, Henn V, Kroczek R A, "Selective expression of the chemokine receptor XCR1 on cross-presenting dendritic cells determines cooperation with CD8+ T-cells," Immunity, 31: 823-833 (2009)).

As described above, the antibodies of the present invention include, as an embodiment, an antibody that exhibits an effect of inhibiting binding between human XCL1 and human XCR1 in dendritic cells, in particular, BDCA3+ dendritic cells. Accordingly, the antibodies of the present invention has potential as therapeutic agents for the treatment of immune diseases in which T-cells that are activated by migration of the dendritic cells are involved. In particular, the antibodies have potential as therapeutic agents for the treatment of diseases associated with the control of the activation of CD8+ T-cells.

As described above, the antibodies of the present invention include, as an embodiment, an antibody that exhibits an effect of decreasing CTL activity. CTL has a mechanism to activate the immune system by attacking cells or tissues. Various immunological diseases are known to have accelerated CTL activity; therefore, the antibodies of the present invention have potential as a therapeutic agent for the treatment of immunological diseases by decreasing CTL activity.

Non-limiting examples of such diseases include diabetes mellitus type 1, psoriasis, glomerulonephritis, autoimmune hepatitis, multiple sclerosis, ankylosing spondylitis, thyroiditis, graft rejection, delayed-type hypersensitivity, Crohn's disease, dermatomyositis, polymyositis, inclusion body myositis, rheumatoid arthritis, inflammatory bowel disease, anterior uveitis, Wegener's granulomatosis, graft-versus-host disease, and Behçet's disease (Kurts C, Robinson B W, Knolle P A, "Cross-priming in health and disease," Nat Rev Immunol, 10: 403-414 (2010); Kehren J, Desvignes C, Krasteva M, Ducluzeau M T, Assossou O, Horand F, Hahne M, Kägi D, Kaiserlian D, Nicolas J F. "Cytotoxicity is mandatory for CD8(+) T cell-mediated contact hypersensitivity," J. Exp. Med. 189: 779-786 (1999); Middel P, Thelen P, Blaschke S, Polzien F, Reich K, Blaschke V, Wrede A, Hummel K M, Gunawan B, Radzun H J, "Expression of the T-cell chemoattractant chemokine lymphotactin in Crohn's disease," Am J Pathol, 159: 1751-1761 (2001); Sugihara T, Sekine C, Nakae T, Kohyama K, Harigai M, Iwakura Y, Matsumoto Y, Miyasaka N, Kohsaka H, "A new murine model to define the critical pathologic and therapeutic mediators of polymyositis," Arthritis Rheum, 56: 1304-1314 (2007); Wang C R, Liu M F, Huang Y H, Chen H C, "Up-regulation of XCR1 expression in rheumatoid joints," Rheumatology (Oxford) 43: 569-573 (2004); Muroi E, Ogawa F, Shimizu K, Komura K, Hasegawa M, Fujimoto M, Sato S, "Elevation of serum lymphotactin levels in patients with systemic sclerosis," J Rheumatol, 35: 834-838 (2008); Torrence A E, Brabb T, Viney J L, Bielefeldt-Ohmann H, Treuting P, Seamons A, Drivdahl R, Zeng W, Maggio-Price L, "Serum biomarkers in a mouse model of bacterial-induced inflammatory bowel disease," Inflamm Bowel Dis, 14: 480-490 (2008); Yeh P T, Lin F A, Lin C P, Yang C M, Chen M S, Yang C H, "Expressions of lymphotactin and its receptor, XCR, in Lewis rats with experimental autoimmune anterior uveitis," Graefes Arch Clin Exp Ophthalmol, 248: 1737-1747 (2010); Blaschke S, Brandt P, Wessels J T, Müller G A, "Expression and function of the C-class chemokine lymphotactin (XCL1) in Wegener's granulomatosis," J Rheumatol, 36: 2491-2500 (2009); Asuka H, Okazaki Y, Kawakami Y, Hirakata M, Inoko H, Ikeda Y, Kuwana M, "Autoreactive CD8+ cytotoxic T lymphocytes to major histocompatibility complex class I chain-related gene A in patients with Behçet's disease," Arthritis Rheum, 50: 3658-3662 (2004); Serody J S, Burkett S E, Panoskaltsis-Mortari A, Ng-Cashin J, McMahon E, Matsushima G K, Lira S A, Cook D N, Blazar B R, "T-lymphocyte production of macrophage inflammatory protein-1alpha is critical to the recruitment of CD8(+) T cells to the liver, lung, and spleen during graft-versus-host disease," Blood, 96: 2973-2980 (2000); Sugihara T, Sekine C, Nakae T, Kohyama K, Harigai M, Iwakura Y, Matsumoto Y, Miyasaka N, Kohsaka H, "A new murine model to define the clinical pathologic and therapeutic mediators of polymyositis," Arthritis & Rheumatism. 56: 1304-1314 (2007)); and Dalakas M C, "Review: An update on inflammatory and autoimmune myopathies," Neuropathol Appl Neurobiol, 37: 226-242 (2011).

It was also revealed that the antibody (anti-human XCR1 mouse monoclonal antibody (5G7)) of the present invention significantly inhibits the DTH reaction in the later-described experiment that used a mouse model of delayed-type hypersensitivity (hereinafter sometimes referred to as "DTH"). As described above, delayed-type hypersensitivity is a disease known as one of the immune diseases in which CD8+ T-cells that are activated by migration of the dendritic cells are involved. The fact that the antibodies of the present invention are effective in the treatment of delayed-type hypersensitivity provides evidence that the antibodies of the present invention have activity of inhibiting cell migration, in particular, dendritic cell migration, because the antibodies of the present invention affect CD8+ T-cells.

Further, in addition to delayed-type hypersensitivity, atopic dermatitis and contact dermatitis are also known as immune diseases of the skin in which the DTH reaction is involved (Fabrizi G, Romano A, Vultaggio P, Bellegrandi S, Paganelli R, Venuti A, "Heterogeneity of atopic dermatitis defined by the immune response to inhalant and food allergy," Eur J Dermatol, 9: 380-384 (1999); and Fonacier L S, Dreskin S C, Leung D Y M, "Allergic skin diseases," J Allergy Clin Immunol, 125: S138-149 (2010)).

Based on the above, the antibodies of the present invention have potential as therapeutic agents for the treatment of immune diseases of the skin such as atopic dermatitis or contact dermatitis.

It has been pointed out that the activation of CD8+ T-cells may also be involved in the DTH reaction (Mody C H, Pain III R, Jackson C, Chen G-H, Toews G B, "CD8 Cells play a critical role in delayed-type hypersensitivity to intact *Cryptococcus neoformans*," J Immunol, 152: 3970-3979 (1994), etc.).

Invasion of CD8+ T-cells into the epidermis is observed in psoriasis, which is an autoimmune skin disease affecting a large number of patients, in particular, in chronic psoriasis lesions. These cells are considered to be the main effector cells that cause psoriasis lesions (Gudjonsson J E, Johnston A, Sigmundsdottir H, Valdimarsson H, "Immunopathogenic mechanisms in psoriasis," Clin Exp Immunol, 135: 1-8 (2004)).

Based on the above, the antibodies of the present invention have potential as therapeutic agents for the treatment of immune diseases of the skin in which the activation of CD8+ T-cells is involved.

In addition to delayed-type hypersensitivity, atopic dermatitis, and contact dermatitis, non-limiting examples of immune diseases of the skin in which CD8+ T-cells are involved also include dermatomyositis, polymyositis, inclusion body myositis, psoriasis, parapsoriasis, autoimmune blistering diseases (e.g., pemphigus, pemphigoid, and acquired epidermolysis bullosa), pustulosis, herpes gestationis, linear IgA bullous dermatosis, alopecia greata, vitiligo vulgaris, skin diseases associated with collagenosis (e.g., systemic lupus erythematosus, Sjögren syndrome, and mixed connective tissue disease), skin diseases associated with Addison's disease, skin diseases associated with graft-versus-host disease (GVHD), eczema, and urticaria.

Herein below, the relationship between the antibodies of the present invention and various immune diseases (multiple sclerosis, human type 1 diabetes mellitus, glomerulonephritis, autoimmune hepatitis, thyroiditis, graft-versus-host disease, dermatomyositis, polymyositis, and inclusion body myositis) is described. Diseases to which the antibodies of the present invention are effective are not limited to the following specific diseases.

Multiple Sclerosis

Invasion of CD8+ T-cells in addition to CD4+ T-cells into the central lesions in multiple sclerosis in humans has been recently reported. Further, it has been reported that, in the experiment using mice, implantation of CD8+ T-cells activated by antigen derived from the myelin sheath in central nerves induce experimental autoimmune encephalomeningitis, which is a model of human multiple sclerosis. Compared to the conventional model, the above-mentioned model more closely mimics the pathology of human multiple sclerosis (repeated exacerbations and remissions, significant demyelination, invasion of many CD8+ T-cells and macrophages/microglial cells in demyelinated lesions). As described above, it has been suggested that CD8+ T-cells play an important role in human multiple sclerosis and its mouse model (Friese M A, Fugger L, "Autoreactive CD8+ cells in multiple sclerosis: a new target for therapy?" Brain, 128: 1747-1763 (2005)).

Accordingly, the antibodies of the present invention that control the activation of CD8+ T-cells has potential as therapeutic agents for the treatment of multiple sclerosis.

Human Type 1 Diabetes Mellitus

Non-obese diabetic (NOD) mice representing a model of human type 1 diabetes mellitus have shown that depletion of CD8+ T-cells results in inhibition of the onset of diabetes mellitus (Wang B, Gonzales A, Benoist C, Mathis D, "The role CD8+ T-cells in the initiation of insulin-dependent diabetes mellitus," Eur J Immunol, 26: 1762-1769 (1996)). This suggests that CD8+ T-cells are also involved in the development of the pathology of diabetes mellitus type 1.

Accordingly, the antibodies of the present invention that control the activation of CD8+ T-cells has potential as therapeutic agents for the treatment of human type 1 diabetes mellitus.

Glomerulonephritis

In a mouse model of glomerulonephritis, it has been shown that CD8+ T-cells are involved in the process of the formation of renal lesions (Heymann F, Meyer-Schwesinger C, Hamilton-Williams E E, Hamerich L, Panzer W, Kaden S, Quaggin S E, Floege J, Gröne H-J, Kurts C, "Kidney dendritic cell activation is required for progression of renal disease on a mouse model of glomerular injury," J Clin Invest, 119: 1286-1297 (2009)). Invasion of many CD8+ T-cells into the kidney is observed in patients with severe autoimmune lupus nephritis. The correlation between the number of these CD8+ T-cells and an increase in the renal activity score and the serum creatinine level, which indicate aggravation of the renal function, has been reported (Couzi L, Merville P, Deminière C, Moreau J-F, Combe C, Pellegrin J-L, Viallard J-F, Blanco P, "Predominance of CD8+ T lymphocytes among periglomerular infiltrating cells and link to the prognosis of class III and class IV lupus nephritis," Arthritis Rheum, 56: 2362-2370 (2007)). As described above, CD8+ T-cells are considered to be involved in the onset of autoimmune glomerulonephritis or progression of the pathology thereof in human and mouse models.

Accordingly, the antibodies of the present invention, which control the activation of CD8+ T-cells, have potential as therapeutic agents for the treatment of glomerulonephritis.

Autoimmune Hepatitis

It has been suggested that infection with hepatitis C virus (HCV) is involved in the process of the development of autoimmune hepatitis. It has also been suggested that CD8+ CTLs induced with respect to HCV are involved in the development of autoimmune hepatitis by eliminating HCV and damaging the infected liver cells (Kammer A R, van der Burg S H, Grabscheid B, Hunziker I P, Kwappenberg K M C, Reichen J, Melief C J M, Cerny A, "Molecular mimicity of human cytochrome P450 by hepatitis C virus at the level of cytotoxic T cell recognition," J Exp Med, 190: 169-175 (1999)).

Accordingly, the antibodies of the present invention, which control the activation of CD8+ T-cells, have potential as therapeutic agents for the treatment of autoimmune hepatitis.

Thyroiditis

CD8+CTLs are known to be involved in the development of experimental autoimmune thyroiditis (EAT), which is a mouse model of human thyroiditis (for example, Hashimoto's disease). It has been reported that the mice in the model show lesions similar to human thyroiditis (antithyroglobulin antibodies are found in the peripheral blood, and the invasion of CD8+ T-cells and CD4+ T-cells into the thyroid gland is observed). As described above, it has been suggested that CD8+ T-cells are involved in the development of thyroiditis in human and mouse models (Brazillet M-P, Batteux F, Abehsira-Amar O, Nicoletti F, Charreire J, "Induction of experimental autoimmune thyroiditis by heat-denatured porcine thyroglobulin: a Tcl-mediated disease," Eur J Immunol, 29: 1342-1352 (1999)).

Accordingly, the antibodies of the present invention, which control the activation of CD8+ T-cells, have potential as therapeutic agents for the treatment of human thyroiditis.

Rheumatoid Arthritis

As described in the Examples below, 5G7, which is one of the antibodies of the present invention, exhibits a significant effect in treating rheumatoid arthritis in the experiment of DTH induced by *Mycobacterium butyricum*. Therefore, the antibodies of the present invention have potential as a therapeutic agent for the treatment of rheumatoid arthritis.

Graft Rejection

CD8+ T-cells play an important role in the graft rejection after human organ transplantation. A graft is rejected by CD8+ T-cells in the host that recognizes MHC class I being expressed in the cells in the graft. Further, invasion of many CD8+ T-cells into the kidney has been reported in renal transplant patients experiencing rejection. As described above, it has been suggested that CD8+ T-cells also play a central role in the graft rejection after human organ transplantation (Bueno V, Pestana J O M, "The role of CD8+ T-cells during allograft rejection," Braz J Med Biol Res, 35: 1247-1258 (2002)).

Accordingly, the antibodies of the present invention, which control the activation of CD8+ T-cells, have potential as therapeutic agents for the treatment of graft-versus-host disease.

Dermatomyositis, Polymyositis, and Inclusion Body Myositis

When lymphocytes that invade the lesion site of patients with dermatomyositis and polymyositis were established as cell lines, CD8+ T-cell lines showed cytotoxicity against their own cultured muscle cells. This indicates that muscle cell damage in the patients with the above-described myositis is caused by CD8+ T-cells with antigen-specific cytotoxicity (Hohlfeld R, Engel A G, "Coculture with autologous myotubes of cytotoxic T cells isolated from muscle in inflammatory myopathies," Ann Neurol, 29: 498-507 (1991)). Further, invasion of CD8+ T-cells into the lesion site has been observed in the patients with inclusion body myositis (Dalakas M C, "Review: An update on inflammatory and autoimmune myopathies," Neuropathol Appl Neurobiol, 37: 226-242 (2011)). Accordingly, the antibodies of the present invention, which control the activation of CD8+ T-cells, have potential as therapeutic agents for the treatment of dermatomyositis, polymyositis, or inclusion body myositis.

As described above, because the antibodies of the present invention have potential as therapeutic agents for the treatment of immune diseases, in particular, immune diseases of the skin, the present invention provides a pharmaceutical composition comprising the antibodies of the present invention.

Such a pharmaceutical composition has potential as a therapeutic agent for the treatment of immune disease, for the purpose of treating immune diseases, in particular, immune diseases of the skin.

The term "treatment" used herein means attainment of desired pharmacological and/or physiological effects. The effects include an effect of partially or completely curing disease and/or adverse effects caused by the disease (pathologies and symptoms). The above effects also include an effect of inhibiting or delaying the progression of the disease and/or adverse effects caused by the disease (pathologies and symptoms); an effect of alleviating pathologies and symptoms (i.e., ameliorating the disease or symptoms, or causing reversal of the progression of symptoms); and an effect of preventing recurrence of the disease. The above effects also include an effect of partially or completely preventing the onset of the disease and/or adverse effects caused by the disease (pathologies and symptoms) in the individuals who may possess a predisposition to the disease and/or adverse effects caused by the disease (pathologies and symptoms) but who have not been diagnosed as having the predisposition. Accordingly, the term "treatment" also means "relief," "prevention of recurrence," and "prevention of disease."

In the present invention, a pharmaceutical composition comprising the antibodies of the present invention can be suitably used for the treatment of human immune diseases, in particular, immune diseases of the skin. It is understood that the above pharmaceutical composition is capable of providing, for example, an effect of partially or completely curing various symptoms of immune diseases; an effect of partially or completely inhibiting various symptoms of immune diseases (i.e., inhibiting or delaying the progression); an effect of alleviating various symptoms of immune diseases (i.e., ameliorating the disease or symptoms, or causing reversal of the progression of symptoms); or an effect of preventing recurrence of various symptoms of immune diseases.

Specific examples of target diseases are as described above, with immune diseases of the skin being preferable.

The content of the antibodies of the present invention in the above pharmaceutical composition is not particularly limited insofar as the pharmaceutical composition comprises an effective amount of the antibodies of the present invention. The content can be suitably determined, for example, in such a manner the antibodies of the present invention are contained in the pharmaceutical composition in an amount of 0.001 to 99.99 wt % relative to 100 wt % of the composition, by taking into account the type of the target immune disease, dosage form, administration method, and the like.

The term "effective amount" used herein refers to an amount that allows the antibodies of the present invention to demonstrate an effect of inhibiting cell migration of dendritic cells, or an amount that allows the antibodies to demonstrate the above-described desired pharmacological and/or physiological effects (treatment effect for immune diseases).

Pharmaceutically acceptable carriers or additives may be added in combination with the antibodies of the present invention to the pharmaceutical composition. The term "pharmaceutically acceptable carriers or additives" used herein refers to optional carriers, diluents, excipients, suspending agents, lubricants, adjuvants, vehicles, delivery systems, emulsifiers, disintegrants, absorbents, preservatives, surfactants, colorants, fragrances, or sweeteners. Known carriers or additives may be used.

Non-limiting examples of dosage forms of the pharmaceutical composition include tablets, syrups, liniments, injections, and infusions, with injections or infusions being preferable. Such injections and infusions may be in aqueous, non-aqueous, or suspension form. Additionally, the pharmaceutical composition may have a dosage form that is prepared just before administration.

The pharmaceutical composition of the present invention, specifically, a therapeutic agent for an immune disease, has potential in methods of treating an immune disease, comprising a step of administering the composition to a human subject with an immune disease, in particular, an immune disease of the skin. As described above, the pharmaceutical composition also has potential in methods of preventing an immune disease, comprising administering the composition to a human subject who has not developed pathologies or symptoms of an immune disease, in particular, an immune disease of the skin, but who may possess a predisposition to the immune disease.

The dosage amount and administration method of the pharmaceutical composition (therapeutic agent for immune diseases) can be suitably determined within a range of 0.001 to 100 mg/kg/day, according to the type of immune disease, the human subject's sex, race, age, and general condition, the severity of the disease, and the like.

The antibodies of the present invention may be administered at the above-described dosage once a day, or in divided dosage several times per day. Further, in the range that the antibodies have a treatment effect on the above-described diseases, the administration interval may be every day, every other day, every week, every other week, every 2 to 3 weeks, every month, or every 2 to 3 months. Non-limiting examples of administration methods include oral, intramuscular, intravenous, intraarterial, intrathecal, intradermal, intraperitoneal, intranasal, intrapulmonary, intraocular, intravaginal, intracervical, intrarectal, and subcutaneous administrations.

(2) Application as Immunotoxin

The antibodies of the present invention may have been conjugated to cytotoxic molecules. Because such antibodies bind to human XCR1 protein that is expressed in a significant amount in dendritic cells associated with the immune system, the antibodies may be used as immunotoxins that target dendritic cells.

The term "cytotoxic molecules" used herein refers to molecules that demonstrate effects, such as apoptosis and/or necrosis, which cause the death of cells.

Examples of such molecules include saporin, ricin, *Pseudomonas* exotoxin, diphtheria toxin, and chemotherapeutic agents. Binding between the antibody and a toxic substance may be performed by a method used for the preparation of conventional immunotoxins.

(3) Other Applications of the Antibodies of the Present Invention

Because the antibodies of the present invention also include, as an embodiment, an antibody that binds to XCR1 that is expressed in a significant amount in dendritic cells, the antibodies has potential in a method for detecting dendritic cells. In this case, it is preferable to label the antibodies of the present invention for the use. The term "label" used herein refers to binding the antibodies to labeled molecules such as fluorescent molecules, luminescent molecules, chromogenic molecules and radioisotope molecules.

The binding pattern is not limited insofar as the bond is not dissociated in a detection step. A known method may be employed as a specific detection method. For example, a flow cytometry technique may be employed.

Further, the antibodies of the present invention may also be suitably applicable in methods of isolating and/or removing dendritic cells after the detection of dendritic cells. Known methods may also be employed for these methods. For example, a known cell-sorting device may be suitably used in a combination with a flow cytometry technique.

The present invention relates to the antibodies explained above, and widely encompasses the inventions of the embodiments described below.

Item 1

An antibody binding to human XCR1, wherein the antibody binds to linear or discontinuous epitopes which comprise at least three amino acids selected from the group consisting of the 8th, 11th, 12th, 13th, 14th, 16th, 17th, 22nd, 23rd, 176th, and 177th amino acids in the amino acid sequence of SEQ ID NO: 91.

Item 2

The antibody according to above item 1, wherein the antibody is:

the antibody comprising a heavy chain variable region comprising heavy chain CDRs 1 to 3 described in (g) to (i) below and a light chain variable region comprising light chain CDRs 1 to 3 described in (j) to (1) below;

the antibody comprising a heavy chain variable region comprising heavy chain CDRs 1 to 3 described in (m) to (O) below and a light chain variable region comprising light chain CDRs 1 to 3 described in (p) to (r) below; or the antibody comprising a heavy chain variable region comprising heavy chain CDRs 1 to 3 described in (a) to (c) below and a light chain variable region comprising light chain CDRs 1 to 3 described in (d) to (f) below:

(a) a heavy chain CDR 1 consisting of the amino acid sequence of SEQ ID NO: 41,
(b) a heavy chain CDR 2 consisting of the amino acid sequence of SEQ ID NO: 42,
(c) a heavy chain CDR 3 consisting of the amino acid sequence of SEQ ID NO: 43;
(d) a light chain CDR 1 consisting of the amino acid sequence of SEQ ID NO: 44,
(e) a light chain CDR 2 consisting of the amino acid sequence of SEQ ID NO: 45, and
(f) a light chain CDR 3 consisting of the amino acid sequence of SEQ ID NO: 46;
(g) a heavy chain CDR 1 consisting of the amino acid sequence of SEQ ID NO: 17,
(h) a heavy chain CDR 2 consisting of the amino acid sequence of SEQ ID NO: 18,
(i) a heavy chain CDR 3 consisting of the amino acid sequence of SEQ ID NO: 19;
(j) a light chain CDR 1 consisting of the amino acid sequence of SEQ ID NO: 20,
(k) a light chain CDR 2 consisting of the amino acid sequence of SEQ ID NO: 21,
(l) a light chain CDR 3 consisting of the amino acid sequence of SEQ ID NO: 22;
(m) a heavy chain CDR 1 consisting of the amino acid sequence of SEQ ID NO: 29,
(n) a heavy chain CDR 2 consisting of the amino acid sequence of SEQ ID NO: 30,
(o) a heavy chain CDR 3 consisting of the amino acid sequence of SEQ ID NO: 31;
(p) a light chain CDR 1 consisting of the amino acid sequence of SEQ ID NO: 32,
(q) a light chain CDR 2 consisting of the amino acid sequence of SEQ ID NO: 33, and
(r) a light chain CDR 3 consisting of the amino acid sequence of SEQ ID NO: 34.

Item 3

The antibody according to above item 1 or 2, wherein the antibody comprises a heavy chain variable region comprising an amino acid sequence of SEQ ID NO: 60 or 64, and a light chain variable region comprising an amino acid sequence of SEQ ID NO: 68 or 72.

Item 4

The antibody according to any one of above items 1 to 3, wherein the antibody comprises a heavy chain variable region comprising an amino acid sequence of SEQ ID NO: 60, and a light chain variable region comprising an amino acid sequence of SEQ ID NO: 68.

Item 5

The antibody according to any one of above items 1 to 3, wherein the antibody comprises a heavy chain variable region comprising an amino acid sequence of SEQ ID NO: 64, and a light chain variable region comprising an amino acid sequence of SEQ ID NO: 72.

Item 6

The antibody according to any one of above items 1 to 5, wherein the antibody comprises a human constant region.

Item 7

The antibody according to any one of above items 1 to 6, wherein the antibody comprises a heavy chain comprising an amino acid sequence of SEQ ID NO: 59, and a light chain comprising an amino acid sequence of SEQ ID NO: 67.

Item 8

The antibody according to any one of above items 1 to 6, wherein the antibody comprises a heavy chain comprising an amino acid sequence of SEQ ID NO: 63, and a light chain comprising an amino acid sequence of SEQ ID NO: 71.

Item 9

The antibody according to any one of above items 1 to 8 comprising an Fc region, wherein the Fc region is mutated to induce a change in ADCC activity.

Item 10

The antibody according to above item 9, wherein the Fc region is mutated to lower ADCC activity.

Item 11

The antibody according to any one of above items 1 to 10, wherein the antibody is conjugated to a cytotoxic molecule.

Item 12

The antibody according to any one of above items 1 to 11, wherein the antibody inhibits interaction between human XCR1 and human XCL1.

Item 13

The antibody according to any one of above items 1 to 12, wherein the antibody inhibits cell migration of dendritic cells.

Item 14

The antibody according to any one of above items 1 to 13, wherein the antibody suppresses the activity of cytotoxic T lymphocytes.

Item 15

A pharmaceutical composition comprising the antibody according to any one of above items 1 to 14 and a pharmaceutically acceptable carrier or additive.

Item 16

The pharmaceutical composition according to above item 15, wherein the pharmaceutical composition is a therapeutic agent for an immune disease.

Item 17

The pharmaceutical composition according to above item 16, wherein the immune disease is an immune disease of the skin.

Item 18

The pharmaceutical composition according to above item 17, wherein the immune disease of the skin is psoriasis, parapsoriasis, atopic dermatitis, contact dermatitis, dermatomyositis, polymyositis, inclusion body myositis, autoimmune blistering disease (pemphigus, pemphigoid, or acquired epidermolysis bullosa), pustulosis, herpes gestationis, linear IgA bullous dermatosis, alopecia greata, vitiligo vulgaris, skin disease associated with collagenosis (systemic lupus erythematosus, Sjögren syndrome, or mixed connective tissue disease), skin disease associated with Addison's disease, skin disease associated with graft-versus-host disease (GVHD), eczema, or urticaria.

Item 19

The pharmaceutical composition according to above item 17, wherein the immune disease of the skin is psoriasis, atopic dermatitis, contact dermatitis, dermatomyositis, polymyositis, or inclusion body myositis.

Item 20

The pharmaceutical composition according to above item 17, wherein the immune disease of the skin is atopic dermatitis or contact dermatitis.

Item 21

The pharmaceutical composition according to above item 16, wherein the immune disease is thyroiditis, rheumatoid arthritis, type 1 diabetes, or multiple sclerosis.

Item 22

A nucleic acid comprising a nucleotide sequence encoding the antibody according to any one of above items 1 to 14.

Item 23

A method of treating an immune disease comprising administering an effective amount of the antibody according to any one of above items 1 to 14 or the pharmaceutical composition according to above item 15 to a human affected by an immune disease.

Item 24

The method according to above item 23, wherein the immune disease is an immune disease of the skin.

Item 25

The method according to above item 24, wherein the immune disease of the skin is psoriasis, parapsoriasis, atopic dermatitis, contact dermatitis, dermatomyositis, polymyositis, inclusion body myositis, autoimmune blistering disease (pemphigus, pemphigoid, or acquired epidermolysis bullosa), pustulosis, herpes gestationis, linear IgA bullous dermatosis, alopecia greata, vitiligo vulgaris, skin disease associated with collagenosis (systemic lupus erythematosus, Sjögren syndrome, or mixed connective tissue disease), skin disease associated with Addison's disease, skin disease associated with graft-versus-host disease (GVHD), eczema, or urticaria.

Item 26

The method according to above item 24, wherein the immune disease of the skin is psoriasis, atopic dermatitis, contact dermatitis, dermatomyositis, polymyositis, or inclusion body myositis.

Item 27

The method according to above item 23, wherein the immune disease is thyroiditis, rheumatoid arthritis, type 1 diabetes, or multiple sclerosis.

The present invention also encompasses the embodiments described below

Item 1-A

An antibody comprising a heavy chain variable region comprising heavy chain CDRs 1 to 3 described in (g) to (i) below and a light chain variable region comprising light chain CDRs 1 to 3 described in (j) to (1) below;

an antibody comprising a heavy chain variable region comprising heavy chain CDRs 1 to 3 described in (m) to (O) below and a light chain variable region comprising light chain CDRs 1 to 3 described in (p) to (r) below; or an antibody comprising a heavy chain variable region comprising heavy chain CDRs 1 to 3 described in (a) to (c) below and a light chain variable region comprising light chain CDRs 1 to 3 described in (d) to (f) below:

(a) a heavy chain CDR 1 consisting of the amino acid sequence of SEQ ID NO: 41, (b) a heavy chain CDR 2 consisting of the amino acid sequence of SEQ ID NO: 42, (c) a heavy chain CDR 3 consisting of the amino acid sequence of SEQ ID NO: 43;

(d) a light chain CDR 1 consisting of the amino acid sequence of SEQ ID NO: 44, (e) a light chain CDR 2 consisting of the amino acid sequence of SEQ ID NO: 45, and (f) a light chain CDR 3 consisting of the amino acid sequence of SEQ ID NO: 46;
(g) a heavy chain CDR 1 consisting of the amino acid sequence of SEQ ID NO: 17,
(h) a heavy chain CDR 2 consisting of the amino acid sequence of SEQ ID NO: 18,
(i) a heavy chain CDR 3 consisting of the amino acid sequence of SEQ ID NO: 19;
(j) a light chain CDR 1 consisting of the amino acid sequence of SEQ ID NO: 20,
(k) a light chain CDR 2 consisting of the amino acid sequence of SEQ ID NO: 21,
(l) a light chain CDR 3 consisting of the amino acid sequence of SEQ ID NO: 22;
(m) a heavy chain CDR 1 consisting of the amino acid sequence of SEQ ID NO: 29,
(n) a heavy chain CDR 2 consisting of the amino acid sequence of SEQ ID NO: 30,
(o) a heavy chain CDR 3 consisting of the amino acid sequence of SEQ ID NO: 31;
(p) a light chain CDR 1 consisting of the amino acid sequence of SEQ ID NO: 32,
(q) a light chain CDR 2 consisting of the amino acid sequence of SEQ ID NO: 33, and
(r) a light chain CDR 3 consisting of the amino acid sequence of SEQ ID NO: 34.

Item 2-A
The antibody according to above item 1-A, comprising a heavy chain variable region comprising an amino acid sequence of SEQ ID NO: 60 or 64, and a light chain variable region comprising an amino acid sequence of SEQ ID NO: 68 or 72.

Item 3-A
The antibody according to above item 1-A or 2-A, comprising a heavy chain variable region comprising an amino acid sequence of SEQ ID NO: 60, and a light chain variable region comprising an amino acid sequence of SEQ ID NO: 68.

Item 4-A
The antibody according to above item 1-A or 2-A, comprising a heavy chain variable region comprising an amino acid sequence of SEQ ID NO: 64, and a light chain variable region comprising an amino acid sequence of SEQ ID NO: 72.

Item 5-A
The antibody according to any one of above items 1-A to 4-A, comprising a human constant region.

Item 6-A
The antibody according to any one of above items 1-A to 5-A, comprising a heavy chain comprising an amino acid sequence of SEQ ID NO: 59, and a light chain comprising an amino acid sequence of SEQ ID NO: 67.

Item 7-A
The antibody according to any one of above items 1-A to 5-A, comprising a heavy chain comprising an amino acid sequence of SEQ ID NO: 63, and a light chain comprising an amino acid sequence of SEQ ID NO: 71.

Item 8-A
The antibody according to any one of above items 1-A to 7-A comprising an Fc region, wherein the Fc region is mutated to induce a change in ADCC activity.

Item 9-A
The antibody according to above item 8-A, wherein the Fc region is mutated to lower ADCC activity.

Item 10-A
The antibody according to any one of above items 1-A to 9-A, wherein the antibody inhibits interaction between human XCR1 and human XCL1.

Item 11-A
The antibody according to any one of above items 1-A to 10-A, wherein the antibody inhibits cell migration of dendritic cells.

Item 12-A
A pharmaceutical composition comprising the antibody according to any one of above items 1-A to II-A and a pharmaceutically acceptable carrier or additive.

Item 13-A
The pharmaceutical composition according to above item 12-A, wherein the pharmaceutical composition is a therapeutic agent for an immune disease.

Item 14-A
The pharmaceutical composition according to above item 13-A, wherein the immune disease is an immune disease of the skin.

Item 15-A
The pharmaceutical composition according to above item 14-A, wherein the immune disease of the skin is psoriasis, parapsoriasis, atopic dermatitis, contact dermatitis, dermatomyositis, polymyositis, inclusion body myositis, autoimmune blistering disease (pemphigus, pemphigoid, or acquired epidermolysis bullosa), pustulosis, herpes gestationis, linear IgA bullous dermatosis, alopecia greata, vitiligo vulgaris, skin disease associated with collagenosis (systemic lupus erythematosus, Sjögren syndrome, or mixed connective tissue disease), skin disease associated with Addison's disease, skin disease associated with graft-versus-host disease (GVHD), eczema, or urticaria.

Item 16-A
The pharmaceutical composition according to above item 14-A, wherein the immune disease of the skin is psoriasis, atopic dermatitis, contact dermatitis, dermatomyositis, polymyositis, or inclusion body myositis.

Item 17-A
The pharmaceutical composition according to above item 14-A, wherein the immune disease of the skin is atopic dermatitis or contact dermatitis.

Item 18-A
A nucleic acid comprising a nucleotide sequence encoding the antibody according to any one of above items 1-A to II-A.

Item 19-A
An immune disease treatment method comprising a step of administering an effective amount of the antibody according to any one of above items 1-A to II-A to a human affected by an immune disease.

The present invention further encompasses the embodiments described below.

Item 1-B
An antibody comprising a heavy chain variable region comprising heavy chain CDRs 1 to 3 described in (g) to (i) below and a light chain variable region comprising light chain CDRs 1 to 3 described in (j) to (l) below;
an antibody comprising a heavy chain variable region comprising heavy chain CDRs 1 to 3 described in (m) to (O) below and a light chain variable region comprising light chain CDRs 1 to 3 described in (p) to (r) below; or
an antibody comprising a heavy chain variable region comprising heavy chain CDRs 1 to 3 described in (a) to (c) below and a light chain variable region comprising light chain CDRs 1 to 3 described in (d) to (f) below:
(a) a heavy chain CDR 1 consisting of the amino acid sequence of SEQ ID NO: 41, (b) a heavy chain CDR 2 consisting of the amino acid sequence of SEQ ID NO: 42,
(c) a heavy chain CDR 3 consisting of the amino acid sequence of SEQ ID NO: 43;
(d) a light chain CDR 1 consisting of the amino acid sequence of SEQ ID NO: 44,
(e) a light chain CDR 2 consisting of the amino acid sequence of SEQ ID NO: 45, and
(f) a light chain CDR 3 consisting of the amino acid sequence of SEQ ID NO: 46;
(g) a heavy chain CDR 1 consisting of the amino acid sequence of SEQ ID NO: 17,
(h) a heavy chain CDR 2 consisting of the amino acid sequence of SEQ ID NO: 18,
(i) a heavy chain CDR 3 consisting of the amino acid sequence of SEQ ID NO: 19;
(j) a light chain CDR 1 consisting of the amino acid sequence of SEQ ID NO: 20,
(k) a light chain CDR 2 consisting of the amino acid sequence of SEQ ID NO: 21,
(l) a light chain CDR 3 consisting of the amino acid sequence of SEQ ID NO: 22;
(m) a heavy chain CDR 1 consisting of the amino acid sequence of SEQ ID NO: 29,
(n) a heavy chain CDR 2 consisting of the amino acid sequence of SEQ ID NO: 30,
(o) a heavy chain CDR 3 consisting of the amino acid sequence of SEQ ID NO: 31;
(p) a light chain CDR 1 consisting of the amino acid sequence of SEQ ID NO: 32,
(q) a light chain CDR 2 consisting of the amino acid sequence of SEQ ID NO: 33, and
(r) a light chain CDR 3 consisting of the amino acid sequence of SEQ ID NO: 34.

Item 2-B
The antibody according to above item 1-B, comprising a heavy chain variable region comprising an amino acid sequence of SEQ ID NO: 60 or 64, and a light chain variable region comprising an amino acid sequence of SEQ ID NO: 68 or 72.

Item 3-B
The antibody according to above item 1-B or 2-B, comprising a heavy chain variable region comprising an amino acid sequence of SEQ ID NO: 60, and a light chain variable region comprising an amino acid sequence of SEQ ID NO: 68.

Item 4-B
The antibody according to above item 1-B or 2-B, comprising a heavy chain variable region comprising an amino acid sequence of SEQ ID NO: 64, and a light chain variable region comprising an amino acid sequence of SEQ ID NO: 72.

Item 5-B
The antibody according to any one of above items 1-B to 4-B, comprising a human constant region.

Item 6-B
The antibody according to any one of above items 1-B to 5-B, comprising a heavy chain comprising an amino acid sequence of SEQ ID NO: 59, and a light chain comprising an amino acid sequence of SEQ ID NO: 67.

Item 7-B
The antibody according to any one of above items 1-B to 5-B, comprising a heavy chain comprising an amino acid sequence of SEQ ID NO: 63, and a light chain comprising an amino acid sequence of SEQ ID NO: 71.

Item 8-B
The antibody according to any one of above items 1-B to 7-B comprising an Fc region, wherein the Fc region is mutated to induce a change in ADCC activity.

Item 9-B
The antibody according to above item 8-B, wherein the Fc region is mutated to lower ADCC activity.

Item 10-B
The antibody according to any one of above items 1-B to 9-B, wherein the antibody is conjugated to a cytotoxic molecule.

Item 11-B
The antibody according to any one of above items 1-B to 10-B, wherein the antibody inhibits interaction between human XCR1 and human XCL1.

Item 12-B
The antibody according to any one of above items 1-B to 11-B, wherein the antibody inhibits cell migration of dendritic cells.

Item 13-B
A pharmaceutical composition comprising the antibody according to any one of above items 1-B to 12-B and a pharmaceutically acceptable carrier or additive.

Item 14-B
The pharmaceutical composition according to above item 13-B, wherein the pharmaceutical composition is a therapeutic agent for an immune disease.

Item 15-B
The pharmaceutical composition according to above item 14-B, wherein the immune disease is an immune disease of the skin.

Item 16-B
The pharmaceutical composition according to above item 15-B, wherein the immune disease of the skin is psoriasis, parapsoriasis, atopic dermatitis, contact dermatitis, dermatomyositis, polymyositis, inclusion body myositis, autoimmune blistering disease (pemphigus, pemphigoid, or acquired epidermolysis bullosa), pustulosis, herpes gestationis, linear IgA bullous dermatosis, alopecia greata, vitiligo vulgaris, skin disease associated with collagenosis (systemic lupus erythematosus, Sjögren syndrome, or mixed connective tissue disease), skin disease associated with Addison's disease, skin disease associated with graft-versus-host disease (GVHD), eczema, or urticaria.

Item 17-B
The pharmaceutical composition according to above item 15-B, wherein the immune disease of the skin is psoriasis, atopic dermatitis, contact dermatitis, dermatomyositis, polymyositis, or inclusion body myositis.

Item 18-B
The pharmaceutical composition according to above item 15-B, wherein the immune disease of the skin is atopic dermatitis or contact dermatitis.

Item 19-B
A nucleic acid comprising a nucleotide sequence encoding the antibody according to any one of above items 1-B to 12-B.

Item 20-B
A method of treating an immune disease comprising administering an effective amount of the antibody according to any one of above items 1-B to 12-B or the pharmaceutical composition according to above item 13-B to a human affected by an immune disease.

Item 21-B
The method according to above item 20-B, wherein the immune disease is an immune disease of the skin.

Item 22-B
The method according to above item 21-B, wherein the immune disease of the skin is psoriasis, parapsoriasis, atopic dermatitis, contact dermatitis, dermatomyositis, polymyositis, inclusion body myositis, autoimmune blistering disease (pemphigus, pemphigoid, or acquired epidermolysis bullosa), pustulosis, herpes gestationis, linear IgA bullous dermatosis, alopecia greata, vitiligo vulgaris, skin disease associated with collagenosis (systemic lupus erythematosus, Sjögren syndrome, or mixed connective tissue disease), skin disease associated with Addison's disease, skin disease associated with graft-versus-host disease (GVHD), eczema, or urticaria.

Item 23-B

The method according to above item 21-B, wherein the Immune disease of the skin is psoriasis, atopic dermatitis, contact dermatitis, dermatomyositis, polymyositis, or inclusion body myositis.

Item 24-B

The method according to above item 21-B, wherein the immune disease of the skin is atopic dermatitis or contact dermatitis.

EXAMPLES

Herein below, the present invention is described in more detail based on Examples. Needless to say, the present invention is not limited to the Examples.

Example 1

(1) Preparation of Mouse Anti-Human XCR1 Monoclonal Antibodies

To obtain monoclonal antibodies against human XCR1, membrane fraction of human XCR1-expressing B300.19 cells was immunized to XCR1 knockout mice. The membrane fraction was prepared as the following procedure: first, human XCR1-expressing B300.19 cells, being suspended in a Ho buffer (0.25 M Sucrose, 10 mM Hepes (pH 7.4), 1 mM EGTA, 0.5 mM $MgCl_2$, 1× Complete mini EDTA-free (Roche Applied Science)), were disrupted (800 psi, for 30 minutes on ice) by a nitrogen gas cell disruption vessel (Parr Instrument Company) and then centrifuged (2,000 g, 10 minutes). The supernatant was collected and re-centrifuged (100,000 g, 30 minutes). The pellet was suspended in a 50 mM Hepes (pH 7.4) buffer, and designated as a membrane fraction.

160 µg or 260 µg of this membrane fraction was mixed with equal volume of GERBU adjuvant (GERBU Biotechnik GmbH), and then injected subcutaneously into the footpads of the XCR1 knockout mice (Deltagen). Five or six additional injections were then administered every other week. Three or four days after the final immunization, the mice were sacrificed, and the peripheral lymph-node cells were fused with P3U1 myeloma cells at a 2:1 or 5:1 ratio in the presence of GenomeONE-CF (Ishihara Sangyo Kaisha, Ltd.). The fused cells were then cultured in 96-well plastic plates.

FACS analysis was performed for primary screening. Parent CHO cells and human XCR1-EGFP-expressing CHO cells were mixed at a 1:1 ratio, and suspended in a FACS buffer (1 mM EDTA, 1% FBS-containing PBS (Sigma)). The cells were incubated for 20 minutes on ice with culture supernatants from each hybridoma. The cells were washed with the FACS buffer three times, and then incubated for 20 minutes on ice with PE-labeled anti-mouse IgG polyclonal antibody (Jackson, #715-116-151, diluted at 1:100 in the FACS buffer). The cells were washed with the FACS buffer three times, and then suspended in the FACS buffer. The fluorescence intensity was measured using a FACSCanto II Cell analyzer (BD Bioscience). As results, supernatants collected from three wells showed high reactivity to human XCR1-EGFP-expressing CHO cells.

A standard limiting dilution method was used to obtain clones from these three positive wells (2H6, 5G7, and 11H2). The reactivity of each clone was confirmed by the FACS analysis described above.

Subsequently, an in vitro chemotaxis assay was performed to evaluate the neutralizing activity of these three clones on human lymphotactin-induced migration of human XCR1-expressing BaF3 cells or B300.19 cells. The chemotaxis assay was performed in 24-well transwell culture supports (pore 3 µm, Costar, #3399) or 96-well transwell culture plates (MultiScreen, pore 5 µm, Millipore, #MAMIC 5S10).

In the case of the 24-well transwell culture supports, human XCR1-expressing BaF3 cells ($1×10^6$ cells) were suspended in a mixture of 50 µL of a chemotaxis buffer (RPMI1 640 medium (Invitrogen) containing 0.5% BSA, 0.5% FBS, and 20 mM HEPES (pH 7.4)) and 50 µL of each culture supernatant, and incubated at room temperature for 30 minutes. Subsequently, recombinant human lymphotactin (Genzyme, #2695) dissolved in the chemotaxis buffer at a concentration of 1 µg/mL was added to the lower wells at 600 µL/well, and the incubated cells were added to the upper wells. After 4 hours of incubation in a 5% $CO_2$ incubator at 37° C., the transwells were centrifuged at 1,350 rpm for 5 minutes, and migrated cells were collected into the lower wells. The collected cells were fixed with paraformaldehyde (final concentration: 1%), and 30 µL of each sample was applied to the FACSCanto II cell analyzer to count the number of the cells.

In the case of the 96-well transwell culture plates, human XCR1-expressing B300.19 cells ($2×10^5$ cells) were suspended in a mixture of 25 µL of a chemotaxis buffer (RPMI1 640 (Invitrogen) containing 0.5% BSA, 0.5% FBS, and 20 mM HEPES (pH 7.4), and 50 µM 2-mercaptoethanol) and 50 µL of each culture supernatant, and incubated at room temperature for 30 minutes. Subsequently, recombinant human lymphotactin (Genzyme, #2695) dissolved in chemotaxis buffer at a concentration of 1 µg/mL was added to the lower wells at 150 µL/well, and the incubated cells were added to the upper wells. After 4 hours of incubation in a 5% $CO_2$ incubator at 37° C., the transwells were centrifuged at 1,350 rpm for 5 minutes, and migrated cells were collected in the lower wells. 30 µL of each sample was applied to the FACSCanto II cell analyzer to count the number of the cells.

The culture supernatants produced by three hybridoma clones (2H6, 5G7, and 11H2) demonstrated neutralizing activity against human lymphotactin-induced migration of human XCR1-expressing BaF3 cells and B300.19 cells.

(2) Reactivity of Mouse Anti-Human XCR1 Antibodies (2H6, 5G7, and 11H2) to Human XCR1-Expressing Cells In order to evaluate the reactivity and neutralizing activity of purified antibodies from these three clones, the antibodies were purified with recombinant protein A (GE Healthcare, #17-5080-01) from culture supernatants of each clone. The isotype of each clone was determined using monoclonal antibody isotyping kit (Serotec, #MMT1). 2H6 and 5G7 were IgG2b, K and 11H2 was IgG2a, K.

The reactivity of the purified antibodies to human XCR1 was evaluated by FACS analysis. Parent B300.19 cells and human XCR1-EGFP-expressing B300.19 cells were mixed at a 1:1 ratio and suspended in a FACS buffer (1% FBS-containing PBS⁻ (Sigma)). The cells were blocked for 10 minutes on ice with the FACS buffer containing 100 μg/mL of human immunoglobulin. The cells were then incubated for 20 minutes on ice with the purified antibodies (2H6, 5G7, and 11H2) at various concentrations from 0 to 10 μg/mL or with mouse isotype control antibody, IgG2a (eBioscience, #14-4724-82) or IgG2b (eBioscience, #14-4732-82), at a concentration of 10 μg/mL. The cells were washed with the FACS buffer three times, and then incubated for 20 minutes on ice with PE-labeled anti-mouse IgG polyclonal antibody (Jackson, #715-116-151, diluted at 1:50 in the FACS buffer). The cells were washed with the FACS buffer three times, and then suspended in the FACS buffer. The fluorescence intensity was measured by a FACSCanto II cell analyzer.

These three purified antibodies (2H6, 5G7, and 11H2) showed the reactivity to human XCR1-EGFP-expressing B300.19 cells, but not to parent B300.19 cells (FIG. 1). In contrast, the mouse isotype control antibody did not react to either human XCR1-EGFP-expressing B300.19 cells, or to parent cells (data not shown).

Figure 2:
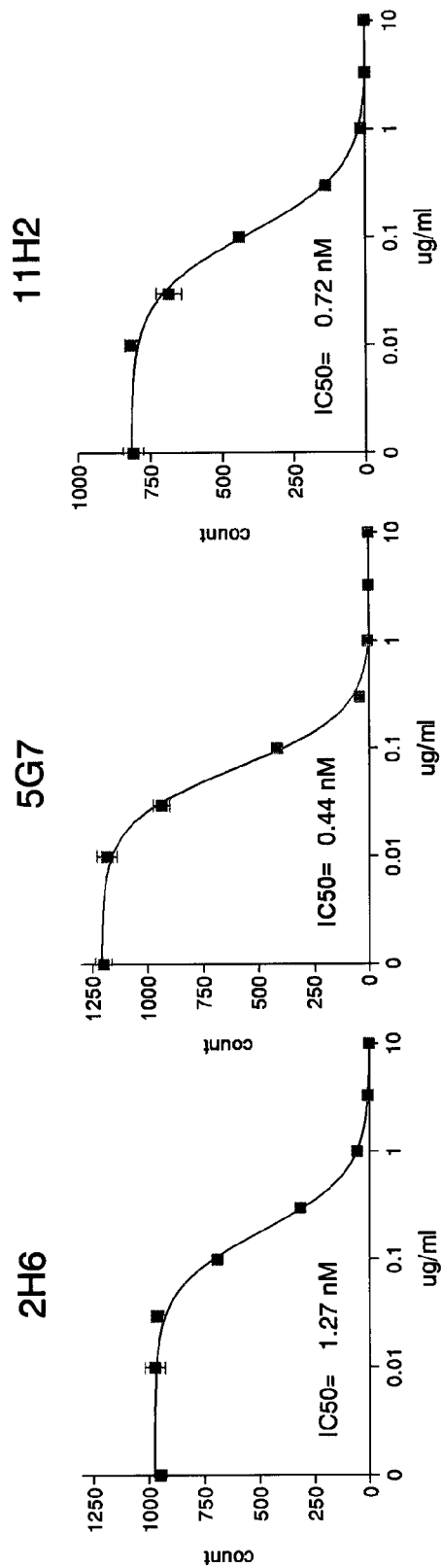
FIG. 2 shows the analysis results of a chemotaxis assay of the neutralizing activity of the mouse anti-human XCR1 antibodies (2H6, 5G7, and 11H2) on human lymphotactin-induced migration of human XCR1-EGFP-expressing B300.19 cells.

(3) Neutralizing Activity of Mouse Anti-Human XCR1 Antibodies (2H6, 5G7, and 11H2) against Human Lymphotactin-Induced Migration of Human XCR1-Expressing Cells The neutralizing activity of purified antibodies from these clones was evaluated by in vitro chemotaxis assay. The chemotaxis assay was performed using 96-well transwell culture plates (MultiScreen, pore 5 μm, Millipore, #MAMIC 5S10). Human XCR1-expressing B300.19 cells ($2 \times 10^5$ cells) were suspended in a 75 μL of chemotaxis buffer (RPMI 1640 medium (Invitrogen) containing 0.5% BSA, 0.5% FBS, 20 mM HEPES (pH 7.4), and 50 μM 2-mercaptoethanol) containing each of the purified antibodies (2H6, 5G7, and 11H2) at various concentrations from 0 to 10 μg/mL; and incubated at room temperature for 30 minutes. Further, recombinant human lymphotactin (R&D, #695-LT/CF) was dissolved in the chemotaxis buffer at a final concentration of 1 μg/mL, in which the purified antibodies were dissolved at various concentrations from 0 to 10 μg/mL. The mixture of lymphotactin and purified antibodies were added to the lower wells at 150 μL/well, and incubated at room temperature for 30 minutes. 30 minutes later, the incubated cells were added to the upper wells, and incubated in a 5% $CO_2$ incubator at 37° C. for 4 hours. Subsequently, 30 μL of each sample was applied to the FACSCanto II cell analyzer to count the number of the cells. 2H6, 5G7, and 11H2 mAbs completely inhibited cell migration at a concentration of about 3 μg/mL. FIG. 2 shows the typical pattern of the concentration-dependent inhibition. $IC_{50}$ and $IC_{90}$ values were calculated from three independent experiments. Table 1 shows these values as the mean±standard error.

TABLE 1

$IC_{50}$ and $IC_{90}$ Values of 2H6, 5G7, and 11H2 by Chemotaxis Assay

|  | 2H6 | 5G7 | 11H2 |
|---|---|---|---|
| $IC_{50}$ (nM) | 1.28 ± 0.172 | 0.63 ± 0.139 | 0.99 ± 0.168 |
| $IC_{90}$ (nM) | 7.60 ± 2.331 | 2.52 ± 0.645 | 6.32 ± 1.830 |

(4) Sequence Analysis of Mouse Anti-Human XCR1 Antibodies (2H6, 5G7, and 11H2)

A polynucleotide comprising a gene sequence encoding the heavy and light chains of the clones (2H6, 5G7, and 11H2) were amplified by 5'-RACE (5'-rapid amplification of cDNA ends) method. The total RNA was prepared from the hybridoma of these three clones using TRIZOL (Invitrogen) and treated with DNase (QIAGEN, RNase free DNase set). Double-stranded cDNA was prepared from the total RNA, using a cDNA synthesis kit (TAKARA). 5' adaptor obtained by annealing ad29S; ACATCACTCCGT (SEQ ID NO: 81) and as29AS; ACGGAGTGATGTCCGTCGACGTATCTCT-GCGTTGATACTTCAGCGTAGCT (SEQ ID NO: 82) was added to the cDNA. The obtained cDNA was amplified using 5' forward primer
(5'-PCR4 primer, AGCTACGCTGAAGTATCAACGCA-GAG: SEQ ID NO: 83) and
3' reverse primer
(AGGACAGGGGTTGATTGTTGA: SEQ ID NO: 84, or CTCAAGTTTTTTGTCCACCGTGGTGC: SEQ ID NO: 85 was used to amplify IgG2b heavy chain; CTCAATTTTCTTGTCCACCTTGGTGC: SEQ ID NO: 86, or GCCAGTGGATAGACTGATG: SEQ ID NO: 87 was used to amplify IgG2a heavy chain; and CTCATTCCT-GTTGAAGCTCTTGACAAT: SEQ ID NO: 88, GATGGATACAGTTGGTGCAGC: SEQ ID NO: 89, or CAGATCCTCAGCCTCCACTCTGCT: SEQ ID NO: 90 was used to amplify IGκ light chain). The amplified cDNA was inserted into pCR2.1 vector (Invitrogen). The gene sequences were analyzed using ABI3130XL. Tables 2-1 to 4-2 show amino acid sequences encoded by the gene sequences identified by the analysis.

TABLE 2-1

Amino Acid Sequences of Mouse Anti-Human XCR1 Antibody (2H6)

| Name | Sequence |
|---|---|
| Heavy chain variable region (SEQ ID NO: 1) | QAYLQQSGAELVRPGASVKMSCKASGYTFSSHNMHWIKQTLRQGLE WIGAIYPGKGNTSYNQKFKGKATLTVDKSSSTAYMQLSSLTSEDSA VYFCARWGSVVGDWYFDVWGTGTTVTVSS |
| Light chain variable region (SEQ ID NO: 2) | DVVVTQTPLSLPVSLGDQASISCRSSQSLVHSNGNTYLHWYLQKPG QSPKLLIYRVSNRFSGVPDRFSGSGLGRDFTLKISRVEAEDLGVYF CSQSTFVPWTFGGGTKLEIK |

TABLE 2-2

Nucleic Acid Sequences of Mouse Anti-Human XCR1 Antibody (2H6)

| Name | Sequence |
|---|---|
| Heavy chain variable region (SEQ ID NO: 3) | CAGGCTTATCTACAGCAGTCTGGGGCTGAACTGGTGAGGCCTGGGG CCTCAGTGAAGATGTCCTGCAAGGCTTCTGGCTACACATTTAGCAG TCACAATATGCACTGGATAAAGCAGACACTTAGACAGGGCCTGGAA TGGATAGGAGCTATTTATCCAGGAAAAGGTAATACTTCCTACAATC AGAAGTTCAAGGGCAAGGCCACACTGACTGTAGACAAATCCTCCAG CACAGCCTACATGCAGCTCAGCAGCCTGACATCTGAAGACTCTGCG GTCTATTTCTGTGCAAGATGGGGTTCGGTAGTAGGAGACTGGTACT TCGATGTCTGGGGCACAGGGACCACGGTCACCGTCTCTTCA |
| Light chain variable region (SEQ ID NO: 4) | GATGTTGTGGTGACCCAAACTCCACTCTCCCTGCCTGTCAGTCTTG GAGATCAAGCCTCCATCTCTTGCAGATCTAGTCAGAGCCTTGTACA CAGTAATGGAAACACCTATTTACATTGGTACCTGCAGAAGCCAGGC CAGTCTCCAAAGCTCCTGATCTACAGAGTTTCCAATCGATTTTCTG GGGTCCCAGACAGGTTCAGTGGCAGTGGATTAGGGAGAGATTTCAC ACTCAAGATCAGCAGAGTGGAGGCTGAGGATCTGGGAGTTTATTTC TGCTCTCAAAGTACATTTGTTCCGTGGACGTTCGGTGGAGGCACCA AGCTGGAAATCAAA |

TABLE 3-1

Amino Acid Sequences of Mouse Anti-Human XCR1 Antibody (5G7)

| Name | Sequence |
|---|---|
| Heavy chain variable region (SEQ ID NO: 5) | QAYLQQSGAELVRPGASVKMSCKASGYTFTSHNLHWVKQTPRQGLQ WIGAIYPGNGNTAYNQKFKGKATLTVDKSSSTAYMQLSSLTSDDSA VYFCARWGSVVGDWYFDVWGTGTTVTVSS |
| Light chain variable region (SEQ ID NO: 6) | DVVMTQTPLSLPVTLGNQASIFCRSSLGLVHRNGNTYLHWYLQKPG QSPKLLIYKVSHRFSGVPDRFSGSGSGTDFTLKISRVEAEDLGVYF CSQSTHVPWTFGGGTKLEIK |

TABLE 3-2

Nucleic Acid Sequences of Mouse Anti-Human XCR1 Antibody (5G7)

| Name | Sequence |
|---|---|
| Heavy chain variable region (SEQ ID NO: 7) | CAGGCTTATCTTCAGCAGTCTGGGGCTGAACTGGTGAGGCCTGGGG CCTCAGTGAAGATGTCCTGCAAGGCTTCTGGCTACACATTCACCAG TCACAATTTGCACTGGGTAAAGCAGACACCTAGACAGGGCCTGCAA TGGATTGGAGCTATTTATCCAGGAAATGGTAATACTGCCTACAATC AGAAGTTCAAGGGCAAGGCCACGCTGACTGTAGACAAATCCTCCAG TACAGCCTACATGCAGCTCAGCAGCCTGACATCTGATGACTCTGCG GTCTACTTCTGTGCAAGATGGGGTTCGGTTGTAGGAGACTGGTACT TCGACGTCTGGGGCACAGGGACCACGGTCACCGTCTCCTCA |
| Light chain variable region (SEQ ID NO: 8) | GATGTTGTGATGACCCAAACTCCACTCTCCCTGCCTGTCACTCTTG GAAATCAAGCCTCCATTTTTTGTAGATCTAGTCTGGGCCTTGTACA CAGAAATGGAAACACCTATTTACATTGGTACCTGCAGAAGCCAGGC CAGTCTCCAAAGCTCCTGATCTACAAAGTTTCCCACCGATTTTCTG GGGTCCCAGACAGGTTCAGTGGCAGTGGCTCAGGGACAGATTTCAC ACTCAAGATCAGCAGAGTGGAGGCTGAGGATCTGGGGGTTTATTTC TGCTCTCAAAGTACCCATGTTCCGTGGACGTTCGGTGGAGGCACCA AGCTGGAAATCAAA |

TABLE 4-1

Amino Acid Sequences of Mouse Anti-Human XCR1 Antibody (11H2)

| Name | Sequence |
|---|---|
| Heavy chain variable region (SEQ ID NO: 9) | EVQLQQSGPVLVKPGASVKMSCKASGYTFTDYYVNWVKQSHGASLE WIGVSNPKNGDKSYNQKFKGKATLTVDKSSSTAYMELNSLTSEDSA VYYCARGLYYAGTYGYFDVWGTGTTVTVSS |
| Light chain variable region (SEQ ID NO: 10) | DIQMTQATSSLSASLGDRVTISCRASQDISNYLNWYQQKPDGTVKL LIYYTSRLHSGVPSRFRGSGSGTDFSLTISNLEQEDIATYFCQQGK TLPRTLGGGTKLEIK |

TABLE 4-2

Nucleic Acid Sequences of Mouse Anti-Human XCR1 Antibody (11H2)

| Name | Sequence |
|---|---|
| Heavy chain variable region (SEQ ID NO: 11) | GAGGTCCAGCTTCAACAGTCTGGACCTGTGCTGGTGAAGCCTGGGG CTTCAGTGAAGATGTCCTGTAAGGCTTCTGGATACACATTCACTGA CTACTATGTGAACTGGGTGAAACAGAGCCATGGAGCGAGCCTTGAG TGGATTGGAGTTAGTAATCCTAAGAACGGTGATAAAAGTTACAACC AGAAGTTCAAGGGCAAGGCCACATTGACTGTTGACAAGTCCTCCAG TACAGCCTACATGGAGCTCAACAGCCTGACATCTGAGGACTCTGCT GTCTATTACTGTGCAAGAGGGCTTTACTACGCTGGTACCTACGGGT ACTTCGATGTCTGGGGCACGGGGACCACGGTCACCGTCTCCTCA |
| Light chain variable region (SEQ ID NO: 12) | GATATCCAGATGACACAGGCTACATCCTCCCTGTCTGCCTCTCTGG GAGACAGAGTCACCATCAGTTGTAGGGCAAGTCAGGACATTAGCAA TTATTTAAACTGGTATCAGCAGAAGCCAGATGGAACTGTTAAACTC CTGATCTACTACACATCAAGATTACACTCAGGTGTCCCATCAAGGT TCAGAGGCAGTGGGTCTGGGACAGATTTCTCTCTCACCATTAGCAA CCTGGAGCAAGAAGATATTGCCACTTATTTTTGCCAACAGGGTAAA ACGCTTCCTCGGACGCTCGGTGGAGGCACCAAGCTGGAAATCAAA |

Example 2

(1) Preparation of Chimeric Anti-Human XCR1 Antibody and Humanized Anti-Human XCR1 Antibodies 5G7, which demonstrated the highest neutralizing activity among 2H6, 5G7, and 11H2, was used to produce a chimeric antibody and humanized antibodies.

The chimeric antibody was prepared by combining, by overlapping extension PCR, the gene sequence of the 5G7 heavy chain variable region and the gene sequence of the human IgG2 constant region into which V234A/G237A mutation was inserted for heavy chain and the sequence of the 5G7 light chain variable region and the gene sequence of human Igκ constant region, and by inserting the resulting sequence into expression vectors (pEE6.4 or pEE12.4). Tables 5 and 6 respectively show amino acid sequences and nucleotide sequences of the specific chimeric antibody.

TABLE 5

Amino Acid Sequences of Chimeric Anti-Human XCR1 Antibody

| Name | Sequence (The variable region is indicated in bold, and CDRs in the variable region are underlined.) |
|---|---|
| Heavy chain (SEQ ID NO: 13) | QAYLQQSGAELVRPGASVKMSCKASGYTFT<u>SHNLH</u>WVKQTPRQGLQ WIGA<u>IYPGNGNTAYNQKFKG</u>KATLTVDKSSSTAYMQLSSLTSDDSA VYFCAR<u>WGSVVGDWYFDV</u>WGTGTTVTVSSASTKGPSVFPLAPCSRS TSESTAALGCLVKDYFPEPVTVSWNSGALTSGVHTFPAVLQSSGLY SLSSVVTVPSSNFGTQTYTCNVDHKPSNTKVDKTVERKCCVECPPC PAPPAAAPSVFLFPPKPKDTLMISRTPEVTCVVVDVSHEDPEVQFN WYVDGVEVHNAKTKPREEQFNSTFRVVSVLTVVHQDWLNGKEYKCK VSNKGLPAPIEKTISKTKGQPREPQVYTLPPSREEMTKNQVSLTCL VKGFYPSDIAVEWESNGQPENNYKTTPPMLDSDGSFFLYSKLTVDK SRWQQGNVFSCSVMHEALHNHYTQKSLSLSPGK |

TABLE 5-continued

Amino Acid Sequences of Chimeric Anti-Human XCR1 Antibody

| Name | Sequence (The variable region is indicated in bold, and CDRs in the variable region are underlined.) |
|---|---|
| Light chain (SEQ ID NO: 14) | DVVMTQTPLSLPVTLGNQASIFC<u>RSSLGLVHRNGNTYLH</u>WYLQKPG QSPKLLIY<u>KVSHRFS</u>GVPDRFSGSGSGTDFTLKISRVEAEDLGVYF C<u>SQSTHVPWT</u>FGGGTKLEIKRTVAAPSVFIFPPSDEQLKSGTASVV CLLNNFYPREAKVQWKVDNALQSGNSQESVTEQDSKDSTYSLSSTL TLSKADYEKHKVYACEVTHQGLSSPVTKSFNRGEC |

TABLE 6

Nucleic Acid Sequences of Chimeric Anti-Human XCR1 Antibody

| Name | Sequence (The variable region is indicated in bold.) |
|---|---|
| Heavy chain (SEQ ID NO: 15) | CAGGCTTATCTTCAGCAGTCTGGGGCTGAACTGGTGAGGCCTGGGG CCTCAGTGAAGATGTCCTGCAAGGCTTCTGGCTACACATTCACCAG TCACAATTTGCACTGGGTAAAGCAGACACCTAGACAGGGCCTGCAA TGGATTGGAGCTATTTATCCAGGAAATGGTAATACTGCCTACAATC AGAAGTTCAAGGGCAAGGCCACGCTGACTGTAGACAAATCCTCCAG TACAGCCTACATGCAGCTCAGCAGCCTGACATCTGATGACTCTGCG GTCTACTTCTGTGCAAGATGGGGTTCGGTTGTAGGAGACTGGTACT TCGACGTCTGGGGCACAGGGACCACGGTCACCGTCTCCTCAGCTAG CACCAAGGGCCCATCGGTCTTCCCCCTGGCGCCCTGCTCCAGGAGC ACCTCCGAGAGCACAGCGGCCCTGGGCTGCCTGGTCAAGGACTACT TCCCCGAACCGGTGACGGTGTCGTGGAACTCAGGCGCTCTGACCAG CGGCGTGCACACCTTCCCGGCTGTCCTACAGTCCTCAGGACTCTAC TCCCTCAGCAGCGTGGTGACCGTGCCCTCCAGCAACTTCGGCACCC AGACCTACACCTGCAACGTAGATCACAAGCCCAGCAACACCAAGGT GGACAAGACAGTTGAGCGCAAATGTTGTGTCGAGTGCCCACCGTGC CCAGCACCACCTGCCGCAGCCCCGTCAGTCTTCCTGTTCCCCCCAA AACCCAAGGACACCCTCATGATCTCCCGGACCCCTGAGGTCACGTG CGTGGTGGTGGACGTGAGCCACGAAGACCCCGAGGTCCAGTTCAAC TGGTACGTGGACGGCGTGGAGGTGCATAATGCCAAGACAAAGCCAC GGGAGGAGCAGTTCAACAGCACGTTCCGTGTGGTCAGCGTCCTCAC CGTCGTGCACCAGGACTGGCTGAACGGCAAGGAGTACAAGTGCAAG GTCTCCAACAAAGGCCTCCCAGCCCCCATCGAGAAAACCATCTCCA AAACCAAAGGGCAGCCCCGAGAACCACAGGTGTACACCCTGCCCCC ATCCCGGGAGGAGATGACCAAGAACCAGGTCAGCCTGACCTGCCTG GTCAAAGGCTTCTACCCCAGCGACATCGCCGTGGAGTGGGAGAGCA ATGGGCAGCCGGAGAACAACTACAAGACCACACCTCCCATGCTGGA CTCCGACGGCTCCTTCTTCCTCTACAGCAAGCTCACCGTGGACAAG AGCAGGTGGCAGCAGGGGAACGTCTTCTCATGCTCCGTGATGCATG AGGCTCTGCACAACCACTACACACAGAAGAGCCTCTCCCTGTCTCC GGGTAAATGA |
| Light chain (SEQ ID NO: 16) | GATGTTGTGATGACCCAAACTCCACTCTCCCTGCCTGTCACTCTTG GAAATCAAGCCTCCATTTTTTGTAGATCTAGTCTGGGCCTTGTACA CAGAAATGGAAACACCTATTTACATTGGTACCTGCAGAAGCCAGGC CAGTCTCCAAAGCTCCTGATCTACAAAGTTTCCCACCGATTTTCTG GGGTCCCAGACAGGTTCAGTGGCAGTGGCTCAGGGACAGATTTCAC ACTCAAGATCAGCAGAGTGGAGGCTGAGGATCTGGGGGTTTATTTC TGCTCTCAAAGTACCCATGTTCCGTGGACGTTCGGTGGAGGCACCA AGCTGGAAATCAAACGTACGGTGGCTGCACCATCTGTCTTCATCTT CCCGCCATCTGATGAGCAGTTGAAATCTGGAACTGCCTCTGTTGTG TGCCTGCTGAATAACTTCTATCCCAGAGAGGCCAAAGTACAGTGGA AGGTGGATAACGCCCTCCAATCGGGTAACTCCCAGGAGAGTGTCAC AGAGCAGGACAGCAAGGACAGCACCTACAGCCTCAGCAGCACCCTG ACGCTGAGCAAAGCAGACTACGAGAAACACAAAGTCTACGCCTGCG AAGTCACCCATCAGGGCCTGAGCTCGCCCGTCACAAAGAGCTTCAA CAGGGGAGAGTGTTAG |

The antibody was humanized by grafting the complementary determining region of mouse antibody 5G7 into the human antibody variable region. The complementary determining region was determined according to the Kabat numbering system and a method for identifying the complementary determining region (for example, Kabat et al., (1991) Sequences of Proteins of Immunological Interest: US Department of Health and Human Services, NIH, USA). Further, the complementary determining regions of 2H6 and 11H2 were also determined in a similar manner. Tables 7-1 to 9-2 show amino acid sequences and nucleotide sequences of the complementary determining regions of these three clones.

TABLE 7-1

Amino Acid Sequences of Complementary Determining Region of 5G7

| Name | Sequence |
| --- | --- |
| Heavy chain CDR 1 (SEQ ID NO: 17) | SHNLH |
| Heavy chain CDR 2 (SEQ ID NO: 18) | AIYPGNGNTAYNQKFKG |
| Heavy chain CDR 3 (SEQ ID NO: 19) | WGSVVGDWYFDV |
| Light chain CDR 1 (SEQ ID NO: 20) | RSSLGLVHRNGNTYLH |
| Light chain CDR 2 (SEQ ID NO: 21) | KVSHRFS |
| Light chain CDR 3 (SEQ ID NO: 22) | SQSTHVPWT |

TABLE 7-2

Nucleic Acid Sequences of Complementary Determining Region of 5G7

| Name | Sequence |
| --- | --- |
| Heavy chain CDR 1 (SEQ ID NO: 23) | AGTCACAATTTGCAC |
| Heavy chain CDR 2 (SEQ ID NO: 24) | GCTATTTATCCAGGAAATGGTAATACTGCCTACAATCAGAAGTTCAAGGGC |
| Heavy chain CDR 3 (SEQ ID NO: 25) | TGGGGTTCGGTTGTAGGAGACTGGTACTTCGACGTC |
| Light chain CDR 1 (SEQ ID NO: 26) | AGATCTAGTCTGGGCCTTGTACACAGAAATGGAAACACCTATTTACAT |
| Light chain CDR 2 (SEQ ID NO: 27) | AAAGTTTCCCACCGATTTTCT |
| Light chain CDR 3 (SEQ ID NO: 28) | TCTCAAAGTACCCATGTTCCGTGGACG |

TABLE 8-1

Amino Acid Sequences of Complementary Determining Region of 2H6

| Name | Sequence |
| --- | --- |
| Heavy chain CDR 1 (SEQ ID NO: 29) | SHNMH |
| Heavy chain CDR 2 (SEQ ID NO: 30) | AIYPGKGNTSYNQKFKG |
| Heavy chain CDR 3 (SEQ ID NO: 31) | WGSVVGDWYFDV |
| Light chain CDR 1 (SEQ ID NO: 32) | RSSQSLVHSNGNTYLH |
| Light chain CDR 2 (SEQ ID NO: 33) | RVSNRFS |
| Light chain CDR 3 (SEQ ID NO: 34) | SQSTFVPWT |

TABLE 8-2

Nucleic Acid Sequences of Complementary Determining Region of 2H6

| Name | Sequence |
| --- | --- |
| Heavy chain CDR 1 (SEQ ID NO: 35) | AGTCACAATATGCAC |
| Heavy chain CDR 2 (SEQ ID NO: 36) | GCTATTTATCCAGGAAAAGGTAATACTTCCTACAATCAGAAGTTCAAGGGC |
| Heavy chain CDR 3 (SEQ ID NO: 37) | TGGGGTTCGGTAGTAGGAGACTGGTACTTCGATGTC |
| Light chain CDR 1 (SEQ ID NO: 38) | AGATCTAGTCAGAGCCTTGTACACAGTAATGGAAACACCTATTTACAT |
| Light chain CDR 2 (SEQ ID NO: 39) | AGAGTTTCCAATCGATTTTCT |
| Light chain CDR 3 (SEQ ID NO: 40) | TCTCAAAGTACATTTGTTCCGTGGACG |

TABLE 9-1

Amino Acid Sequences of Complementary Determining Region of 11H2

| Name | Sequence |
| --- | --- |
| Heavy chain CDR 1 (SEQ ID NO: 41) | DYYVN |
| Heavy chain CDR 2 (SEQ ID NO: 42) | VSNPKNGDKSYNQKFKG |
| Heavy chain CDR 3 (SEQ ID NO: 43) | GLYYAGTYGYFDV |
| Light chain CDR 1 (SEQ ID NO: 44) | RASQDISNYLN |
| Light chain CDR 2 (SEQ ID NO: 45) | YTSRLHS |
| Light chain CDR 3 (SEQ ID NO: 46) | QQGKTLPRT |

TABLE 9-2

Nucleic Acid Sequences of Complementary
Determining Region of 11H2

| Name | Sequence |
|---|---|
| Heavy chain CDR 1 (SEQ ID NO: 47) | GACTACTATGTGAAC |
| Heavy chain CDR 2 (SEQ ID NO: 48) | GTTAGTAATCCTAAGAACGGTGATAAAAGTTA CAACCAGAAGTTCAAGGGC |
| Heavy chain CDR 3 (SEQ ID NO: 49) | GGGCTTTACTACGCTGGTACCTACGGGTACT TCGATGTC |
| Light chain CDR 1 (SEQ ID NO: 50) | AGGGCAAGTCAGGACATTAGCAATTATTTA AAC |
| Light chain CDR 2 (SEQ ID NO: 51) | TACACATCAAGATTACACTCA |
| Light chain CDR 3 (SEQ ID NO: 52) | CAACAGGGTAAAACGCTTCCTCGGACG |

As is clear from Tables 7-1 and 8-1, the identity of the amino acid sequences of the CDRs between 5G7 and 2H6 is high; in particular, the heavy chain CDR 3 amino acid sequences were completely identical. Accordingly, in regard to 5G7 and 2H6, the amino acid sequences can be generalized as shown in Table 10 below. Additionally, FIG. 7 shows the comparison of amino acid sequences of the CDRs 1 to 3 of these clones.

TABLE 10

Generalized Amino Acid Sequences of Complementary
Determining Regions of 5G7 and 2H6

| Name | Sequence |
|---|---|
| Heavy chain CDR 1 (SEQ ID NO: 53) | SHNXH |
| Heavy chain CDR 2 (SEQ ID NO: 54) | AIYPGXGNTXYNQKFKG |
| Heavy chain CDR 3 (SEQ ID NO: 55) | WGSVVGDWYFDV |
| Light chain CDR 1 (SEQ ID NO: 56) | RSSXXLVHXNGNTYLH |
| Light chain CDR 2 (SEQ ID NO: 57) | XVSXRFS |
| Light chain CDR 3 (SEQ ID NO: 58) | SQSTXVPWT |

The "X" in the table may be any of the following: alanine (Ala: A), arginine (Arg: R), asparagine (Asn: N), aspartic acid (Asp: D), cysteine (Cys: C), glutamine (Gln: Q), glutamic acid (Glu: E), glycine (Gly: G), histidine (His: H), isoleucine (Ile: I), leucine (Leu: L), lysine (Lys: K), methionine (Met: M), phenylalanine (Phe: F), proline (Pro: P), serine (Ser: S), threonine (Thr: T), tryptophan (Trp: W), tyrosine (Tyr: Y), and valine (Val: V).

The FRs of a human antibody with high identity to the FR of 5G7 were selected as the FRs of the humanized antibodies. Subsequently, the amino acids in the FRs, which interact with the CDRs of 5G7, were predicted using the 3D model of the resulting antibody, and grafted with the CDRs. The human IgG2 constant region into which V234A/G237A mutation was inserted was used as the constant region. HK1 and HK5 were designed as the humanized antibody heavy chains, and L2 and L5 were designed as the humanized antibody light chains. Tables 11-1 to 14-2 show amino acid sequences and nucleotide sequences of the specific humanized antibodies.

TABLE 11-1

Amino Acid Sequences of Humanized Anti-Human XCR1
Antibody Heavy Chain (HK1)

| Name | Sequence (The variable region is indicated in bold, and CDRs in the variable region are underlined.) |
|---|---|
| Heavy chain (SEQ ID NO: 59) | QVQLVQSGAEVKKPGASVKVSCKASGYTFT<u>SHNLH</u>WVRQAPGQRLE WMGA<u>IYPGNGNTAYNQKFKG</u>RVTITRDTSASTAYMELSSLRSEDTA VYYCAR<u>WGSVVGDWYFDV</u>WGQGTLVTVSSASTKGPSVFPLAPCSRS TSESTAALGCLVKDYFPEPVTVSWNSGALTSGVHTFPAVLQSSGLY SLSSVVTVPSSNFGTQTYTCNVDHKPSNTKVDKTVERKCCVECPPC PAPPAAAPSVFLFPPKPKDTLMISRTPEVTCVVVDVSHEDPEVQFN WYVDGVEVHNAKTKPREEQFNSTFRVVSVLTVVHQDWLNGKEYKCK VSNKGLPAPIEKTISKTKGQPREPQVYTLPPSREEMTKNQVSLTCL VKGFYPSDIAVEWESNGQPENNYKTTPPMLDSDGSFFLYSKLTVDK SRWQQGNVFSCSVMHEALHNHYTQKSLSLSPGK |
| Heavy chain variable region (SEQ ID NO: 60) | QVQLVQSGAEVKKPGASVKVSCKASGYTFT<u>SHNLH</u>WVRQAPGQRLE WMGA<u>IYPGNGNTAYNQKFKG</u>RVTITRDTSASTAYMELSSLRSEDTA VYYCAR<u>WGSVVGDWYFDV</u>WGQGTLVTVSS |

TABLE 11-2

Nucleic Acid Sequences of Humanized Anti-Human
XCR1 Antibody Heavy Chain (HK1)

| Name | Sequence (The variable region is indicated in bold, and CDRs in the variable region are underlined.) |
|---|---|
| Heavy chain (SEQ ID NO: 61) | CAGGTGCAGCTGGTGCAGTCTGGAGCCGAAGTGAAGAAACCAGGGG CCTCTGTCAAGGTGAGTTGCAAGGCCTCCGGTTACACTTTCACC<u>TC CCACAACCTGCATT</u>GGGTGAGACAGGCTCCTGGACAGCGACTGGAG TGGATGGGA<u>GCAATCTACCCAGGCAACGGAAATACTGCCTATAATC AGAAGTTTAAAGGC</u>AGGGTGACAATTACTCGGGACACTTCCGCAAG CACCGCCTACATGGAGCTGTCCAGCCTGAGGAGTGAAGATACCGCT GTGTACTATTGTGCACGA<u>TGGGGATCCGTGGTCGGAGACTGGTATT TCGATGTGTGGGGG</u>CAGGGTACCCTGGTCACAGTGTCTAGTGCCTC CACAAAGGGCCCCAGCGTGTTTCCACTGGCTCCCTGCTCTAGGAGT ACATCAGAGTCCACTGCCGCTCTGGGATGTCTGGTGAAGGACTATT TCCCTGAACCAGTCACCGTGAGTTGGAACTCAGGGGCTCTGACATC TGGTGTCCACACTTTTCCTGCAGTGCTGCAGTCATCCGGCCTGTAC TCCCTGAGCTCTGTGGTCACAGTCCCAAGTTCAAATTTCGGAACCC AGACATATACTTGCAACGTGGACCATAAGCCCAGCAATACCAAGGT CGATAAAACAGTGGAGCGAAAGTGCTGTGTCGAATGCCCACCTTGT CCAGCTCCACCAGCAGCAGCTCCTTCTGTGTTCCTGTTTCCTCCAA AGCCAAAAGACACTCTGATGATCAGCCGGACCCCCGAGGTCACATG TGTGGTCGTGGACGTGTCTCACGAGGATCCTGAAGTCCAGTTTAAC TGGTACGTGGATGGGGTCGAAGTGCATAATGCAAAGACAAAACCAC GAGAGGAACAGTTCAACTCTACATTTCGTGTCGTGAGTGTGCTGAC TGTCGTGCACCAGGATTGGCTGAACGGCAAGGAGTATAAGTGCAAA GTGTCCAATAAGGGACTGCCCGCCCCTATCGAGAAAACTATTAGCA AGACCAAAGGCCAGCCTAGAGAACCACAGGTGTACACCCTGCCCCC TAGTCGCGAGGAAATGACTAAGAACCAGGTCTCACTGACCTGTCTG GTGAAAGGGTTCTATCCCAGCGACATTGCCGTGGAGTGGGAATCTA ATGGTCAGCCTGAGAACAATTACAAGACCACACCCACCCATGCTGGA CTCCGATGGGAGCTTCTTTCTGTATTCAAAGCTGACCGTGGATAAA TCCAGGTGGCAGCAGGGTAATGTCTTTAGCTGCTCTGTGATGCACG AAGCCCTGCACAACCATTACACTCAGAAGTCCCTGTCCCTGTCACC TGGAAAGTGA |
| Heavy chain variable region (SEQ ID NO: 62) | CAGGTGCAGCTGGTGCAGTCTGGAGCCGAAGTGAAGAAACCAGGGG CCTCTGTCAAGGTGAGTTGCAAGGCCTCCGGTTACACTTTCACC<u>TC CCACAACCTGCATT</u>GGGTGAGACAGGCTCCTGGACAGCGACTGGAG TGGATGGGA<u>GCAATCTACCCAGGCAACGGAAATACTGCCTATAATC AGAAGTTTAAAGGC</u>AGGGTGACAATTACTCGGGACACTTCCGCAAG CACCGCCTACATGGAGCTGTCCAGCCTGAGGAGTGAAGATACCGCT GTGTACTATTGTGCACGA<u>TGGGGATCCGTGGTCGGAGACTGGTATT TCGATGTGTGGGGG</u>CAGGGTACCCTGGTCACAGTGTCTAGT |

TABLE 12-1

Amino Acid Sequences of Humanized Anti-Human XCR1
Antibody Heavy Chain (HK5)

| Name | Sequence (The variable region is indicated in bold, and CDRs in the variable region are underlined.) |
|---|---|
| Heavy chain (SEQ ID NO: 63) | QVQLVQSGAEVKKPGASVKVSCKASGYTFT<u>SHNLH</u>WVRQAPGQGLE WMG<u>AIYPGNGNTAYNQKFKG</u>RVTMTRDTSTSTVYMELSSLRSEDTA VYYCAR<u>WGSVVGDWYFDV</u>WGQGTLVTVSSASTKGPSVFPLAPCSRS TSESTAALGCLVKDYFPEPVTVSWNSGALTSGVHTFPAVLQSSGLY SLSSVVTVPSSNFGTQTYTCNVDHKPSNTKVDKTVERKCCVECPPC PAPPAAAPSVFLFPPKPKDTLMISRTPEVTCVVVDVSHEDPEVQFN WYDGVEVHNAKTKPREEQFNSTFRVVSVLTVVHQDWLNGKEYKCK VSNKGLPAPIEKTISKTKGQPREPQVYTLPPSREEMTKNQVSLTCL VKGFYPSDIAVEWESNGQPENNYKTTPPMLDSDGSFFLYSKLTVDK SRWQQGNVFSCSVMHEALHNHYTQKSLSLSPGK |
| Heavy chain variable region (SEQ ID NO: 64) | QVQLVQSGAEVKKPGASVKVSCKASGYTFT<u>SHNLH</u>WVRQAPGQGLE WMG<u>AIYPGNGNTAYNQKFKG</u>RVTMTRDTSTSTVYMELSSLRSEDTA VYYCAR<u>WGSVVGDWYFDV</u>WGQGTLVTVSS |

TABLE 12-2

Nucleic Acid Sequences of Humanized Anti-Human
XCR1 Antibody Heavy Chain (HK5)

| Name | Sequence (The variable region is indicated in bold, and CDRs in the variable region are underlined.) |
|---|---|
| Heavy chain (SEQ ID NO: 65) | CAGGTGCAGCTGGTGCAGTCTGGGGCCGAAGTGAAGAAACCAGGGG CTTCTGTCAAGGTGAGTTGCAAAGCATCAGGTTACACTTTCACC<u>TC CCACAACCTGCATTGGGTGCGACAGGCTCCTGGACAGGGACTGGAG TGGATGGGAGCAATCTACCCAGGGAACGGTAATACCGCTTATAATC AGAAGTTTAAAGGC</u>AGGGTCACAATGACTCGGGACACCTCCACAAG CACTGTGTACATGGAGCTGTCCAGCCTGCGAAGTGAAGATACAGCA GTGTACTATTGTGCACGT<u>TGGGGATCCGTGGTCGGTGACTGGTATT TCGATGTGTGGGGC</u>CAGGGAACCCTGGTCACAGTGTCTAGTGCTTC CACTAAGGGCCCAGCGTGTTTCCACTGGCACCCTGCTCTCGGAGT ACTTCAGAGTCCACCGCCGCTCTGGGCTGTCTGGTGAAGGACTATT TCCCTGAACCAGTCACAGTGAGTTGGAACTCAGGCGCACTGACTTC TGGAGTCCACACCTTTCCTGCCGTGCTGCAGTCATCCGGCCTGTAC TCCCTGAGCTCTGTGGTCACTGTCCCAAGTTCAAATTTCGGAACCC AGACATATACTTGCAACGTGGACCATAAGCCCAGCAATACAAAGGT CGATAAAACTGTGGAGAGAAAGTGCTGTGTGGAATGCCCACCTTGT CCAGCACCACCAGCAGCAGCTCCTTCTGTGTTCCTGTTTCCTCCAA AGCCAAAAGACACACTGATGATCAGCCGCACACCCGAGGTCACTTG TGTGGTCGTGGACGTGTCTCACGAGGATCCTGAAGTCCAGTTTAAC TGGTACGTGGATGGCGTCGAAGTGCATAATGCCAAGACCAAACCAA GAGAGGAACAGTTCAACTCTACTTTTCGCGTCGTGAGTGTGCTGAC CGTCGTGCACCAGGATTGGCTGAACGGCAAGGAGTATAAGTGCAAA GTGTCCAATAAGGGACTGCCCGCTCCTATCGAGAAAACCATTAGCA AGACAAAAGGACAGCCTAGGGAACCACAGGTGTACACCCTGCCCCC TAGTCGGGAGGAAATGACCAAGAACCAGGTCTCACTGACATGTCTG GTGAAAGGGTTCTATCCCAGCGACATTGCCGTGGAGTGGGAATCTA ATGGTCAGCCTGAGAACAATTACAAGACCACACCCACCCATGCTGGA CTCCGATGGCAGCTTCTTTCTGTATTCAAAGCTGACCGTGGATAAA TCCAGGTGGCAGCAGGGAAATGTCTTTAGCTGCTCTGTGATGCACG AAGCACTGCATAATCACTACACTCAGAAGAGCCTGTCCCTGTCACC TGGTAAATGA |
| Heavy chain variable region (SEQ ID NO: 66) | CAGGTGCAGCTGGTGCAGTCTGGGGCCGAAGTGAAGAAACCAGGGG CTTCTGTCAAGGTGAGTTGCAAAGCATCAGGTTACACTTTCACC<u>TC CCACAACCTGCATTGGGTGCGACAGGCTCCTGGACAGGGACTGGAG TGGATGGGAGCAATCTACCCAGGGAACGGTAATACCGCTTATAATC AGAAGTTTAAAGGC</u>AGGGTCACAATGACTCGGGACACCTCCACAAG CACTGTGTACATGGAGCTGTCCAGCCTGCGAAGTGAAGATACAGCA GTGTACTATTGTGCACGT<u>TGGGGATCCGTGGTCGGTGACTGGTATT TCGATGTGTGGGGC</u>CAGGGAACCCTGGTCACAGTGTCTAGT |

TABLE 13-1

Amino Acid Sequences of Humanized Anti-Human XCR1
Antibody Light Chain (L2)

| Name | Sequence (The variable region is indicated in bold, and CDRs in the variable region are underlined.) |
|---|---|
| Light chain (SEQ ID NO: 67) | DVVMTQSPLSLPVTLGQPASISC<u>RSSLGLVHRNGNTYLH</u>WFQQRPG QSPRLLIY<u>KVSHRFS</u>GVPDRFSGSGSGTDFTLKISRVEAEDVGVYY C<u>SQSTHVPWT</u>FGQGTKVEIKRTVAAPSVFIFPPSDEQLKSGTASVV CLLNNFYPREAKVQWKVDNALQSGNSQESVTEQDSKDSTYSLSSTL TLSKADYEKHKVYACEVTHQGLSSPVTKSFNRGEC |
| Light chain variable region (SEQ ID NO: 68) | DVVMTQSPLSLPVTLGQPASISC<u>RSSLGLVHRNGNTYLH</u>WFQQRPG QSPRLLIY<u>KVSHRFS</u>GVPDRFSGSGSGTDFTLKISRVEAEDVGVYY C<u>SQSTHVPWT</u>FGQGTKVEIK |

TABLE 13-2

Nucleic Acid Sequences of Humanized Anti-Human XCR1 Antibody Light Chain (L2)

| Name | Sequence (The variable region is indicated in bold, and CDRs in the variable region are underlined.) |
| --- | --- |
| Light chain (SEQ ID NO: 69) | GATGTCGTGATGACCCAGTCTCCTCTGAGCCTGCCTGTGACTCTGG GCCAGCCAGCATCAATCTCCTGC<u>CGATCCAGCCTGGGACTGGTGCA CCGTAACGGGAATACCTACCTGCATTGGTT</u>CCAGCAGAGGCCTGGT CAGAGTCCCCGGCTGCTGATCTATA<u>AGGTGTCTCACAGATTCAGTG</u> GCGTCCCAGACCGCTTTAGCGGCTCTGGAAGTGGGACTGATTTCAC CCTGAAAATTTCCCGAGTGGAGGCAGAAGACGTGGGAGTCTACTAT TGC<u>TCACAGTCCACACATGTGCCCTGGACTTTT</u>GGTCAGGGCACCA AGGTCGAGATCAAACGCACCGTGGCCGCTCCTAGCGTCTTCATTTT TCCCCCTTCTGACGAACAGCTGAAGTCAGGAACAGCTTCCGTGGTC TGTCTGCTGAACAATTTTTACCCCAGAGAGGCAAAGGTGCAGTGGA AGTCGATAACGCCCTGCAGAGCGGCAACTCCCAGGAGAGTGTGAC AGAACAGGACTCAAAGGATTCCACTTATAGCCTGTCTAGTACCCTG ACACTGTCTAAAGCTGATTACGAGAAGCACAAAGTGTATGCATGTG AAGTCACCCACCAGGGGCTGTCATCACCCGTCACCAAGTCCTTTAA TAGAGGGGAGTGTTGA |
| Light chain variable region (SEQ ID NO: 70) | GATGTCGTGATGACCCAGTCTCCTCTGAGCCTGCCTGTGACTCTGG GCCAGCCAGCATCAATCTCCTGC<u>CGATCCAGCCTGGGACTGGTGCA CCGTAACGGGAATACCTACCTGCATTGGTT</u>CCAGCAGAGGCCTGGT CAGAGTCCCCGGCTGCTGATCTATA<u>AGGTGTCTCACAGATTCAGTG</u> GCGTCCCAGACCGCTTTAGCGGCTCTGGAAGTGGGACTGATTTCAC CCTGAAAATTTCCCGAGTGGAGGCAGAAGACGTGGGAGTCTACTAT TGC<u>TCACAGTCCACACATGTGCCCTGGACTTTT</u>GGTCAGGGCACCA AGGTCGAGATCAAA |

TABLE 14-1

Amino Acid Sequences of Humanized Anti-Human XCR1 Antibody Light Chain (L5)

| Name | Sequence (The variable region is indicated in bold, and CDRs in the variable region are underlined.) |
| --- | --- |
| Light chain (SEQ ID NO: 71) | DIVMTQTPLSLPVTPGQPASISC<u>RSSLGLVHRNGNTYLH</u>WYLQKPG QSPQLLIY<u>KVSHRFS</u>GVPDRFSGSGSGTDFTLKISRVEAEDVGVYY C<u>SQSTHVPWT</u>FGQGTKVEIKRTVAAPSVFIFPPSDEQLKSGTASVV CLLNNFYPREAKVQWKVDNALQSGNSQESVTEQDSKDSTYSLSSTL TLSKADYEKHKVYACEVTHQGLSSPVTKSFNRGEC |
| Light chain Variable Region (SEQ ID NO: 72) | DIVMTQTPLSLPVTPGQPASISC<u>RSSLGLVHRNGNTYLH</u>WYLQKPG QSPQLLIY<u>KVSHRFS</u>GVPDRFSGSGSGTDFTLKISRVEAEDVGVYY C<u>SQSTHVPWT</u>FGQGTKVEIK |

TABLE 14-2

Nucleic Acid Sequences of Humanized Anti-Human XCR1 Antibody Light Chain (L5)

| Name | Sequence (The variable region is indicated in bold, and CDRs in the variable region are underlined.) |
| --- | --- |
| Light chain (SEQ ID NO: 73) | GATATTGTGATGACTCAGACTCCACTGAGCCTGCCAGTGACTCCCG GCCAGCCTGCATCAATCTCCTGC<u>AGATCCAGCCTGGGACTGGTGCA CCGCAACGGGAATACCTACCTGCATTGGTA</u>TCTGCAGAAGCCTGGT CAGAGTCCCCAGCTGCTGATCTAC<u>AAAGTGTCTCACAGGTTCAGTG</u> GCGTCCCCGACCGGTTTAGCGGCTCTGGAAGTGGGACTGATTTCAC CCTGAAGATTTCCCGAGTGGAGGCCGAAGACGTGGGCGTCTACTAT TGC<u>TCACAGTCCACACATGTGCCTTGACTTTT</u>GGTCAGGGCACCA AGGTCGAGATCAAAAGGACCGTGGCCGCTCCAAGCGTCTTCATTTT TCCCCCTTCTGACGAACAGCTGAAGTCAGGAACAGCTTCCGTGGTC TGTCTGCTGAACAATTTCTACCCCAGAGAGGCAAAGGTGCAGTGGA AGTCGATAACGCCCTGCAGAGCGGCAACTCCCAGGAGAGTGTGAC AGAACAGGACTCAAAGGATTCCACTTATAGCCTGTCTAGTACCCTG ACACTGTCTAAAGCTGATTACGAGAAGCACAAAGTGTATGCATGTG AAGTCACACACCAGGGTCTGAGTTCCCCCGTCACCAAATCCTTTAA TCGTGGAGAGTGCTGA |

TABLE 14-2-continued

Nucleic Acid Sequences of Humanized Anti-Human
XCR1 Antibody Light Chain (L5)

| Name | Sequence (The variable region is indicated in bold, and CDRs in the variable region are underlined.) |
|---|---|
| Light chain Variable Region (SEQ ID NO: 74) | GATATTGTGATGACTCAGACTCCACTGAGCCTGCCAGTGACTCCCG GCCAGCCTGCATCAATCTCCTGC<u>AGATCCAGCCTGGGACTGGTGCA CCGCAACGGGAATACCTACCTGCATTGGTATCTGCAGAAGCCTGGT</u> CAGAGTCCCCAGCTGCTGATCTAC<u>AAAGTGTCTCACAGGTTCAGTG</u> GCGTCCCCGACCGGTTTAGCGGCTCTGGAAGTGGGACTGATTTCAC CCTGAAGATTTCCCGAGTGGAGGCCGAAGACGTGGGCGTCTACTAT TGC<u>TCACAGTCCACACATGTGCCTTGGACTTTTGGT</u>CAGGGCACCA AGGTCGAGATCAAA |

Gene sequences of these humanized antibodies were entirely synthesized by GenScript USA Inc., and inserted into expression vectors (pEE6.4 or pEE12.4 purchased from Lonza). To produce antibodies, the expression vectors were transfected into HEK293E cells (Invitrogen) using Lipofectamine 2000 according to the instructions for Lipofectamine 2000 (Invitrogen). The supernatants were collected and purified using Protein A (GE Healthcare). The neutralizing activity was evaluated using these purified humanized antibodies.

Humanized antibodies having neutralizing activity against human lymphotactin-induced migration of human XCR1-expressing cells were identified by performing in vitro chemotaxis assays using human XCR1-expressing B300.19 cells. The chemotaxis assay was performed as described above using 96-well transwell culture plates (MultiScreen, pore 5 µm, Millipore, #MAMIC 5S10 or Corning #3387 or #3388). However, in the case of using Corning transwell culture plates, the amount of the recombinant human lymphotactin and purified antibodies to be added to the lower wells is 235 µL per well.

Among humanized antibodies having neutralizing activity, two types of the following antibodies, HK1L2 and HK5L5, were evaluated in further detail.

(2) Reactivity of Humanized Anti-Human XCR1 Antibodies (HK1L2 and HK5L5) to Human XCR1-Expressing Cells FACS analysis was performed using these two humanized antibodies (HK1L2 and HK5L5), the parent antibody 5G7, and the chimeric antibody. Parent B300.19 cells and human XCR1-EGFP-expressing B300.19 cells were mixed at a 1:1 ratio and suspended in a FACS buffer (1% FBS-containing PBS⁻ (Sigma)). The cells were incubated for 20 minutes on ice with the purified antibodies at various concentrations from 0 to 10 µg/mL. The cells were washed three times with the FACS buffer, and then incubated for 20 minutes on ice with PE-labeled anti-mouse IgG polyclonal antibody (Jackson, #715-116-151: used for cells which had been stained with parent antibody 5G7, diluted at 1:100 in the FACS buffer) or with PE-labeled anti-human IgG polyclonal antibody (Jackson, #709-116-149: used for cells which had been stained with chimeric antibody or humanized antibodies (HK1L2 and HK5L5), diluted at 1:100 in FACS buffer. The cells were washed three times with FACS buffer, and then suspended in FACS buffer. The fluorescence intensity was measured using a FACSCanto II cell analyzer (BD Bioscience).

Figure 3:
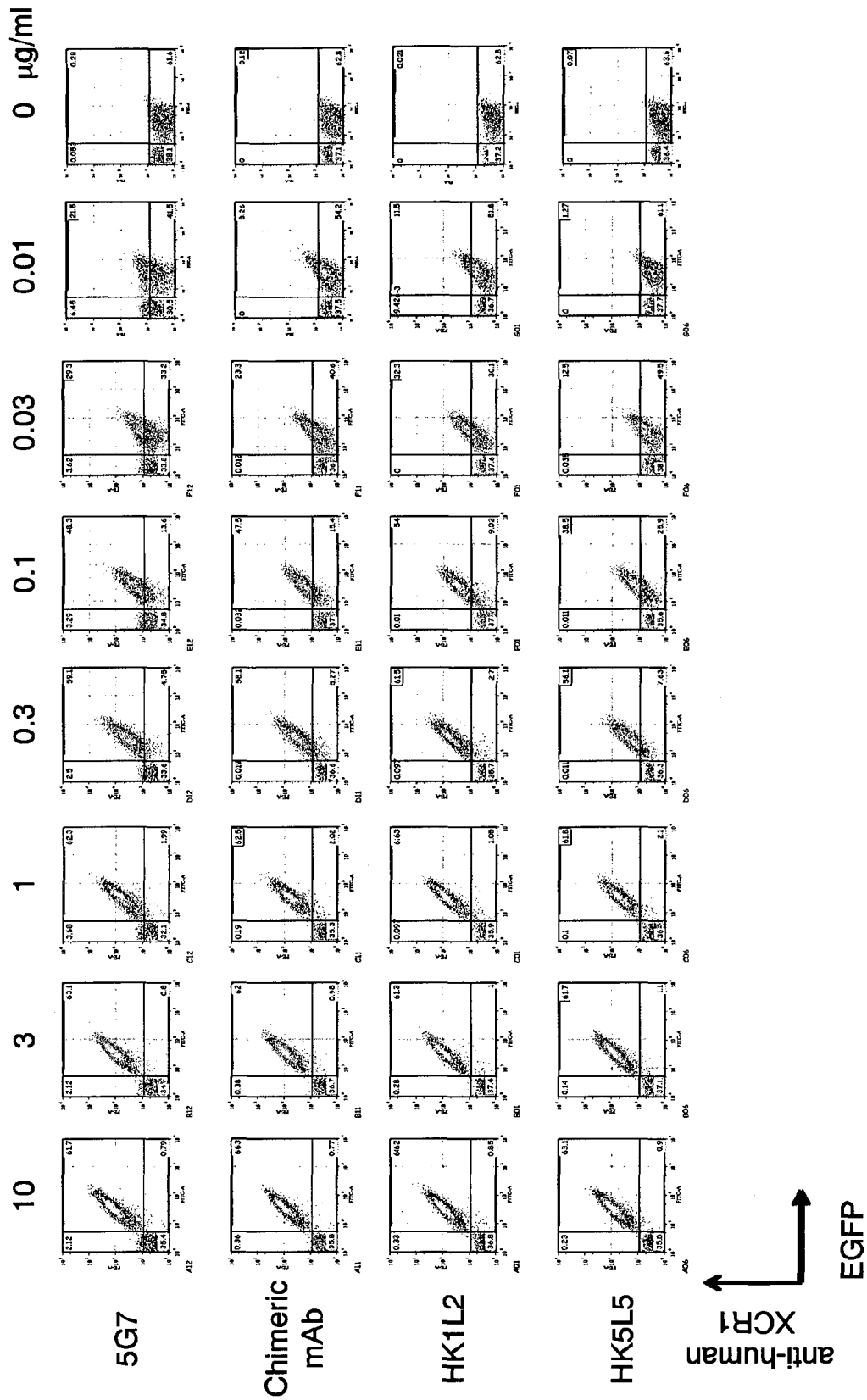
FIG. 3 shows the results of FACS analysis of the reactivity of humanized anti-human XCR1 antibodies (HK1L2 and HK5L5) to human XCR1-EGFP-expressing B300.19 cells, in parallel with the reactivity of their parent mouse anti-human XCR1 antibody (5G7) and its chimeric antibody.

Humanized antibodies (HK1L2 and HK5L5) showed concentration-dependent reactivity to human XCR1-EGFP-expressing B300.19 cells. Parent antibody 5G7 and chimeric antibody showed substantially the same reactivity (FIG. 3).

The reactivity of humanized antibodies (HK1L2 and HK5L5) to human XCR1 was further examined by FACS analysis using human peripheral blood mononuclear cells. Because human XCR1 gene is known to be expressed in BDCA3+ dendritic cells, which is a minor population in human peripheral blood mononuclear cells, first, the dendritic cells were concentrated from human peripheral blood mononuclear cells and used for FACS analysis. Human peripheral blood mononuclear cells were isolated from the blood of healthy human subjects using Ficoll-Paque (GE Healthcare, #17-1440-02). CD3, CD14, CD19, and CD56 positive cells from human peripheral blood mononuclear cells were labeled with CD3, CD14, CD19, CD56 antibody microbeads (Miltenyi, #130-050-101, #130-050-201, #130-050-301, #130-050-401), and depleted using auto-MACS (Miltenyi). Thereby, human dendritic cells were concentrated. The concentrated dendritic cells were blocked for 10 minutes on ice with a FACS buffer (1% FBS-containing PBS⁻ (Sigma)) containing 1% rat serum, 1% mouse serum, 100 µg/mL human immunoglobulin. The cells were then stained for 30 minutes on ice separately using PE-labeled 5G7, HK1L2, HK5L5, and isotype control antibody mouse IgG2b, κ (eBioscience, #14-4732-82) or human IgG2, κ (Sigma, #15404) with FITC-labeled anti-BDCA3 antibody (Miltenyi, #130-090-513), APC-labeled anti-CD123 antibody (Miltenyi, #130-090-901), APC-Cy7-labeled anti-HLA-DR antibody (BioLegend, #307617), and Alexa700-labeled anti-CD3, CD14, CD19, CD56 antibodies (BioLegend, #300324, #301822, #302225, and #318316). The cells were washed three times with the FACS buffer, and then suspended in the FACS buffer. The fluorescence intensity was measured using a FACSCanto II cell analyzer.

Figure 4:
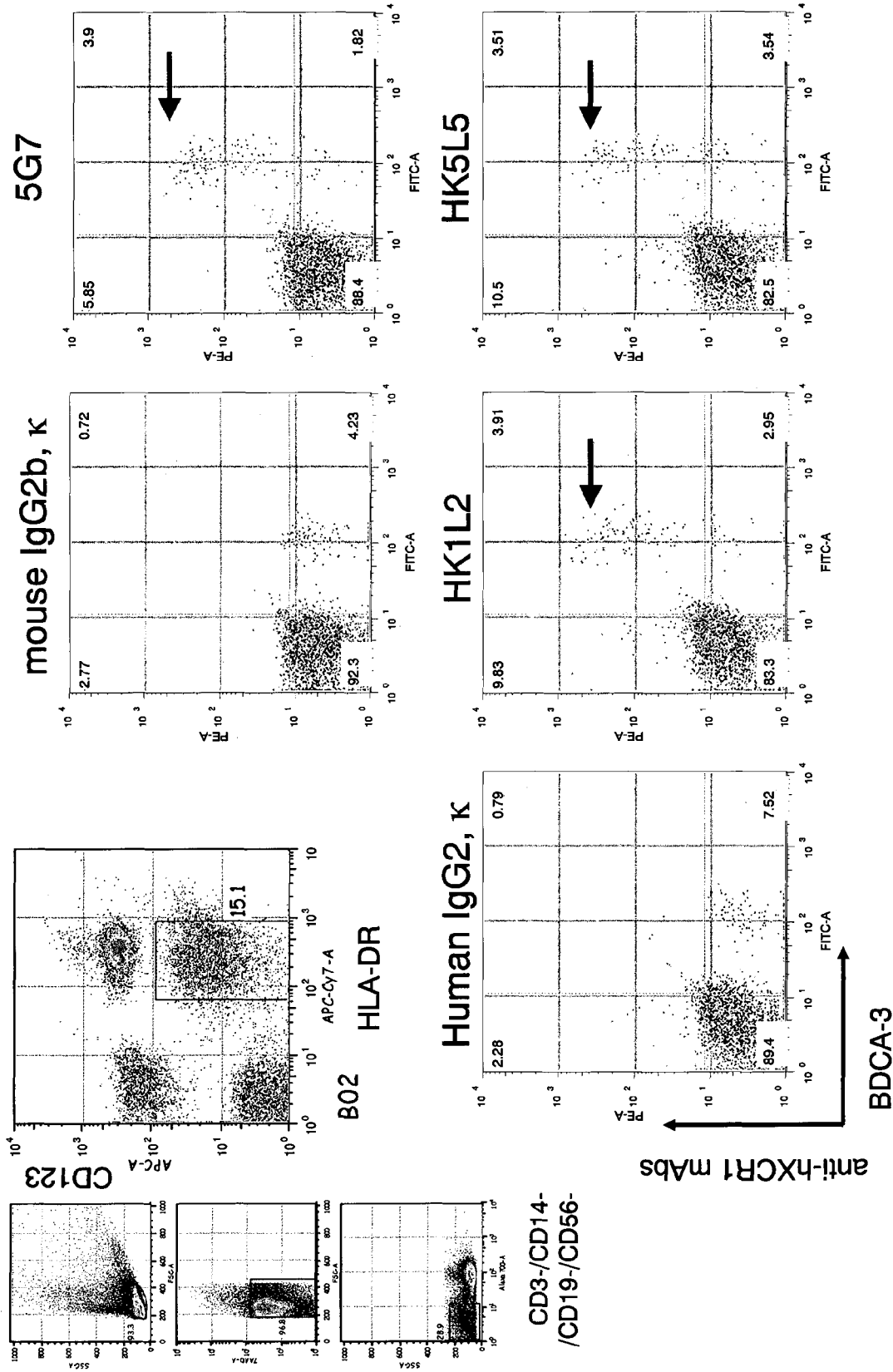
FIG. 4 shows the results of FACS analysis of the reactivity of mouse anti-human XCR1 antibody (5G7) and humanized anti-human XCR1 antibodies (HK1L2 and HK5L5) to human BDCA3+ dendritic cells.

As is the case with parent antibody 5G7, the humanized antibodies (HK1L2 and HK5L5) selectively reacted to BDCA3+ dendritic cells expressing human XCR1 (FIG. 4).

(3) Neutralizing Activity of Humanized Anti-Human XCR1 Antibodies (HK1L2 and HK5L5) on Human Lymphotactin-Induced Migration of Human XCR1-Expressing Cells The neutralizing activity of these humanized antibodies was evaluated in parallel with parent antibody 5G7 and a chimeric antibody by in vitro chemotaxis assay as described above.

Figure 5:
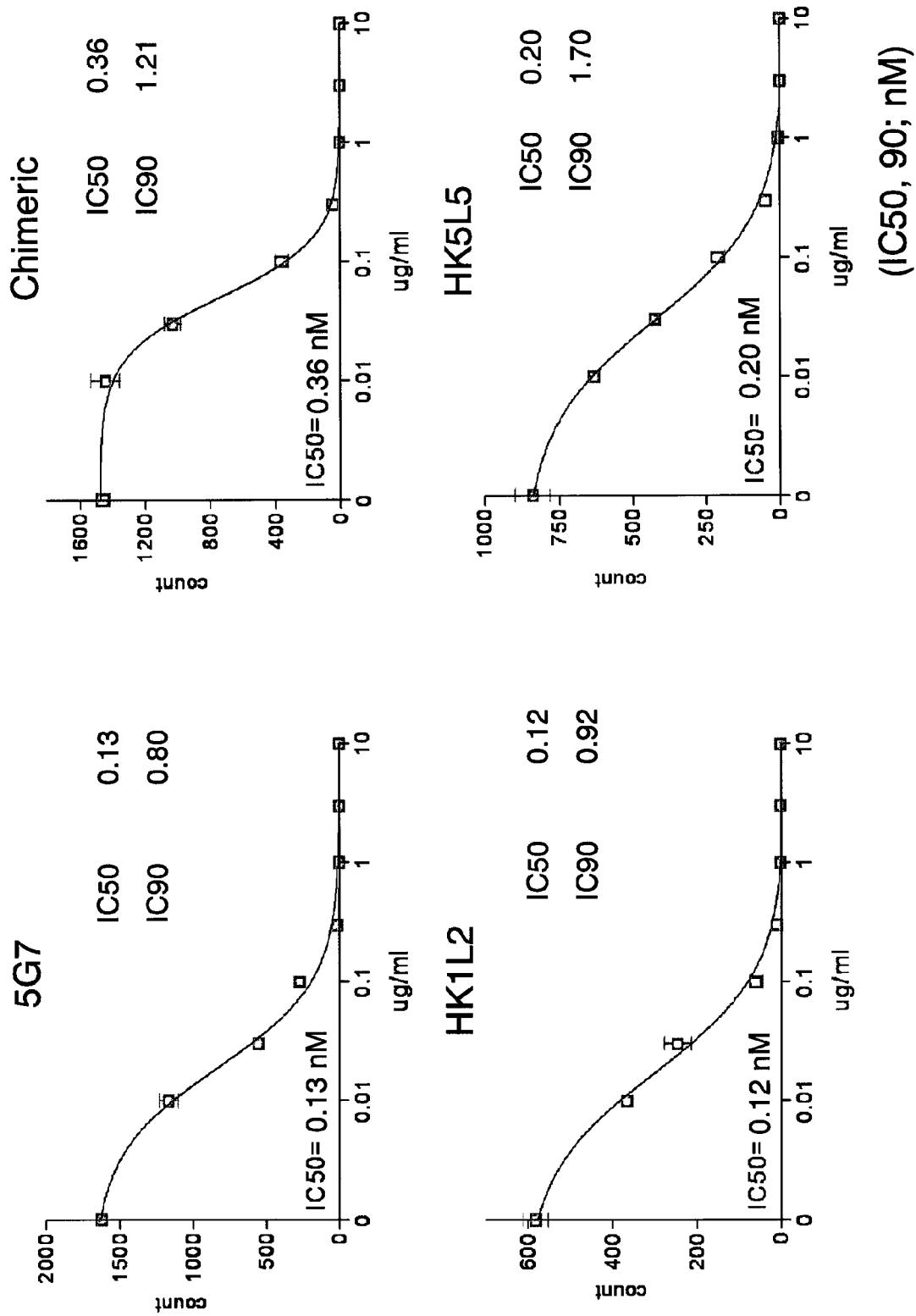
FIG. 5 shows the analysis results of a chemotaxis assay of the neutralizing activity of the humanized anti-human XCR1 antibodies (HK1L2 and HK5L5) on human lymphotactin-induced migration of human XCR1-EGFP-expressing B300.19 cells, in parallel with the neutralizing activity of their parent mouse anti-human XCR1 antibody (5G7) and its chimeric antibody.

In comparison with parent antibody 5G7, both humanized antibodies maintained the neutralizing activity. FIG. 5 shows the typical pattern of concentration-dependent inhibition.

IC$_{50}$ and IC$_{90}$ values were calculated from three independent experiments. Table 16 shows these values as the mean±standard error.

TABLE 16

Neutralizing Activity of Humanized Antibodies (HK1L2 and HK5L5) in Chemotaxis Assay

|  | Mouse mAb Mean ± S.E. | Chimeric mAb Mean ± S.E. | | |
| --- | --- | --- | --- | --- |
| IC$_{50}$ (nM) | 0.23 ± 0.120 | 0.27 ± 0.101 | | |
| IC$_{90}$ (nM) | 1.31 ± 0.452 | 1.52 ± 0.755 | | |
|  | Assay-1 | -2 | -3 | Mean ± S.E. |
| HK1L2 | | | | |
| IC$_{50}$ (nM) | 0.10 | 0.25 | 0.12 | 0.16 ± 0.081 |
| IC$_{90}$ (nM) | 0.66 | 1.01 | 0.92 | 0.86 ± 0.182 |
| HK5L5 | | | | |
| IC$_{50}$ (nM) | 0.52 | 0.36 | 0.20 | 0.36 ± 0.160 |
| IC$_{90}$ (nM) | 2.30 | 3.15 | 1.70 | 2.38 ± 0.729 |

Next, the neutralizing activity of humanized antibodies (HK1L2 and HK5L5) was further examined by transendothelial migration assay that used human dendritic cells instead of the human XCR1-expressing B300.19 cells. The transendothelial migration assay was performed using 24-well transwell culture supports (pore 5 pin, Costar, #3421). First, ECV304 cells were suspended in 10% FBS-containing Medium 199 Earle's medium (Invitrogen), and seeded into the upper chamber of the transwell at $2\times10^5$ cells per well, followed by incubation in a 5% CO$_2$ incubator at 37° C. for 3 days. On the day of an assay, ECV304 cells were washed with assay buffer (a mixture of Medium 199 Earle's medium and RPMI 1640 medium at a 1:1 ratio, to which 0.5% BSA and 20 mM HEPES (pH 7.4) were added). Recombinant human lymphotactin dissolved in the assay buffer at a concentration of 1 µg/mL, to which the chimeric antibody, HK1L2, HK5L5, or isotype control antibody human IgG2, κ (Sigma) was added at a concentration of 10 µg/mL, was added to the lower wells at 600 µL/well. Human dendritic cells were concentrated as described above, suspended in the assay buffer to which the chimeric antibody, the humanized antibodies (HK1L2 and HK5L5) and isotype control antibody human IgG2, κ (Sigma) were added at a concentration of 10 µg/mL, and added to the upper wells containing ECV304 cells. After incubation for 4 hours in a 5% CO$_2$ incubator at 37° C., the cells in the transwell were centrifuged at 1,350 rpm for 5 minutes, and migrated cells were collected. The collected cells were stained for 30 minutes on ice, using cell lineage markers, FITC-labeled anti-BDCA3 antibody (Miltenyi, #130-090-513), PE-labeled anti-BDCA1 antibody (BioLegend, #331517), APC-labeled anti-CD123 antibody (Miltenyi, #130-090-901), and APC-labeled anti-HLA-DR antibody (BioLegend, #307617). 170 µL of each sample was then applied to a FACSCanto II cell analyzer (BD Bioscience) to count the number of cells.

Figure 6:
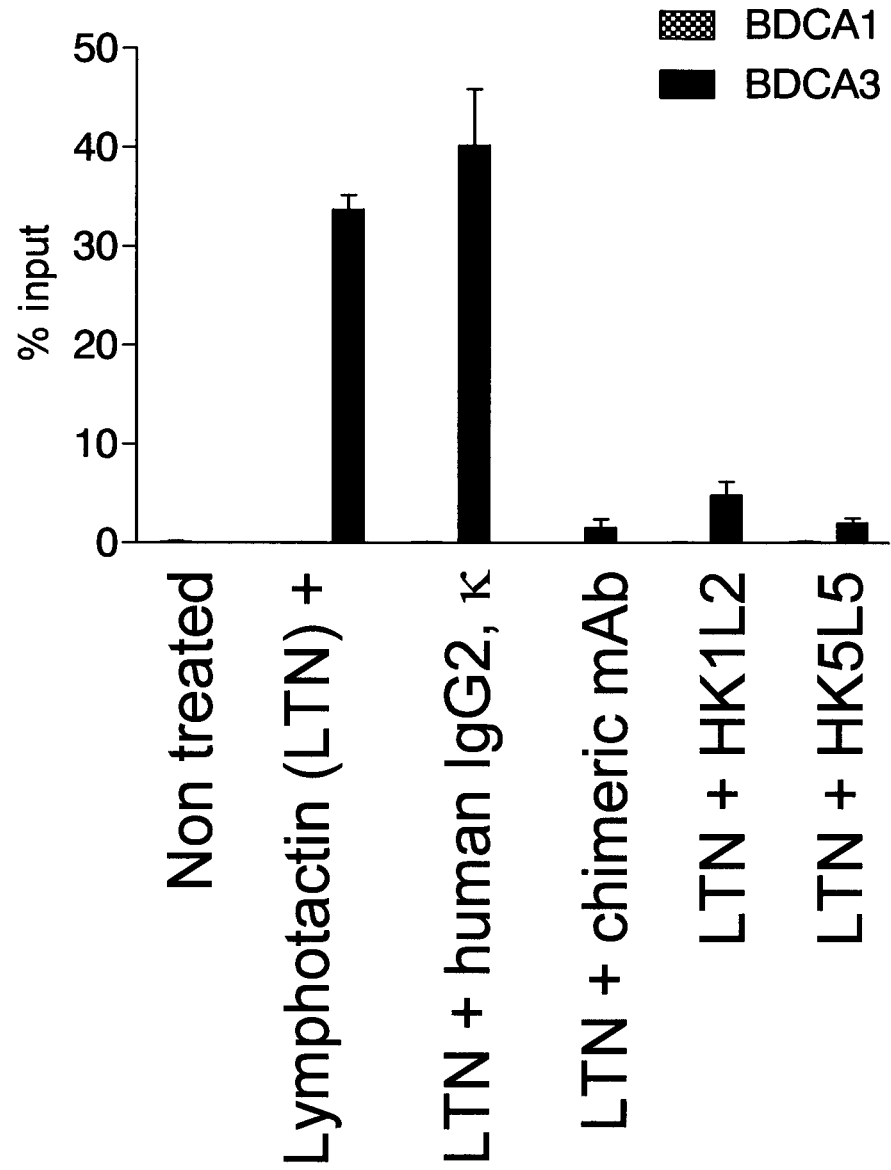
FIG. 6 shows the analysis results of a transendothelial migration assay of the neutralizing activity of the humanized anti-human XCR1 antibodies (HK1L2 and HK5L5) and a chimeric antibody on human lymphotactin-induced migration of human BDCA3+ dendritic cells, in parallel with an isotype control antibody (human IgG2, κ).

Both humanized antibodies inhibited migration of BDCA3+ dendritic cells, as is the case with the chimeric antibody (FIG. 6).

Example 3

Pharmacological Effect of Mouse Anti-XCR1 Antibody

Pharmacological effect of anti-human XCR1 mouse monoclonal antibody (5G7) prepared in Example 2 above was confirmed using a mouse model of delayed-type contact dermatitis (DTH).

(1) Effect of Mouse Anti-Human XCR1 Antibody on Ear Swelling of DNFB (Dinitrofluorobenzene)-Sensitized Mice Experimental Method 1. Sample Mice Human XCR1 knock-in mice (mice whose XCR1 gene has been replaced with human XCR1 gene) on C57BL/6 background between the ages of 7 weeks and 12 weeks were used for the experiment.

2. Method for Preparing DNFB for Sensitization and DNFB for Induction

DNFB for sensitization and induction was prepared by mixing DNFB to a 4:1 mixture of acetone and olive oil to obtain a concentration of 0.5%. Further, a 4:1 mixture of acetone and olive oil was used as a control solution for induction.

3. Method for Administering DNFB

The abdominal hair of the mice was shaved to expose the skin, and 50 µL of 0.5% DNFB for sensitization was applied thereto. On the following day, 50 µL of 0.5% DNFB was applied again to the same site. 4 days after the application, 25 µL of 0.5% DNFB for induction was applied to the front side of the right ear of the mice. At the same time, as a control, 25 µL of the control solution obtained by mixing acetone and olive oil at a 4:1 ratio was applied to the front side of the left ear of the mice.

4. Method for Administering Antibodies

Anti-human XCR1 mouse monoclonal antibody (5G7) and its control antibody, i.e., mouse IgG (Jackson Laboratory), were prepared in PBS to a final concentration of 2 mg/mL. The day when the first sensitization was conducted was defined as Day 0. Each of the above antibodies was intraperitoneally administered into the mice in an amount of 250 µL/mouse (500 ug/mouse) on Day −1, Day 1, and Day 4.

5. Method for Measuring the Ear Swelling of DNFB-Sensitized Mouse Model

On the first day and the following day, the mice were sensitized by applying 50 µL of 0.5% DNFB to the exposed skin of the abdomen. 4 days after the sensitization, the ear thickness was measured using a caliper. After measurement, 25 µL of 0.5% DNFB was applied to the front side of the right ear of the mice for induction. Further, as a control, 25 µL of the control solution formed by mixing acetone and olive oil at a 4:1 ratio was applied to the left ear of the mice. The ear thickness was measured 24 hours and 48 hours after induction. The swelling was determined by converting measured values by the following formula.

Formula $$\text{Ear thickness changed by DNFB(swelling: mm)} = ([A]-[B])-([C]-[D])$$

[A]: thickness of right ear after induction (mm)
[B]: thickness of right ear before induction (mm)
[C]: thickness of left ear after application of control solution (mm)
[D]: thickness of left ear before application of control solution (mm)

Experimental Results and Analysis

Figure 8:
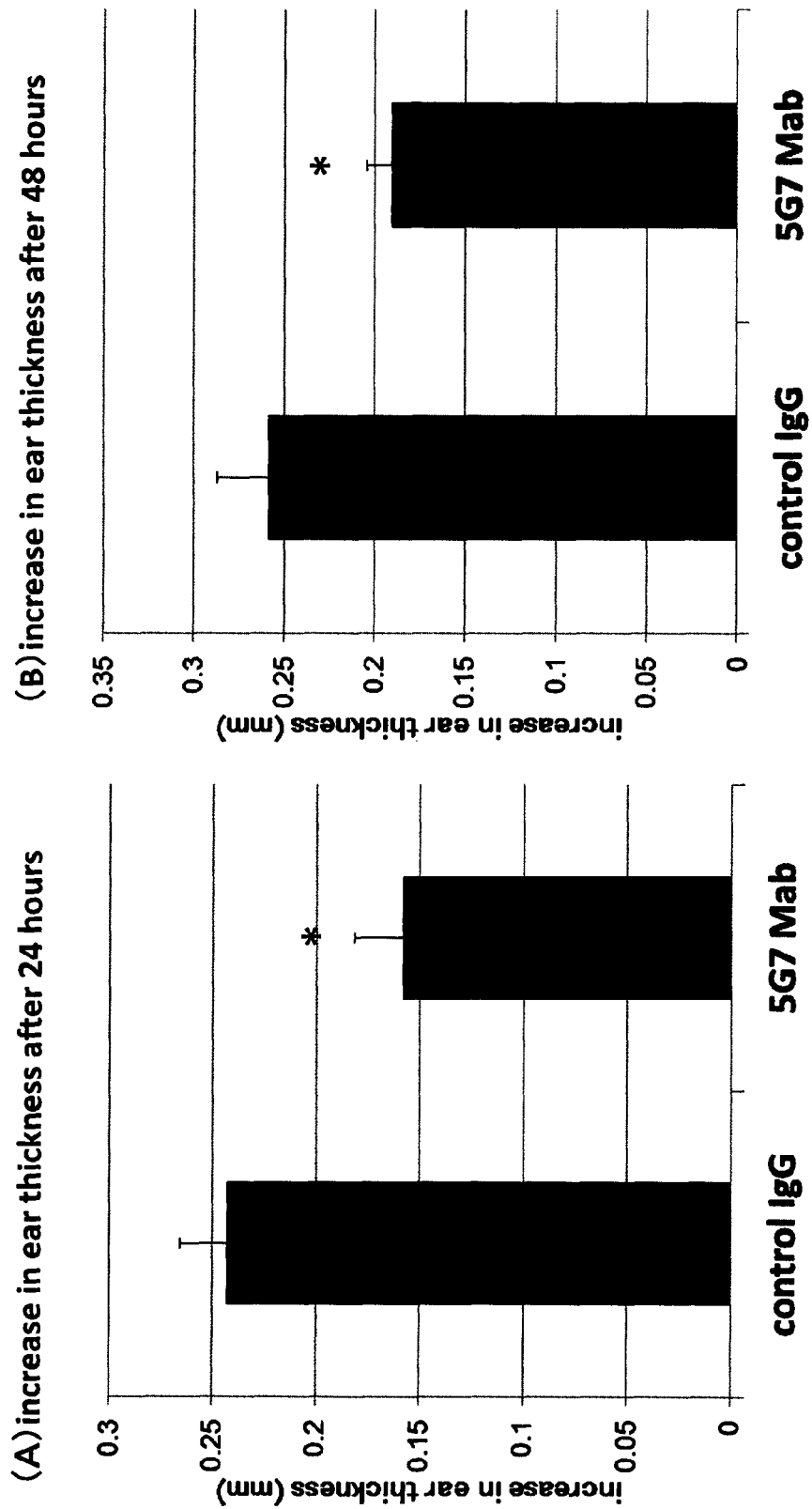
FIG. 8 shows a pharmacological effect of the mouse anti-human XCR1 antibody (5G7) of the present invention on a mouse model of delayed-type contact dermatitis (DTH).

FIG. 8 clearly shows a significant suppression of ear swelling 24 after induction by DNFB in the mice administered with anti-human XCR1 mouse monoclonal antibody (5G7), compared to the mice administered with the control antibody (FIG. 8A). The effect also showed significant suppression in a similar manner 48 hours after induction by DNFB (FIG. 8B).

Although the antibody was systemically administered intraperitoneally, the swelling was suppressed in the ear induced by DNFB. Therefore, it is presumed that the antibody transferred from the abdominal cavity into the blood and, along with the blood flow, reached an inflammatory site or a lymph node, where the antibody demonstrates the effect of suppressing ear swelling.

This suggests that the antibodies of the present invention have a specific effect on the inflammatory site in a site-specific manner.

Example 4

Reactivity of Mouse Anti-Human XCR1 Monoclonal Antibody (5G7) to Various Human Chemokine Receptors The reactivity of mouse anti-human XCR1 monoclonal antibody (5G7) to various human chemokine receptors was evaluated by FACS analysis. Parent B300.19 cells and human chemokine receptor-EGFP-expressing B300.19 cells (XCR1, CXCR1, CXCR3, CXCR4, CXCR5, CXCR6, CCR1, CCR2, CCR3, CCR4, CCR5, CCR6, CCR7, CCR8, CCR9, CCR11, or CX3CR1, and) were suspended in a FACS buffer (PBS⁻ (Sigma) containing 1% fetal bovine serum). The cells were blocked for 20 minutes on ice with a blocking buffer (a FACS buffer containing 100 μg/mL of human immunoglobulin). The cells were then incubated for 30 minutes on ice with the blocking buffer containing 5G7 or mouse isotype control antibody IgG2b (eBioscience, #14-4732-82) at a concentration of 10 μg/mL. The cells were washed three times with the FACS buffer, and then incubated for 20 minutes on ice with PE-labeled anti-mouse IgG polyclonal antibody (Jackson, #715-116-151, diluted at 1:50 in the blocking buffer). The cells were washed with the FACS buffer three times, and then suspended in the FACS buffer. The fluorescence intensity was measured using a FACSCanto II cell analyzer.

Figure 9:
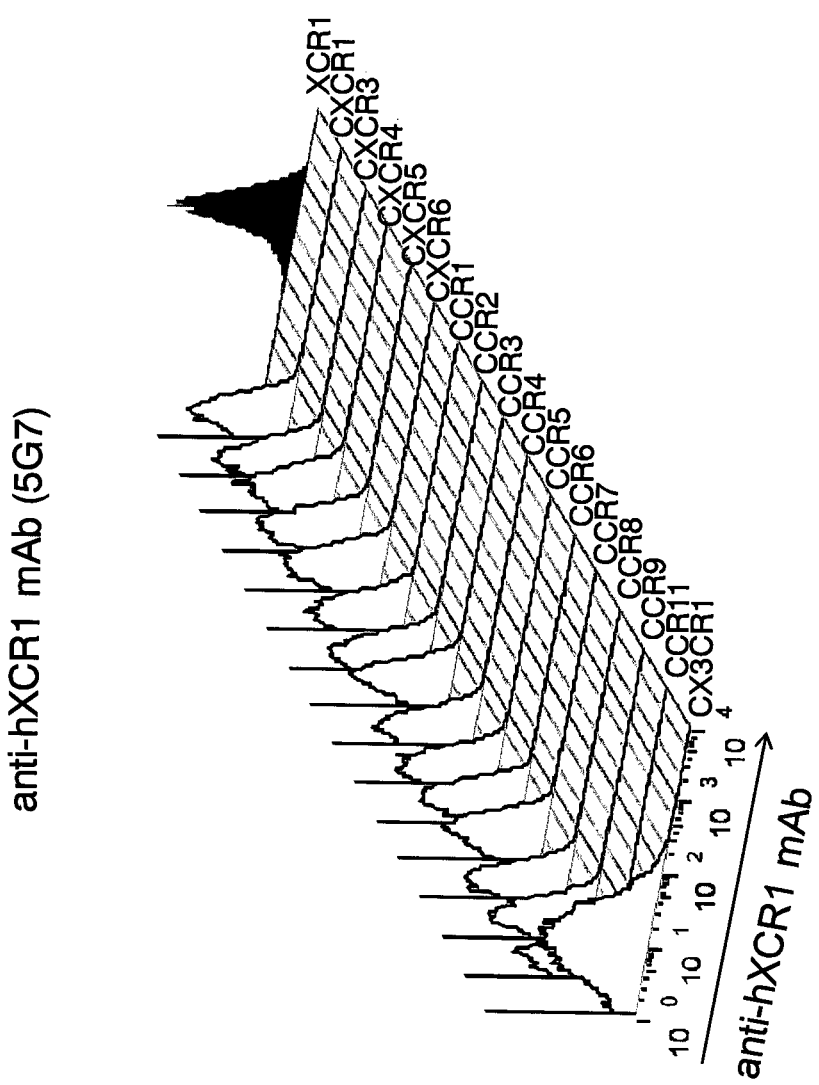
FIG. 9 shows binding specificity of the mouse anti-human XCR1 antibody (5G7) of the present invention to various human chemokine receptors. The abscissa axis of the graph in the figure indicates the fluorescence intensity of phycoerythrin (PE).

Anti-human XCR1 antibody 5G7 showed a high reactivity to human XCR1-EGFP-expressing B300.19 cells. Further, anti-human XCR1 antibody 5G7 showed a very low reactivity to human CX3CR1-EGFP-expressing B300.19 cells, and no reactivity to other human chemokine receptors-EGFP-expressing cells (FIG. 9). On the other hand, mouse isotype control antibody did not show reactivity to any B300.19 cells.

Example 5

Cytotoxicity of Anti-Human XCR1 Antibodies Using Saporin-Conjugated Fab Anti-Mouse IgG Secondary Antibody to Human XCR1 Expressing Cells In order to demonstrate the cytotoxic activity of anti-human XCR1 antibodies to XCR1-expressing cells, cytotoxicity of mouse anti-human XCR1 mAbs to cells on which human XCR1 is exogenously expressing was examined by using saporin-conjugated Fab anti-mouse IgG secondary antibody.

$2 \times 10^3$ cells of B300.19 parent cells or human XCR1-EGFP-expressing B300.19 cells in 80 μL of RPMI1640 (Invitrogen, #11875-093) containing 10% fetal bovine serum (Cell Culture Bioscience, #171012), 100 μg/ml of kanamycin sulfate (Invitrogen, #15160-054) and 50 μM 2-Mercaptoethanol (2-ME, Invitrogen, #21985-023) were added into each well of a 96 well plate. Mouse anti-human XCR1 antibodies (2H6, 5G7, or 11H2), mouse isotype control antibodies, IgG2a, κ (eBioscience, #16-4724-85) or IgG2b, κ (eBioscience, #16-4732-85), were diluted with RPMI1640 containing 10% fetal bovine serum, 100 μg/ml of kanamycin sulfate and 50 μM 2-ME and 10 μl of the diluted antibodies were added to the cells at various concentrations from 0 to 0.17 μg/ml. The cells were then incubated in a 5% $CO_2$ incubator at 37° C. for 20 min. Then, saporin-conjugated Fab anti-mouse IgG (Advanced Targeting Systems, #IT-48) was diluted to 10 μg/ml with RPMI1640 containing 10% fetal bovine serum, 100 μg/ml of kanamycin sulfate and 50 μM 2-ME, and 10 μl of the diluted saporin-conjugated Fab anti-mouse IgG was added to each well at the final concentration of 1 μg/ml. The cells were then incubated in a 5% $CO_2$ incubator at 37° C. for 72 hrs. Then the number of cells in each well was measured by using Cell Count Reagent SF (Nacalai tesque, 07553-15 or -44). The reagent was added to each well and the cells were incubated in a 5% $CO_2$ incubator at 37° C. for 2 or 3 hrs. $OD_{450}$ was then measured with a plate reader (Arvo, PerkinElmer).

Figure 11:
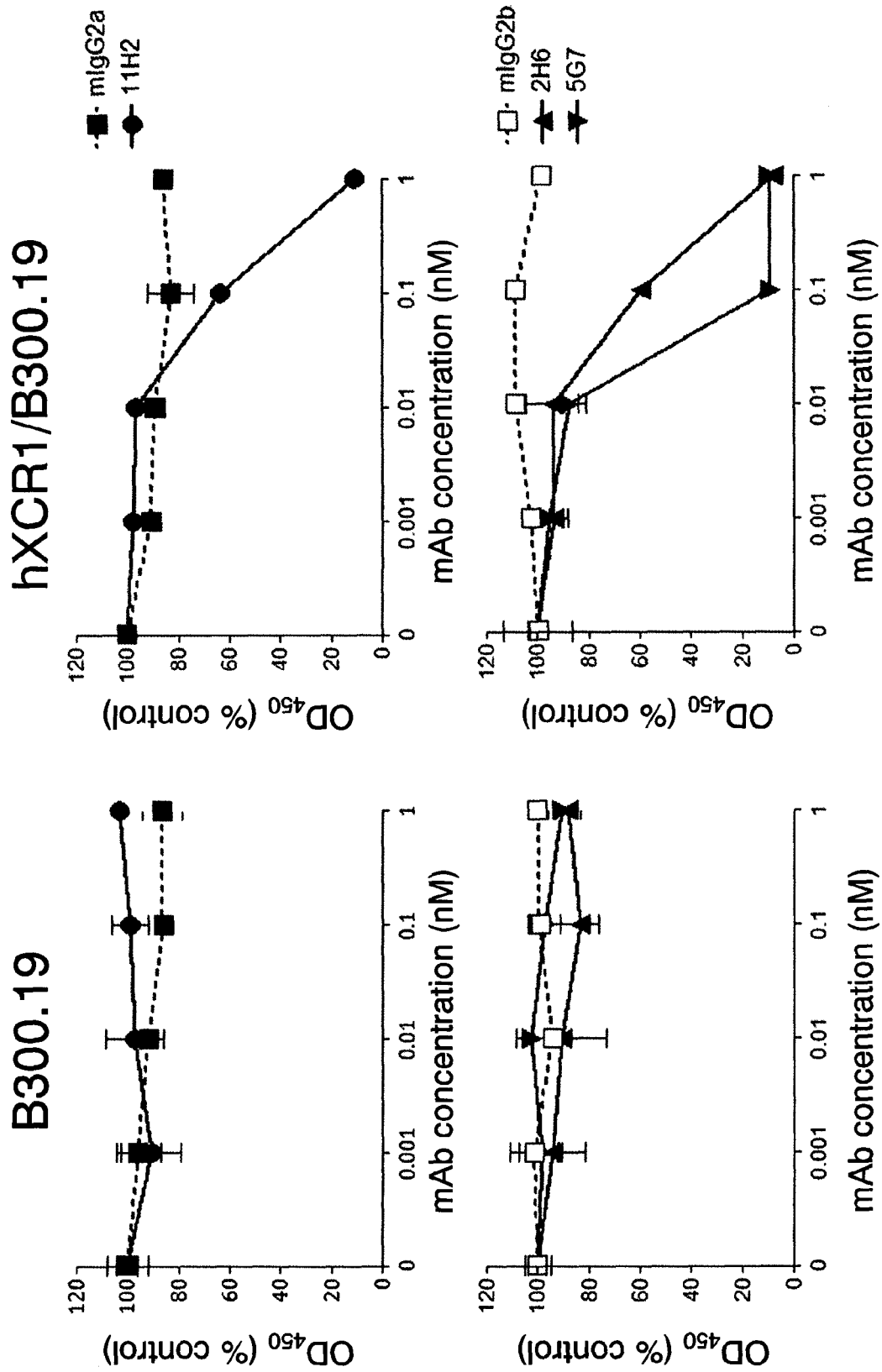
FIG. 11 shows cytotoxity to human XCR1 expressing cells, using the antibodies of present invention.

Mouse anti-human XCR1 antibodies (2H6, 5G7, and 11H2) with saporin-conjugated secondary antibody showed growth suppression of human XCR1-EGFP-expressing B300.19 cells (FIG. 11). The $IC_{50}$ values of 2H6, 5G7, and 11H2 calculated by Graphpad Prism software were 0.141 nM, 0.017 nM, and 0.155 nM, respectively. On the other hand, these antibodies with saporin-conjugated secondary antibody did not show cell growth suppression of parent B300.19 cells. Control antibodies with saporin-conjugated secondary antibody did not suppress cell growth of human XCR1-EGFP-expressing B300.19 cells nor parent B300.19 cells (FIG. 11). These findings indicate that mouse anti-human XCR1 antibodies, 2H6, 5G7, and 11H2, were internalized with saporin-conjugated secondary antibody and acted as an immunotoxin.

Example 6

Effects of 5G7 Mab on Cytotoxitic T Lymphocyte Assay In Vivo

In order to investigate the inhibitory activity of 5G7 Mab on the CTL function, CTL assay was performed.

The engineered hXCR1-knocked-in mice, in which human XCR1 is expressed instead of mouse XCR1, were immunized subcutaneously with ovalbumin (200 μg/head) emulsified with CFA on day 0. The 5G7 Mab or the control mouse IgG (Jackson Laboratory), was intraperitoneally injected at a dose of 500 ug/head on day −1, day 2 and day 5. Six days later, splenocytes from naïve C57BL/6 mice were incubated for 30 min at 37° C. with or without 10 μg/ml $OVA_{257-264}$ peptide (SIINFEKL; MBL).

These peptide-pulsed target and non-target cell populations were labeled with 2.5 and 0.25 μM CFSE (Invitrogen Life Technologies), respectively, then mixed at a 1:1 ratio, and injected intravenously into the immunized mice.

One day after the injection of CFSE-labeled splenocytes, the target cell-killing activity was evaluated using the ratio of CFSE-positive populations in the spleen as follows.

The CFSE-positive cells in the spleen in the immunized mice were detected by flow cytometry, and the CTL activity of each mouse was calculated with the ratio of CFSE$^{high}$ cells and CFSE$^{low}$ cells as follows: CTL activity=(% of CFSE$^{high}$/% of CFSE$^{low}$).

Then, the relative CTL activity was calculated as follows: Relative CTL activity=(CTL activity in each immunized mouse)/(CTL activity in control mouse).

Figure 12:
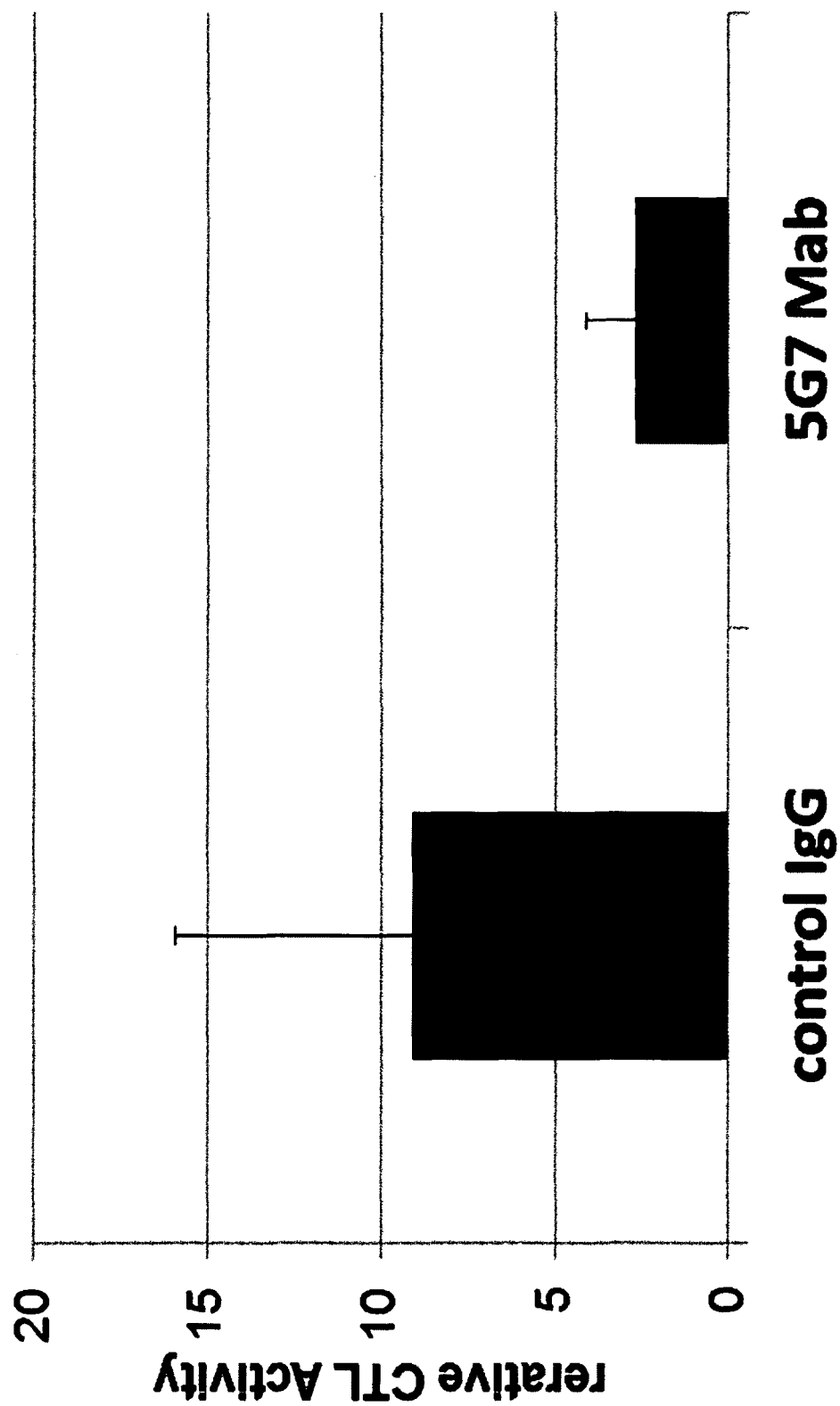
FIG. 12 shows the analysis of the result of cytotoxic T lymphocyte assay of the mouse anti-human XCR1 antibody (5G7) of the present invention.

The results showed that the relative CTL activity in the mice treated with 5G7 Mab showed lower relative CTL activity as compared to that in the mice treated with the control IgG (FIG. 12).

The data indicated the suppression of the in vivo CTL activity by the treatment with anti-XCR1 antibody, and suggested that the treatment with anti-XCR1 antibodies may be beneficial for immune diseases, such as graft rejection, GVHD and tissue injury in autoimmune diseases.

Example 7

Reactivity of Mouse Anti-Human XCR1 Antibodies (2H6, 5G7, and 11H2) to the Chimeric Human/Mouse XCR1-Expressing Cells To determine epitopes of human XCR1 recognized by mouse anti-human XCR1 antibodies (2H6, 5G7, and 11H2), reactivity of these antibodies to chimeric human/mouse XCR1-expressing cells was evaluated.

Because mouse anti-human XCR1 antibodies (2H6, 5G7, and 11H2) reacted to human XCR1 but not to mouse XCR1, a panel of human/mouse XCR1 chimeric receptors was prepared. In this panel, each extracellular domain of human XCR1 was replaced by the homologous region of mouse XCR1, and vice versa. Expression vectors of this panel were constructed using an overlapping extension polymerase chain reaction (PCR) method. Each chimeric receptor-EGFP was expressed in TK-1 cells and mAb reactivity was determined by FACS analysis. Parent TK-1 cells, human XCR1-EGFP-, mouse XCR1-EGFP-, or chimeric XCR1-EGFP-expressing TK-1 cells were suspended in a FACS buffer (PBS$^-$ (Sigma) containing 1% fetal bovine serum). The cells were blocked for 10 minutes on ice with a FACS buffer containing 100 µg/mL of human immunoglobulin. The cells were then incubated for 20 minutes on ice with the anti-human XCR1 antibodies (2H6, 5G7, or 11H2) at various concentrations from 0 to 10 µg/mL, mouse isotype control antibodies, IgG2a (eBioscience, #14-4724-82) or IgG2b (eBioscience, #14-4732-82), at a concentration of 10 µg/mL, or a FACS buffer without antibody. The cells were washed with the FACS buffer three times, and then incubated for 20 minutes on ice with PE-labeled anti-mouse IgG polyclonal antibody (Jackson, #715-116-151, diluted at 1:50 in the FACS buffer) or PE-labeled anti-human XCR1 polyclonal antibody (R&D, #FAB857P, diluted at 2:5 in the FACS buffer, used for cells that had been incubated with the FACS buffer without antibody). The cells were washed with the FACS buffer three times, and then suspended in the FACS buffer. The fluorescence intensity was measured by a FACSCanto II cell analyzer.

Figure 13:
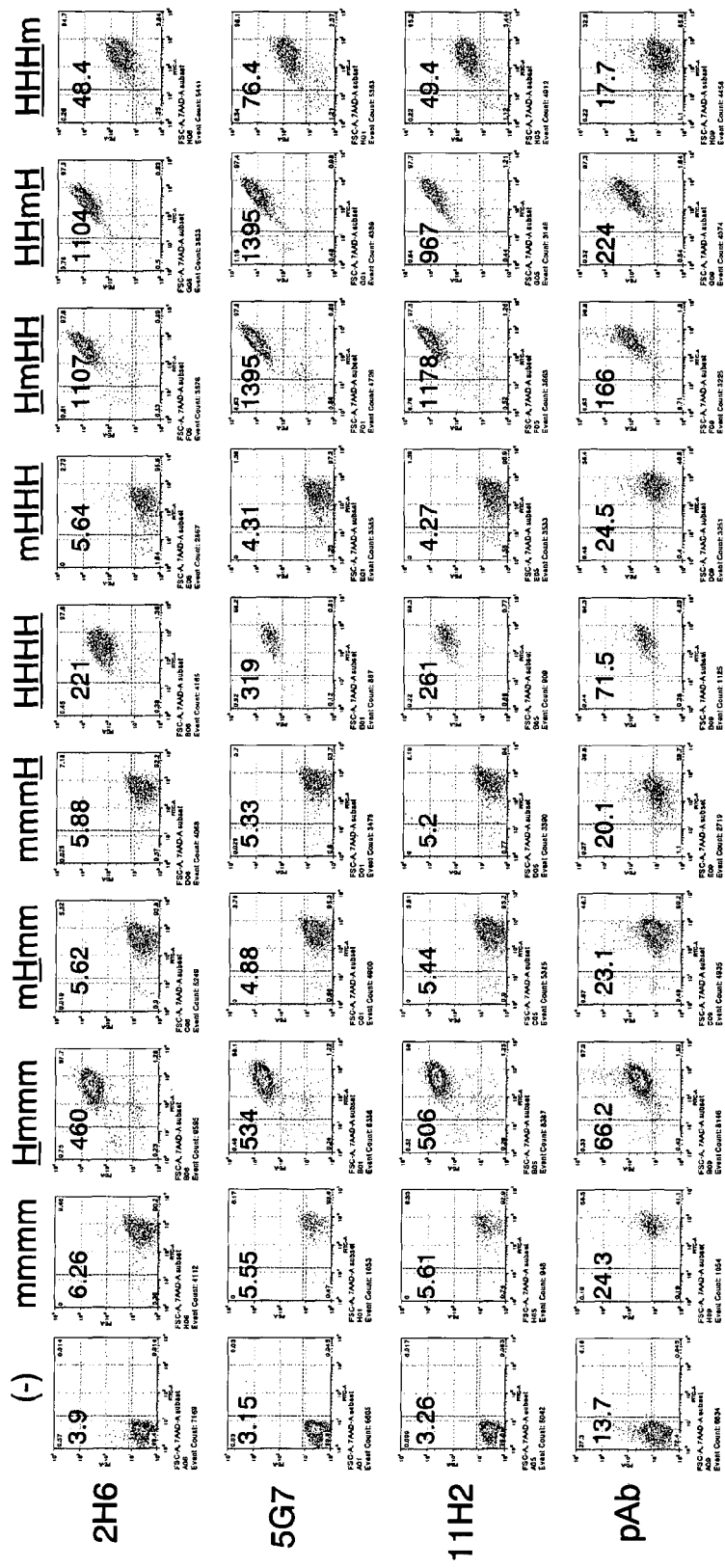
FIG. 13 shows reactivity of mouse anti-human XCR1 antibodies (2H6, 5G7, and 11H2) of the present invention to the chimeric human/mouse XCR1-expressing cells.

Mouse anti-human XCR1 antibodies (2H6, 5G7, and 11H2) showed the reactivity to human XCR1-EGFP-expressing TK-1 cells, but not to parent TK-1 cells or mouse XCR1-EGFP-expressing TK-1 cells (FIG. 13; the origins of the four extracellular domains were designated by four-letter codes (e.g., HHHH is wild-type human XCR1, Hmmm has human N-terminal extracellular domain and mouse first, second, and third extracellular loops, etc.)). These three antibodies showed reactivity to chimeric XCR1s, having the human XCR1 N-terminus, -EGFP-expressing TK-1 cells. Reactivity to chimera receptor, mmHm, was also examined in another experiment, and reactivity was not observed (data not shown).

In contrast, the mouse isotype control antibodies did not show reactivity to any TK-1 cells (data not shown).

Example 8

Mapping of Mouse Anti-Human XCR1 Antibodies (2H6, 5G7, and 11H2)-Binding Sites on the Extracellular Domains of Human XCR1 by Peptide ELISA To define the contact residues of anti-human XCR1 antibodies (2H6, 5G7, and 11H2) on human XCR1 extracellular domains, peptide scan analysis was performed using sets of 12-mer peptides covering the extracellular domains of human XCR1.

Two sets of peptides with biotin and spacer GSGS at N-terminal were synthesized by Sigma. The first set of 13 peptides contained all possible 12-mers from the human XCR1 N terminus, each offset by 2 amino acids. The second set of 13 peptides contained all possible 12-mer from the human XCR1 extracellular loops, each offset by 3 amino acids. Peptides were initially reconstituted in 100% dimethyl sulfoxide and subsequently diluted in 30% dimethyl sulfoxide solution to give a final concentration of 50 µg/mL for direct ELISA.

Streptavidin-coated microtiter plates (Perkin Elmer) were coated with 50 µg/mL of peptide per well in a volume of 50 µL, and incubated at room temperature for 1 hour. The peptide solution was removed and PBS$^-$ containing 4% Block-Ace was added to each well and incubated overnight at 4° C. Each well was washed three times with an ELISA wash buffer (0.02% Tween20 in PBS−). Anti-human XCR1 antibodies (2H6, 5G7, or 11H2) were added to each well in amount of 10 µg/mL, and incubated for 6 hours at room temperature. Each well was washed three times with the ELISA wash buffer. Horseradish peroxidase-conjugated donkey anti-mouse IgG antibody (Jackson, #715-035-150), diluted 1:5,000 in the ELISA wash buffer, was added to each well and incubated for 1 hour at room temperature. Each well was washed three times with the ELISA wash buffer. TMBZ (3,3',5,5' tetramethyl benzidine; Sigma) was added to each well and incubated at room temperature. The reaction was stopped with $2NH_2SO_4$, and $A_{450nm}$ was measured by Arvo plate reader (PerkinElmer).

Figure 14:
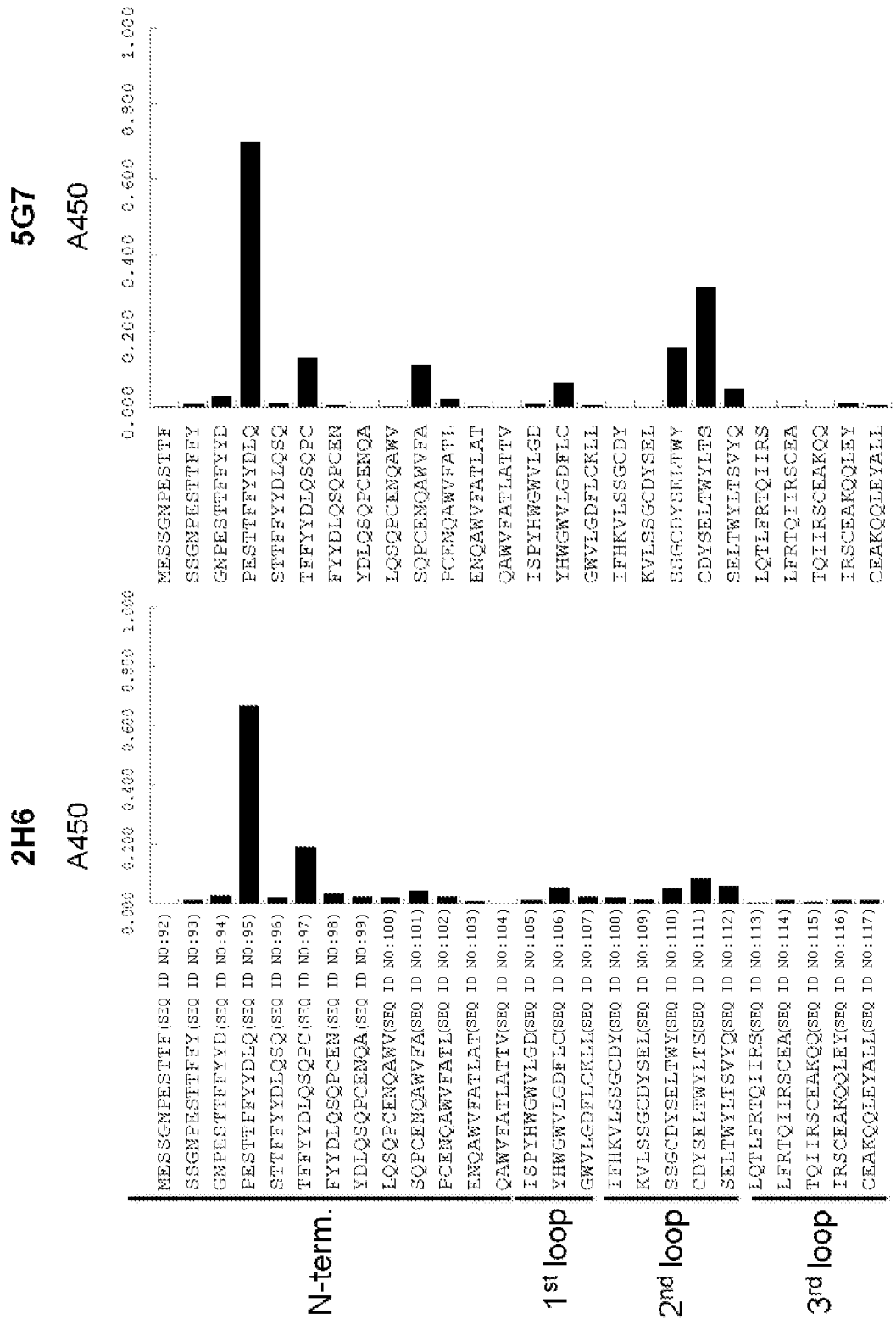
FIG. 14 shows the analysis of result of mapping of mouse anti-human XCR1 antibodies (2H6, and 5G7)-binding sites on human XCR1 extracellular domains by peptide ELISA.

Anti-human XCR1 antibodies 2H6 and 5G7 showed strong binding to one peptide containing $^7$PESTTFFYYDLQ$^{18}$ (SEQ ID NO: 96), and weak binding to $^{11}$TFFYYDLQSQPC$^{22}$ (SEQ ID NO: 110) (FIG. 14). 5G7 also showed weak binding to three non-sequential peptides containing $^{19}$SQPCENQAWVFA$^{30}$ (SEQ ID NO: 101), $^{172}$SSGCDYSELTWY$^{183}$ (SEQ ID NO: 110), and $^{175}$CDYSELTWYLTS$^{186}$ (SEQ 111). On the other hand, 11H2 showed no reactivity to these peptides (data not shown).

Example 9

Mapping of Binding Residues of Mouse Anti-Human XCR1 Antibodies (2H6, 5G7, and 11H2) and Humanized Anti-Human XCR1 Antibodies (HK1L2 and HK5L5) on Human XCR1 Extracellular Domains by Using Alanine Mutants To determine the critical residues of human XCR1 recognized by mouse anti-human XCR1 antibodies (2H6, 5G7, and 11H2) and humanized anti-human XCR1 antibodies (HK1L2 and HK5L5), alanine substitution assay was performed.

A panel of alanine substitution mutants of human XCR1 was prepared. In this panel, each amino acid in [7]PEST-TFFYYDLQSQPCENQAWVFA[30] (SEQ ID NO: 118) and [175]CDYSELTWYLTS[186] (SEQ ID NO: 119) of human XCR1 extracellular regions were replaced by alanine. Expression vectors for alanine substitution mutants were constructed by using site-directed mutagenesis. Each mutant was expressed on B300.19 cells, and antibody reactivity was determined by FACS analysis. Parent B300.19 cells and human XCR1-EGFP- or each alanine mutant human XCR1-EGFP-expressing B300.19 cells were mixed at a 1:1 ratio and suspended in a FACS buffer (PBS⁻ (Sigma) containing 1% fetal bovine serum). The cells were blocked for 10 minutes on ice with a FACS buffer containing 10% rat serum. The cells were then incubated for 20 minutes on ice with mouse anti-human XCR1 antibodies (2H6, 5G7, or 11H2), humanized antibodies (HK1L2 or HK5L5), mouse isotype control antibodies, IgG2a (eBioscience, #14-4724-82) or IgG2b (eBioscience, #14-4732-82), or human isotype control antibody IgG2 (Sigma, #15404), at a concentration of 10 µg/mL; or incubated with a FACS buffer without antibody. The cells were washed with the FACS buffer three times, and then incubated for minutes on ice with PE-labeled anti-mouse IgG polyclonal antibody (Jackson, #715-116-151, diluted at 1:50 in the FACS buffer, used for cells that had been incubated with mouse antibodies), PE-labeled anti-human IgG polyclonal antibody (Jackson, #709-116-149, diluted at 1:50 in the FACS buffer, used for cells which had been incubated with humanized antibodies or human control IgG), or PE-labeled anti-human XCR1 polyclonal antibody (R&D, #FAB857P, diluted at 2:5 in the FACS buffer, used for cells that had been incubated with the FACS buffer without antibody). The cells were washed three times with the FACS buffer, and then suspended in the FACS buffer. The fluorescence intensity was measured using a FACSCanto II cell analyzer (BD Bioscience).

Figure 15:
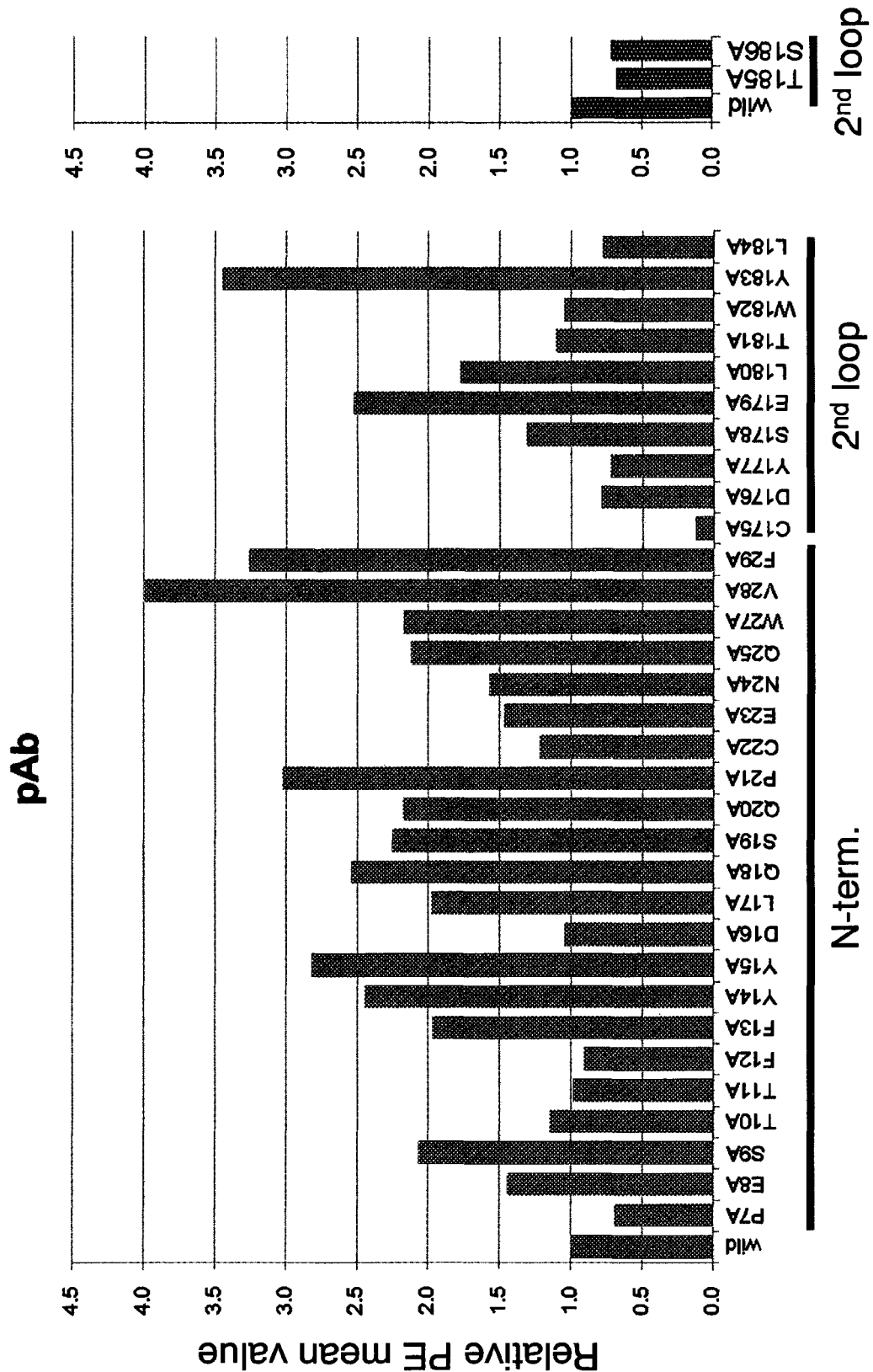
FIG. 15 shows the analysis of the result of mapping of anti-human XCR1 polyclonal antibody-binding sites on human XCR1 extracellular domains by using alanine mutants.
Figure 16:
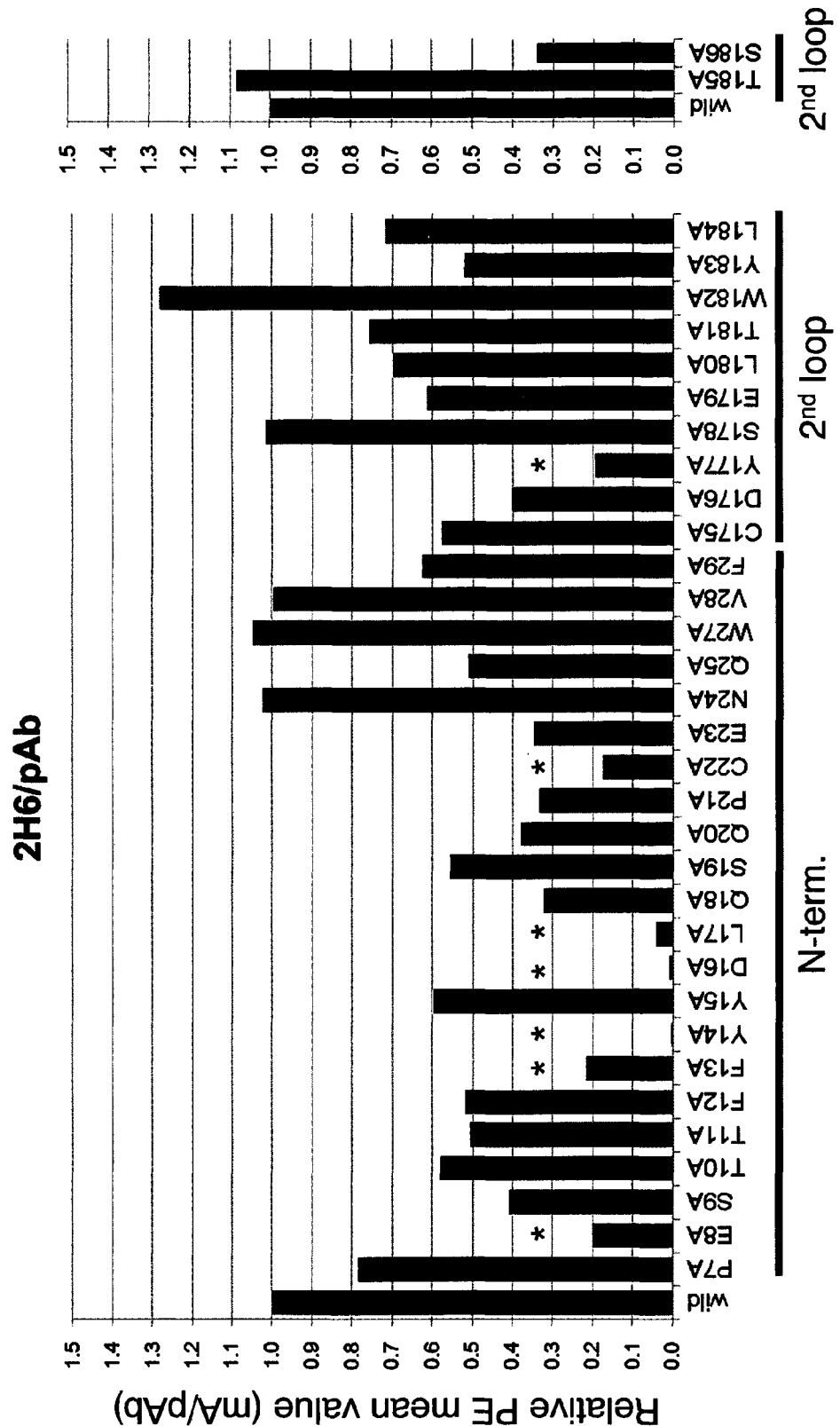
FIG. 16 shows the analysis of the result of mapping of mouse anti-human XCR1 antibody (2H6)-binding sites on human XCR1 extracellular domains by using alanine mutants.
Figure 17:
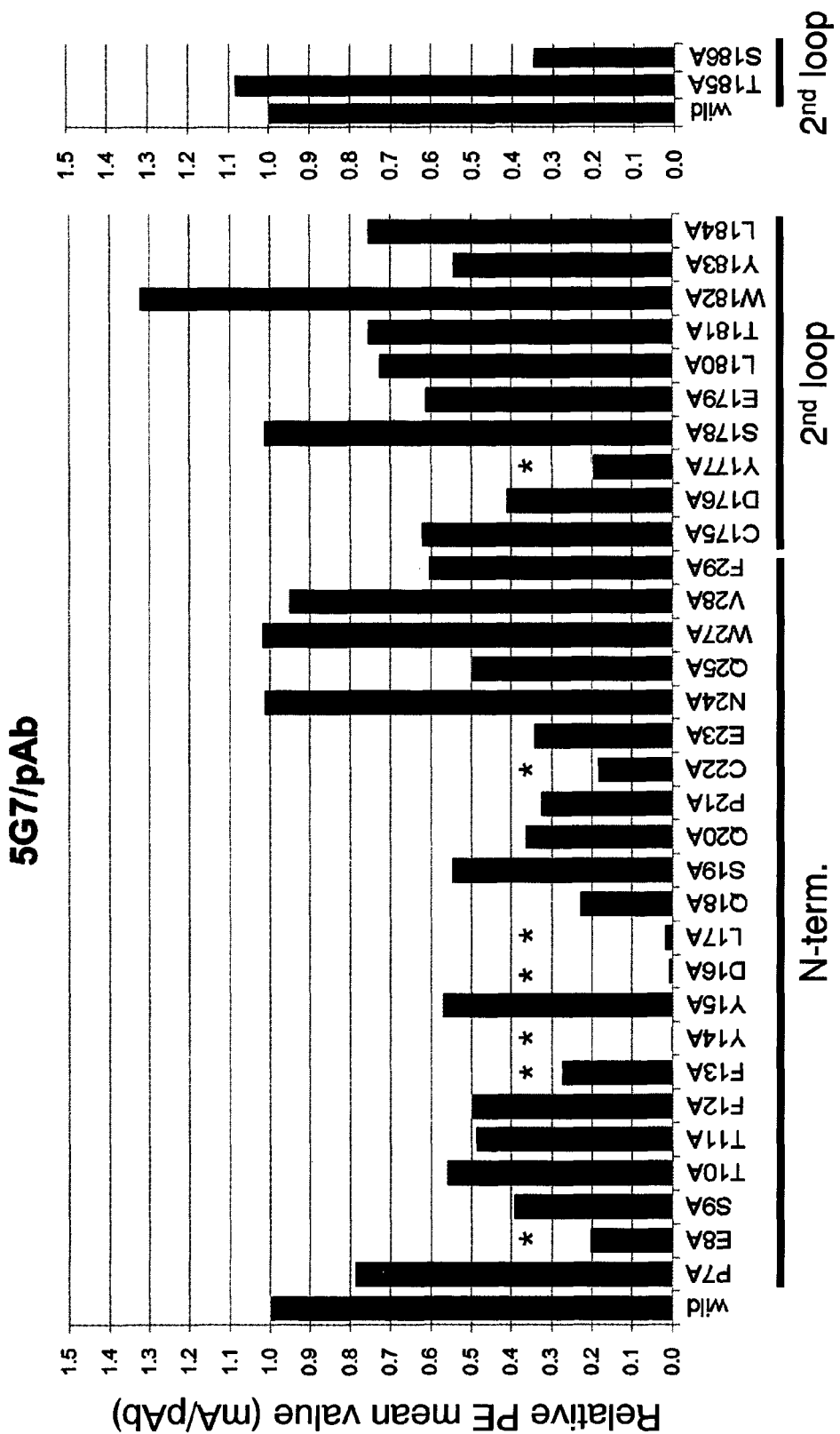
FIG. 17 shows the analysis of the result of mapping of mouse anti-human XCR1 antibody (5G7)-binding sites on human XCR1 extracellular domains by using alanine mutants.
Figure 18:
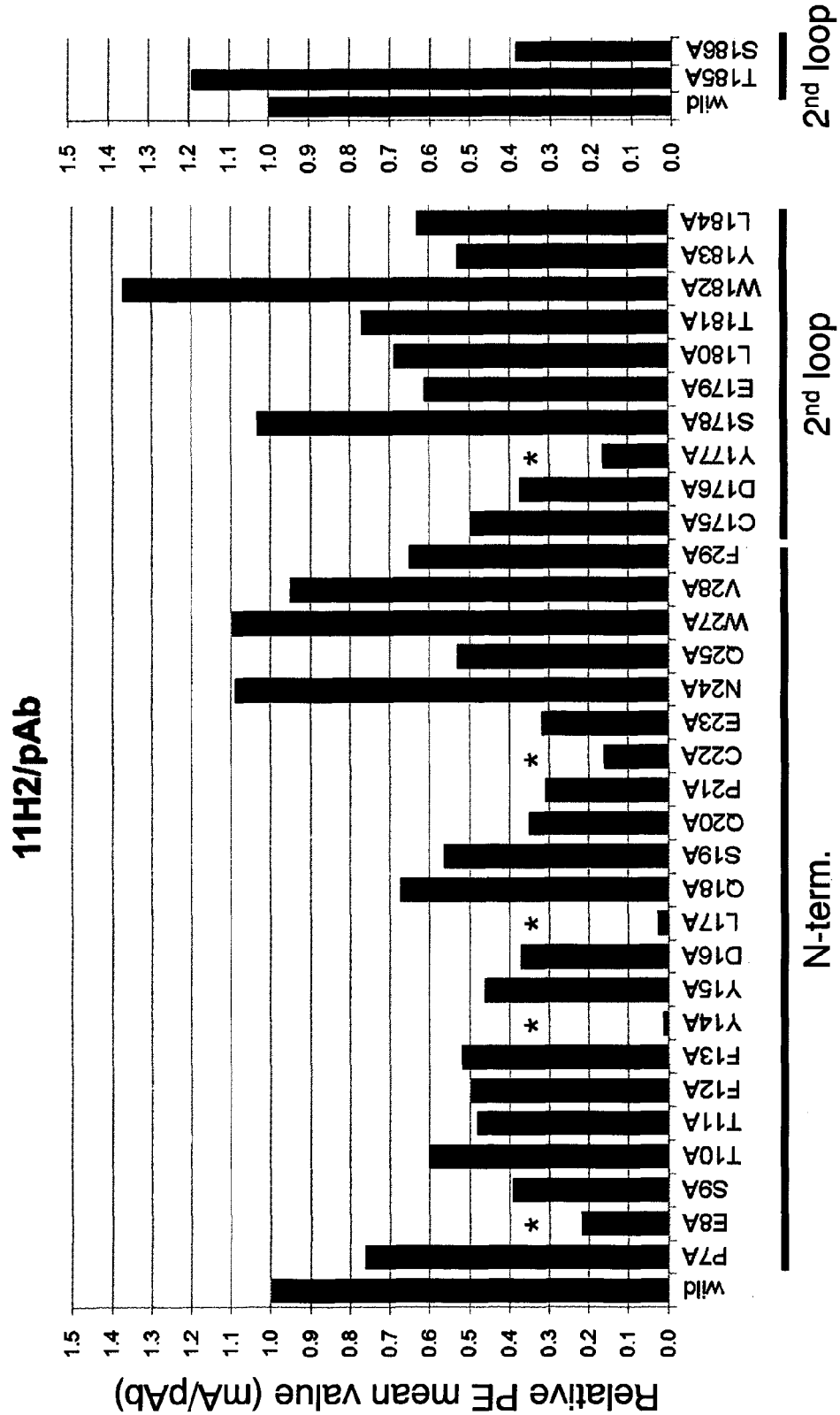
FIG. 18 shows the analysis of the result of mapping of mouse anti-human XCR1 antibody (11H2)-binding sites on human EXR1 extracellular domains by using alanine mutants.
Figure 19:
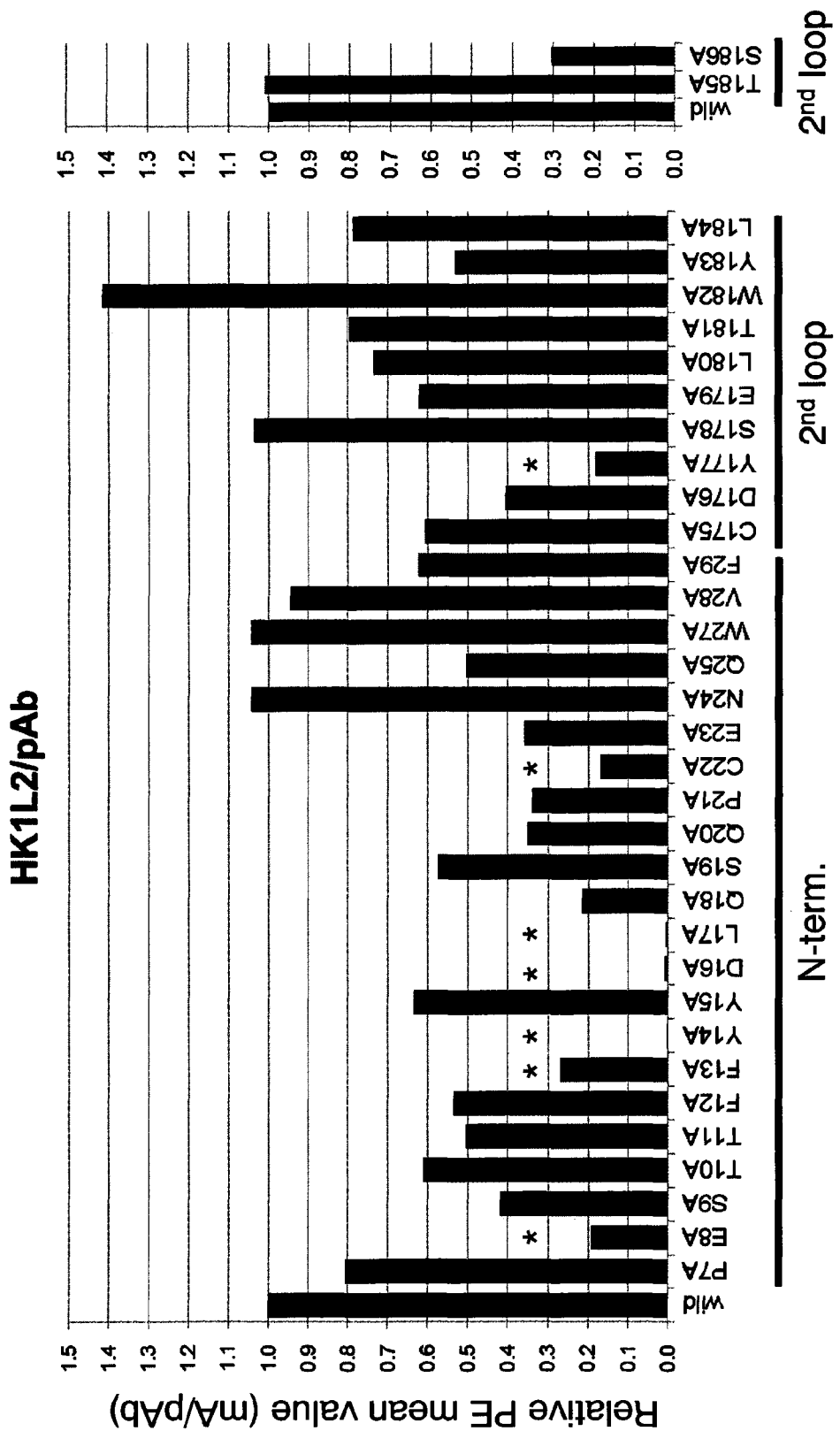
FIG. 19 shows the analysis of the result of mapping of humanized anti-human XCR1 antibody (HK1L2)-binding sites on human XCR1 extracellular domains by using alanine mutants.
Figure 20:
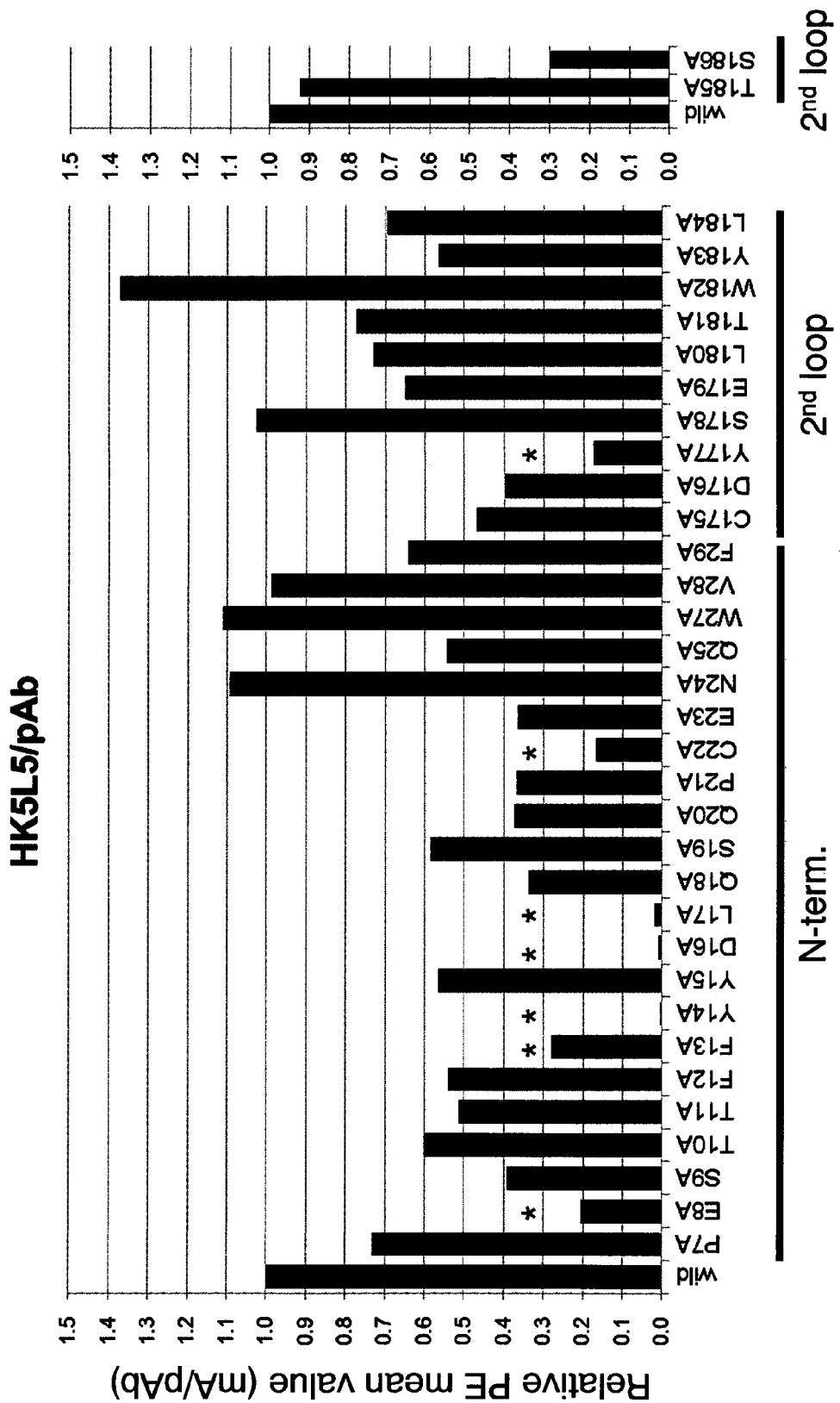
FIG. 20 shows the analysis of the result of mapping of humanized anti-human XCR1 antibody (HK5L5)-binding sites on human XCR1 extracellular domains by using alanine mutants.

Each alanine mutant was detected by PE-labeled anti-human XCR1 polyclonal antibody, except for C175A mutant (FIG. 15). Because expression amounts of each alanine mutants on cell surface were varied among these mutants as shown in FIG. 15, reactivity of antibodies to each alanine mutant was evaluated by a relative PE mean value (mAb/pAb), calculated as per the following procedure. At first, a relative PE mean value for each antibody was calculated by setting the PE mean value, which was obtained by staining of human XCR1-EGFP-expressing B300.19 cells (wild type) using each antibody, as 1.0. The relative PE mean values (mAb/pAb) were then calculated by the following equation: each relative PE mean values for mouse anti-human XCR1 antibodies (2H6, 5G7, or 11H2) or humanized antibodies (HK1L2 or HK5L5) was divided by the relative PE mean values for PE-labeled anti-human XCR1 polyclonal antibody. The results showed that 2H6 (FIG. 16), 5G7 (FIG. 17), HK1L2 (FIG. 19), and HK5L5 (FIG. 20) showed lower reactivity to many alanine mutants in which each residue in N-terminus or $2^{nd}$ loop was replaced with alanine. In particular, no reactivity or weak reactivity to Y14A, D16A, and L17A mutants were observed. Additionally, reactivity to E8A, F13A, C22A, and Y177A were lower among these mutants. Taken together, these results indicate that 2H6, 5G7, HK1L2, and HK5L5 recognize E8, F13, Y14, D16, L17, C22 and Y177 on human XCR1 extracellular domain. 11H2 (FIG. 18) showed similar reactivity to other mAbs except for F13A and D16A, indicating that 11H2 binds to E8, Y14, L17, C22, and Y177.

Example 10

Competition among Mouse Anti-Human XCR1 Antibodies (2H6, 5G7, and 11H2), Recognizing Similar Epitopes, for Binding to Human XCR1-Expressing Cells To determine whether anti-human XCR1 antibodies, recognizing similar epitopes, compete with each other for binding to human XCR1, a competition assay was performed.

The competition assay was performed as per the following procedure. Parent B300.19 cells and human XCR1-EGFP-expressing B300.19 cells were mixed at a 1:1 ratio and suspended in a FACS buffer (PBS⁻ (Sigma) containing 1% fetal bovine serum). The cells were blocked for 10 minutes on ice with the FACS buffer containing 10% rat serum. The cells were then incubated with mouse anti-human XCR1 antibodies (2H6, 5G7, or 11H2), mouse isotype control antibodies, IgG2a (eBioscience, #16-4724-85) or IgG2b (eBioscience, #16-4732-85), at various concentrations from 0 to 10 µg/mL in the FACS buffer for 20 minutes on ice. The cells were then incubated with biotinylated mouse anti-human XCR1 antibody (5G7) at a concentration of 0.3 µg/mL in the FACS buffer for 20 minutes on ice. The cells were washed with the FACS buffer three times, and then incubated for 20 minutes on ice with PE-labeled streptavidin (BD Pharmingen, #554061, diluted with the FACS buffer at a dilution factor of 1:50). The cells were washed three times with the FACS buffer, and then suspended in the FACS buffer. Fluorescence intensity was measured using a FACSCanto II cell analyzer (BD Bioscience).

Figure 21:
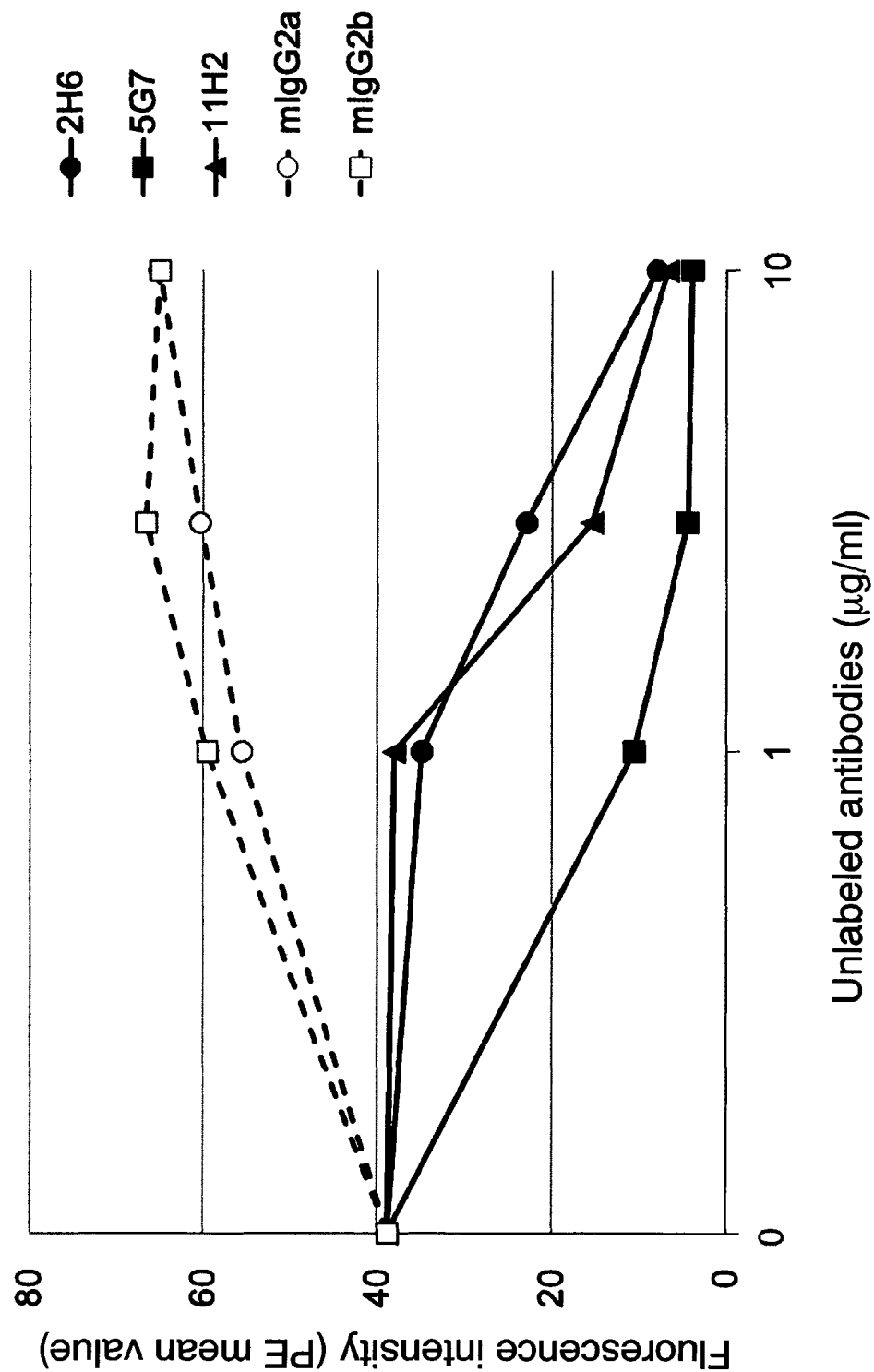
FIG. 21 shows the analysis of the result of the competition among mouse anti-human XCR1 antibodies (2H6, 5G7, and 11H2) for binding to human XCR1-expressing cells.

Binding of biotinylated mouse anti-human XCR1 antibody (5G7) to human XCR1-EGFP-expressing B300.19 cells was competed with unlabeled 5G7 itself, unlabeled 2H6 and 11H2, recognizing similar epitopes on human XCR1 (FIG. 21). On the other hand, control antibodies did not compete with biotinylated antibody (5G7) for binding to human XCR1-EGFP-expressing B300.19 cells.

Example 11

Reactivity of Mouse Anti-Human XCR1 Monoclonal Antibody, 5G7, and Humanized Anti-Human XCR1 Monoclonal Antibodies, HK1L2 and HK5L5, to Various Human Chemokine Receptors The reactivity of mouse anti-human XCR1 monoclonal antibody, 5G7 and humanized anti-human XCR1 monoclonal antibodies, HK1L2 and HK5L5 to various human chemokine receptors were evaluated by FACS analysis.

Parent B300.19 cells and human chemokine receptor-EGFP-expressing B300.19 cells (XCR1, CXCR1, CXCR3, CXCR4, CXCR5, CXCR6, CCR1, CCR2B, CCR3, CCR4, CCR5, CCR6, CCR7, CCR8, CCR9, CCR11, or CX3CR1) were suspended in a FACS buffer (PBS⁻ (Sigma) containing 1% fetal bovine serum) at a concentration of 1×10⁶ cells/mL and aliquots of 100 dal were dispensed into wells of a 96 well round bottom plate. The cells were then centrifuged, and supernatants were discarded. Mouse anti-human XCR1 mAb, 5G7, mouse isotype control antibody IgG2b (eBioscience, #14-4732-82), humanized anti-human XCR1 monoclonal antibodies, HK1L2 and HK5L5, and control human IgG (Mitsubishi, #128-26053-9) were diluted with the FACS buffer at a concentration of 5 µg/mL. PE-labeled goat anti-human XCR1 polyclonal antibodies (R&D, #FAB857P, and LifeSpan BioScience, #LS-C76885) were diluted with the FACS buffer at the dilution factors of 2:5 and 1:5, respectively. Fifty μL of the diluted antibodies were added to each well, and the cells were incubated for 20 minutes on ice. The cells were then washed three times with the FACS buffer. PE-labeled anti-mouse IgG polyclonal antibody (Jackson, #715-116-151, diluted with the FACS buffer at a dilution factor of 1:50) was added to the cells that had been incubated with 5G7 or mouse isotype control antibody. PE-labeled anti-human IgG polyclonal antibody (Jackson, #709-116-149, diluted with the FACS buffer at a dilution factor of 1:50) was added to the cells that had been incubated with HK1L2, HK5L5 or human control IgG. The FACS buffer was added to the cells that had been incubated with anti-hXCR1 polyclonal antibodies. The cells were then incubated for 20 minutes on ice. The cells were washed with the FACS buffer three times, and then suspended in the FACS buffer. Fluorescence intensity was measured using a FACSCanto II cell analyzer, and expressed as a delta PE mean value. The delta PE mean value was calculated by subtracting background PE mean value from each PE mean value, which was obtained by staining each cell line with each antibody.

Figure 22:
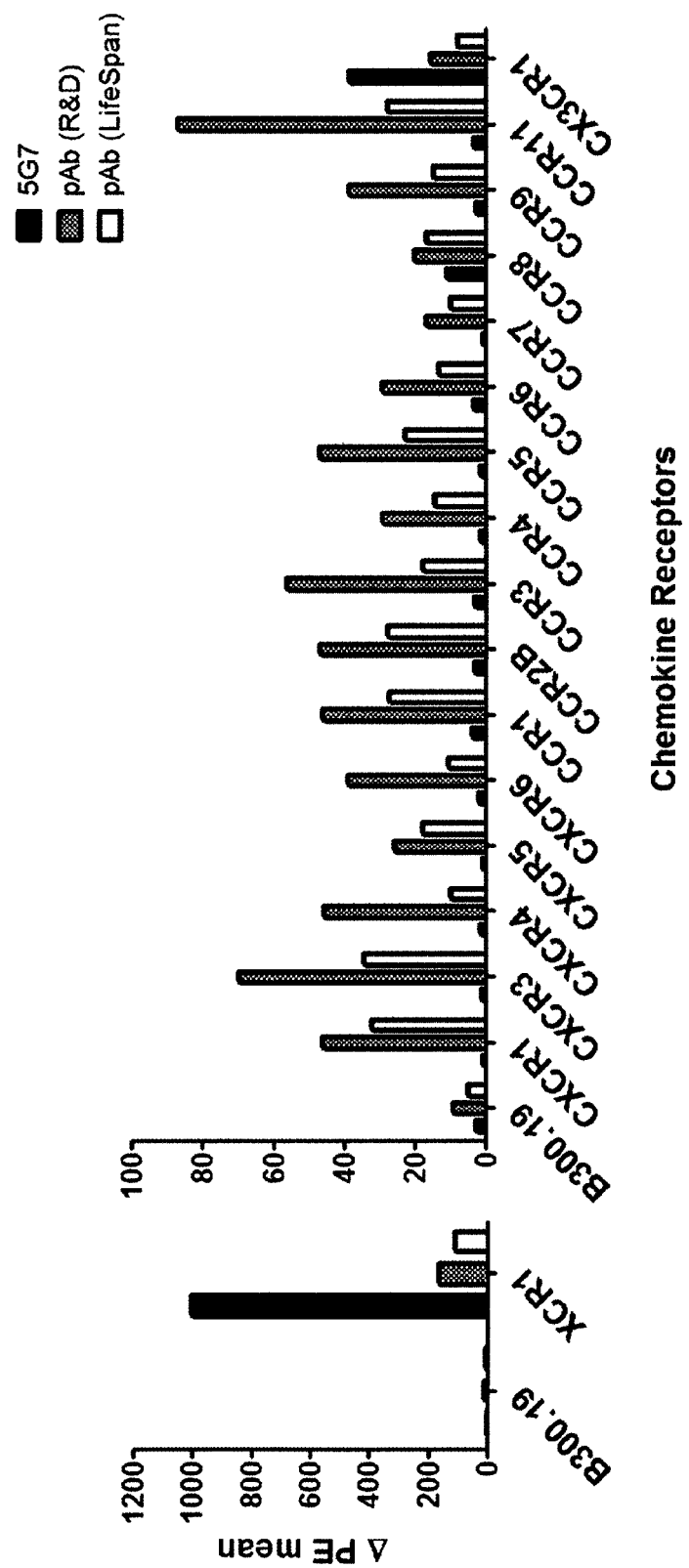
FIG. 22 shows binding specificity of the mouse anti-human XCR1 monoclonal antibody (5G7) and commercial goat anti-human XCR1 polyclonal antibody to various human chemokine receptors. The abscissa axis of the graph in the figure indicates the fluorescence intensity of phycoerythrin (PE).
Figure 23:
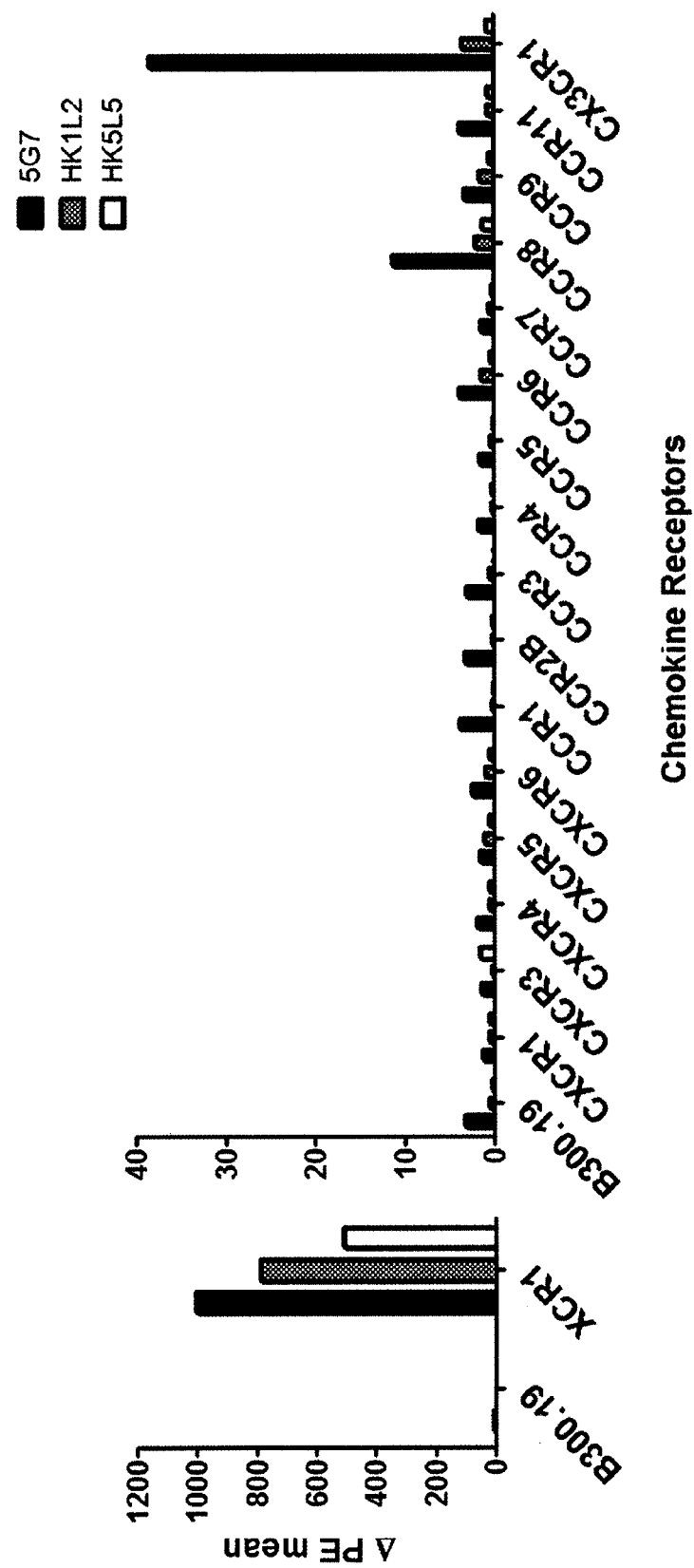
FIG. 23 shows binding specificity of the mouse anti-human XCR1 monoclonal antibody (5G7) and humanized anti-human XCR1 monoclonal antibodies (HK1L2 and HK5L5) to various human chemokine receptors. The abscissa axis of the graph in the figure indicates the fluorescence intensity of phycoerythrin (PE).

Mouse anti-human XCR1 antibody, 5G7 selectively reacted to human XCR1-EGFP-expressing B300.19 cells except for human CX3CR1-EGFP-expressing cells (FIG. 22). On the other hand, goat anti-human XCR1 polyclonal antibodies reacted to various human chemokine receptor-EGFP-expressing cells in addition to human XCR1-EGFP-expressing cells (FIG. 22). Humanized anti-human XCR1 antibodies, HK1L2 and HK5L5 showed reduced reactivity to human CX3CR1-EGFP-expressing cells in spite of their high reactivity to human XCR1-EGFP-expressing cells (FIG. 23).

Example 12

Effect of 5G7 Mab on *Mycobacterium butyricum*-Induced DTH Response

It is known that a delayed-type hypersensitivity (DTH) response is one of the main mechanisms causing autoimmune diseases such as thyroiditis, rheumatoid arthritis and type 1 diabetes when this response is directed against self-antigens (Actor, J. K. and Ampel, N. M. (December 2009) Hypersensitivity: T Lymphocyte-mediated (Type IV). In: Encyclopedia of Life Sciences (ELS). John Wiley & Sons, Ltd: Chichester). T cell-Dendritic cell interaction is critical for DTH responses. Thus the inhibition of T cell-DC interaction is believed to be useful to treat those diseases. We investigated the effect of the anti-human XCR1, 5G7 Mab, on a model of DTH reaction, *Mycobacterium* (*M.*) *butyricum*-induced DTH response, in human XCR1 knocked-in mice (Mihara, M. et al, Immunology Letters 2002, 84: 223-229; Mohan K et al, Eur. J. Immunol. 2005, 35: 1702-1711).

(Methods)

The engineered hXCR1-knocked-in mice, in which human XCR1 is expressed instead of mouse XCR1, were immunized subcutaneously with heat-killed *M. butyricum* (100 μg/head) with mineral oil on day 0. A 5G7 Mab or a control mouse IgG (Jackson Laboratory), were intraperitoneally injected at the dose of 500 μg/head on day 1, day 3, day 7 and day 9. 10 days after the immunization with *M. butyricum*, the mice were challenged with *M. butyricum* suspended in mineral oil on the right footpad (20 μg/foot, *M. butyricum* challenge), and mineral oil on alone left footpad (control challenge). One day after the challenge injection, the DTH response was evaluated by measuring the footpad thickness of each footpad. The footpad swelling was calculated according to the following formula.

Footpad swelling=([*A*]−[*B*])−([*C*]−[*D*])

[A]=thickness of right footpad after *M. butyricum* challenge
[B]=thickness of right footpad before *M. butyricum* challenge
[C]=thickness of left footpad after control challenge
[D]=thickness of left footpad before control challenge
(Results)

Figure 24:
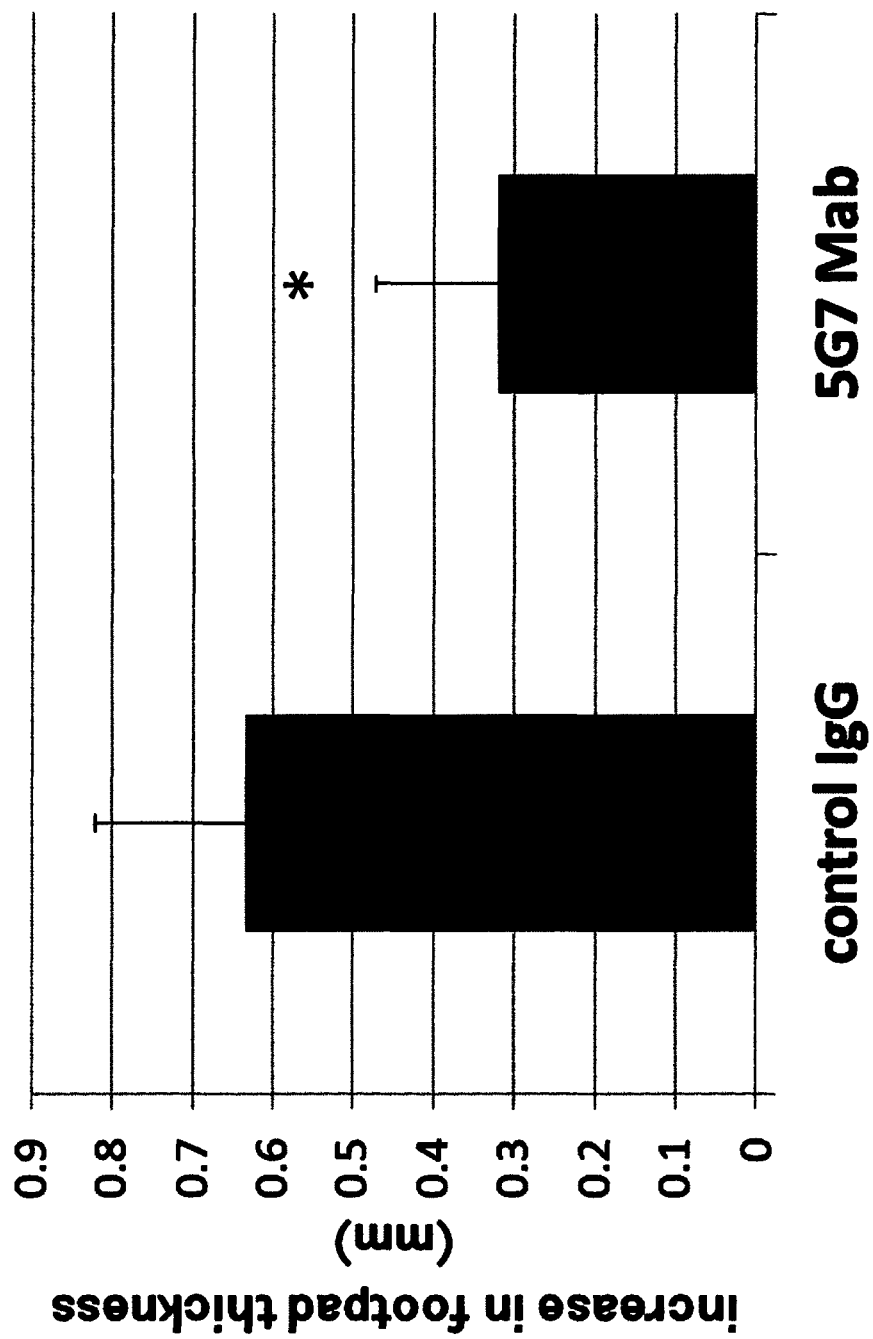
FIG. 24 shows a pharmacological effect of the mouse anti-human XCR1 antibody (5G7) of the present invention on a mouse model of delayed-type contact dermatitis (DTH) induced by *Mycobacterium butyricum*.

The result showed that the *M. butyricum*-induced DTH response in mice treated with 5G7 Mab showed significantly lower DTH response compared to the mice treated with the control IgG (FIG. 24).
(Conclusion)

The data showed the efficacy of anti-XCR1 antibody treatment in the DTH response. It is suggested that the use of anti-XCR1 antibodies may be beneficial in the treatment of DTH-driven autoimmune diseases such as thyroiditis, rheumatoid arthritis and type 1 diabetes.

Example 13

Effect of 5G7 Mab on MOG 37-50 Peptide Mediated EAE

Multiple sclerosis (MS) is a chronic demyelinating disease of the human central nervous system (CNS) which can be characterized clinically by a remitting-relapsing or a chronic progressive course. The most intensively studied animal model of MS, experimental autoimmune encephalomyelitis (EAE), classically leads to deficit in motor functions. Many reports showed that T cells play crucial roles in the pathogenesis of MS and EAE. Therefore, we performed an EAE model experiment to investigate the inhibitory activity of 5G7 Mab on the pathogenesis of MS.
(Experimental Method)
1. Sample Mice Human XCR1 knock-in mice (7-12 weeks old), in which human XCR1 is expressed instead of mouse XCR1 on C57BL/6 background, were used for the experiment.
2. Induction of EAE The induction of EAE was performed according to the method reported in the journal Eur. J. Immunol. 2005, 35: 76-85, in which the probable role of CD8+ T cells was indicated in the EAE development. Briefly, the human XCR1 knock-in mice were injected subcutaneously with 200 μg of myelin oligodendrocyte glycoprotein 37-50 peptide (MOG 37-50) emulsified in Freund's complete adjuvant (CFA) containing 20 mg/ml of *Mycobacterium tuberculosis* H37Ra. 200 ng of pertussis toxin was administered intravenously on days 0 and 2, post-immunization.
3. Method for Administering Antibodies Anti-human XCR1 mouse monoclonal antibody (5G7) and its control antibody, i.e., mouse IgG (Jackson Laboratory), were prepared in PBS to a final concentration of 2 mg/mL. Each of the above antibodies was intravenously administered into the mice with the volume of 250 μl/mouse (500 μg/mouse) on day 7, day 10, day 14 and day 17.
4. Scoring of the Pathology of this Model Clinical symptom of EAE was monitored from the day of the immunization, and was scored on a scale of 0-5, based on the following criteria:
grade 0: no disease, grade 0.5: mild-tail paralysis, grade 1: tail paralysis, grade 2: uneven gait, grade 2.5: one paralyzed rear leg, grade 3: rear limb paralysis, grade 4: paralyzed front and rear legs: and grade 5: moribund or death.
(Experimental Result and Conclusion)

Figure 25:
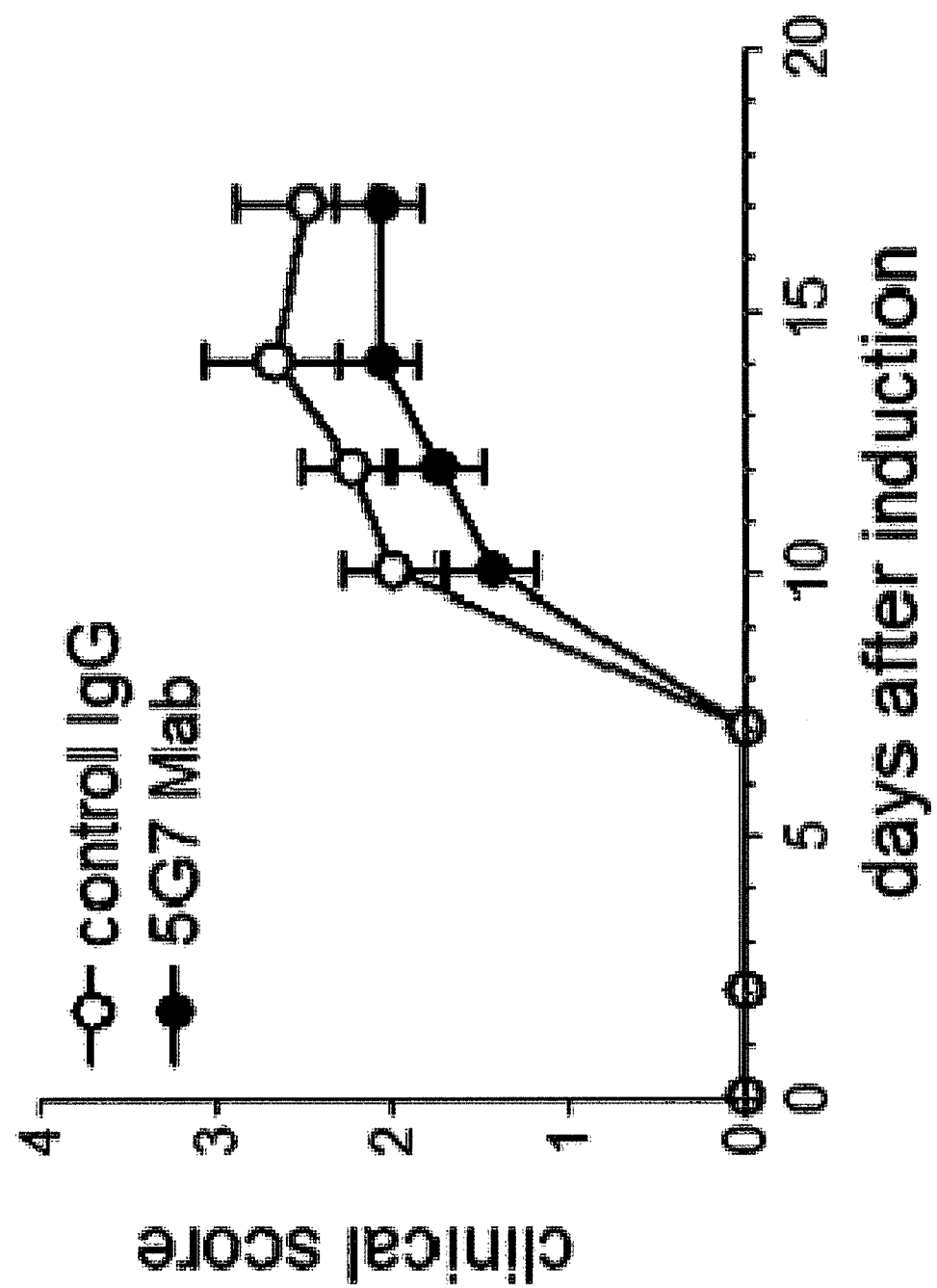
FIG. 25 shows a pharmacological effect of the mouse anti-human XCR1 antibody (5G7) of the present invention on a mouse model of multiple sclerosis (MS) by experimental autoimmune encephalomyelitis (EAE).

The obtained clinical scores of the mice administered with 5G7 Mab showed lower levels than those in the mice administered with the control IgG (FIG. 25). The data indicated that the treatment with anti-XCR1 antibody showed a certain level of suppression in the EAE development, and suggested that the treatment with anti-XCR1 antibodies may be beneficial for MS in human.

Example 14

Inhibition of Human XCL1 Binding to Human XCR1-Expressing Cells with Mouse Anti-Human XCR1 Antibodies (2H6, 5G7, and 11H2)

To determine whether mouse anti-human XCR1 antibodies (2H6, 5G7, and 11H2) inhibit human XCL1 binding to human XCR1, a competitive ligand binding assay was performed.

First, the binding of human XCL1-SSS-His(10) to human XCR1-EGFP-expressing BaF3 cells were determined according to the following procedure. Parent BaF3 cells and human XCR1-EGFP-expressing BaF3 cells were mixed at a 1:1 ratio, and suspended in a FACS buffer (1% FBS-containing PBS⁻ (Sigma)). The cells were incubated for 30 minutes on ice with an increasing concentration of human XCL1-SSS-His(10) in the presence or absence of 2.5 µM soluble XCL1 (R&D, #695-LT-025/CF) in the FACS buffer. Next, the cells were washed with the FACS buffer three times, and then incubated for 20 minutes on ice with anti-6×His tag antibody (BETHYL, #A190-114A, diluted at 1:100 in the FACS buffer). The cells were again washed with the FACS buffer three times, and then incubated for 20 minutes on ice with PE-labeled anti-rabbit IgG antibody (Jackson, #711-166-152, diluted at 1:50 in FACS buffer). Next, the cells were once again washed three times with the FACS buffer, and then suspended in the FACS buffer. The fluorescence intensity was measured using a FACSCanto II cell analyzer (BD Bioscience). Specific binding was determined by subtracting the non-specific binding (in the presence of 2.5 µM soluble XCL1) from the total binding (in the absence of 2.5 µM soluble XCL1).

The competitive ligand binding assay was performed according to the following procedure. Parent BaF3 cells and human XCR1-EGFP-expressing BaF3 cells were mixed at a 1:1 ratio, and suspended in a FACS buffer (1% FBS-containing PBS⁻ (Sigma)). The cells were blocked for 10 minutes on ice with a FACS buffer containing 10% rat serum. The cells were then incubated for 20 minutes on ice with mouse anti-human XCR1 antibodies (2H6, 5G7, or 11H2), mouse isotype control antibodies, IgG2a (eBioscience, #16-4724-85), or IgG2b (eBioscience, #16-4732-85) at various concentrations from 0 to 150 µg/mL. Next the cells were incubated for 30 minutes on ice with human XCL1-SSS-His(10) at a saturating concentration of 0.12 µg/mL. The cells were washed with the FACS buffer three times, and then incubated for 20 minutes on ice with anti-6×His tag antibody (BETHYL, #A190-114A, diluted at 1:100 in FACS buffer). The cells were again washed with the FACS buffer three times, and then incubated for 20 minutes on ice with PE-labeled anti-rabbit IgG antibody (Jackson, #711-166-152, diluted at 1:50 in FACS buffer). Next the cells were once again washed three times with the FACS buffer, and then suspended in FACS buffer. The fluorescence intensity was measured using a FACSCanto II cell analyzer (BD Bioscience).

Human XCL1 binding to human XCR1-EGFP-expressing BaF3 cells was inhibited with mouse anti-human XCR1 antibodies (2H6, 5G7, and 11H2), and the $IC_{50}$ of the antibodies was 37.0, 6.9, and 23.8 nM, respectively. On the other hand, control antibodies did not inhibit human XCL1 binding to human XCR-EGFP-expressing BaF3 cells.

The invention claimed is:

1. An antibody that binds to human XCR1, wherein the antibody comprises (i) a heavy chain variable region comprising a heavy chain complementarity determining region (CDR) 1 consisting of the amino acid sequence of SEQ ID NO:17, a heavy chain CDR 2 consisting of the amino acid sequence of SEQ ID NO:18, and a heavy chain CDR 3 consisting of the amino acid sequence of SEQ ID NO:19; and (ii) a light chain variable region comprising a light chain CDR 1 consisting of the amino acid sequence of SEQ ID NO:20, a light chain CDR 2 consisting of the amino acid sequence of SEQ ID NO:21, and a light chain CDR 3 consisting of the amino acid sequence of SEQ ID NO:22.

2. The antibody according to claim 1, wherein the heavy chain variable region comprises the amino acid sequence of SEQ ID NO: 60 or 64, and the light chain variable region comprises the amino acid sequence of SEQ ID NO: 68 or 72.

3. The antibody according to claim 1, wherein the heavy chain variable region comprises the amino acid sequence of SEQ ID NO: 60, and the light chain variable region comprises the amino acid sequence of SEQ ID NO: 68.

4. The antibody according to claim 1, wherein the heavy chain variable region comprises the amino acid sequence of SEQ ID NO: 64, and the light chain variable region comprises the amino acid sequence of SEQ ID NO: 72.

5. The antibody according to claim 1, wherein the antibody comprises a human constant region.

6. The antibody according to claim 1, wherein the antibody comprises a heavy chain comprising the amino acid sequence of SEQ ID NO: 59, and a light chain comprising the amino acid sequence of SEQ ID NO: 67.

7. The antibody according to claim 1, wherein the antibody comprises a heavy chain comprising the amino acid sequence of SEQ ID NO: 63, and a light chain comprising the amino acid sequence of SEQ ID NO: 71.

8. The antibody according to claim 1, comprising an Fc region, wherein the Fc region is mutated to induce a change in antibody-dependent cellular cytotoxicity (ADCC) activity.

9. The antibody according to claim 8, wherein the Fc region is mutated to lower ADCC activity.

10. The antibody according to claim 1, wherein the antibody is conjugated to a cytotoxic molecule.

11. The antibody according to claim 1, wherein the antibody inhibits interaction between human XCR1 and human XCL1.

12. The antibody according to claim 1, wherein the antibody inhibits cell migration of dendritic cells.

13. The antibody according to claim 1, wherein the antibody suppresses the activity of cytotoxic T lymphocytes.

14. A pharmaceutical composition comprising the antibody according to claim 1 and a pharmaceutically acceptable carrier or additive.

15. The antibody according to claim 1, wherein the antibody is a humanized antibody.

16. An antibody that binds to human XCR1, wherein the antibody comprises (i) a heavy chain variable region comprising a heavy chain complementarity determining region (CDR) 1 consisting of the amino acid sequence of SEQ ID NO:41, a heavy chain CDR 2 consisting of the amino acid sequence of SEQ ID NO:42, and a heavy chain CDR 3 consisting of the amino acid sequence of SEQ ID NO:43; and (ii) a light chain variable region comprising a light chain CDR 1 consisting of the amino acid sequence of SEQ ID NO:44, a light chain CDR 2 consisting of the amino acid sequence of SEQ ID NO:45, and a light chain CDR 3 consisting of the amino acid sequence of SEQ ID NO:46.

17. A pharmaceutical composition comprising the antibody according to claim 16 and a pharmaceutically acceptable carrier or additive.

18. The antibody according to claim 16, wherein the antibody is a humanized antibody.

19. An antibody that binds to human XCR1, wherein the antibody comprises (i) a heavy chain variable region comprising a heavy chain complementarity determining region (CDR) 1 consisting of the amino acid sequence of SEQ ID NO:29, a heavy chain CDR 2 consisting of the amino acid sequence of SEQ ID NO:30, and a heavy chain CDR 3 consisting of the amino acid sequence of SEQ ID NO:31; and (ii) a light chain variable region comprising a light chain CDR 1 consisting of the amino acid sequence of SEQ ID NO:32, a light chain CDR 2 consisting of the amino acid sequence of SEQ ID NO:33, and a light chain CDR 3 consisting of the amino acid sequence of SEQ ID NO:34.

20. A pharmaceutical composition comprising the antibody according to claim 19 and a pharmaceutically acceptable carrier or additive.

21. The antibody according to claim 19, wherein the antibody is a humanized antibody.

\* \* \* \* \*

SEQUENCE LISTING

```
<160> NUMBER OF SEQ ID NOS: 119

<210> SEQ ID NO 1
<211> LENGTH: 121
<212> TYPE: PRT
<213> ORGANISM: Artificial
<220> FEATURE:
<223> OTHER INFORMATION: Mouse Anti-Human XCR1 Antibody (2H6) Heavy
      chain variable region

<400> SEQUENCE: 1

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Ser Ser His
            20                  25                  30

Asn Met His Trp Ile Lys Gln Thr Leu Arg Gln Gly Leu Glu Trp Ile
        35                  40                  45

Gly Ala Ile Tyr Pro Gly Lys Gly Asn Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Trp Gly Ser Val Val Gly Asp Trp Tyr Phe Asp Val Trp Gly
            100                 105                 110

Thr Gly Thr Thr Val Thr Val Ser Ser
        115                 120
```

<210> SEQ ID NO 2
<211> LENGTH: 112
<212> TYPE: PRT
<213> ORGANISM: Artificial
<220> FEATURE:
<223> OTHER INFORMATION: Mouse Anti-Human XCR1 Antibody (2H6) Light
      chain variable region

<400> SEQUENCE: 2

Asp Val Val Thr Gln Thr Pro Leu Ser Leu Pro Val Ser Leu Gly
1               5                   10                  15

Asp Gln Ala Ser Ile Ser Cys Arg Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Leu Gly Arg Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr Phe Val Pro Trp Thr Phe Gly Gly Gly Thr Lys Leu Glu Ile Lys
            100                 105                 110

<210> SEQ ID NO 3
<211> LENGTH: 363
<212> TYPE: DNA
<213> ORGANISM: Artificial
<220> FEATURE:
<223> OTHER INFORMATION: Mouse Anti-Human XCR1 Antibody (2H6) Heavy
      chain variable region

<400> SEQUENCE: 3
caggcttatc tacagcagtc tgggctgaa ctggtgaggc ctggggcctc agtgaagatg      60
tcctgcaagg cttctggcta cacatttagc agtcacaata tgcactggat aaagcagaca    120
cttagacagg gcctggaatg gataggagct atttatccag gaaaaggtaa tacttcctac    180
aatcagaagt tcaagggcaa ggccacactg actgtagaca atcctccag cacagcctac     240 atgcagctca gcagcctgac atctgaagac tctgcggtct atttctgtgc aagatggggt    300
tcggtagtag agactggta cttcgatgtc tggggcacag gaccacggt caccgtctct      360 tca                                                                  363

<210> SEQ ID NO 4
<211> LENGTH: 336
<212> TYPE: DNA
<213> ORGANISM: Artificial
<220> FEATURE:
<223> OTHER INFORMATION: Mouse Anti-Human XCR1 Antibody (2H6) Light
      chain variable region

<400> SEQUENCE: 4
gatgttgtgg tgacccaaac tccactctcc ctgcctgtca gtcttggaga tcaagcctcc    60
atctcttgca gatctagtca gagccttgta cacagtaatg gaaacaccta tttacattgg   120
tacctgcaga agccaggcca gtctccaaag ctcctgatct acagagtttc caatcgattt   180
tctggggtcc cagacaggtt cagtggcagt ggattaggga gagatttcac actcaagatc   240
agcagagtgg aggctgagga tctgggagtt tatttctgct ctcaaagtac atttgttccg   300
tggacgttcg gtggaggcac caagctggaa atcaaa                             336

```
<210> SEQ ID NO 5
<211> LENGTH: 121
<212> TYPE: PRT
<213> ORGANISM: Artificial
<220> FEATURE:
<223> OTHER INFORMATION: Mouse Anti-Human XCR1 Antibody (5G7) Heavy
      chain variable region

<400> SEQUENCE: 5

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser His
            20                  25                  30

Asn Leu His Trp Val Lys Gln Thr Pro Arg Gln Gly Leu Gln Trp Ile
        35                  40                  45

Gly Ala Ile Tyr Pro Gly Asn Gly Asn Thr Ala Tyr Asn Gln Lys Phe
    50                  55                  60

Lys Gly Lys Ala Thr Leu Thr Val Asp Lys Ser Ser Thr Ala Tyr
65                  70                  75                  80

Met Gln Leu Ser Ser Leu Thr Ser Asp Asp Ser Ala Val Tyr Phe Cys
                85                  90                  95

Ala Arg Trp Gly Ser Val Val Gly Asp Trp Tyr Phe Asp Val Trp Gly
            100                 105                 110

Thr Gly Thr Thr Val Thr Val Ser Ser
        115                 120

<210> SEQ ID NO 6
<211> LENGTH: 112
<212> TYPE: PRT
<213> ORGANISM: Artificial
<220> FEATURE:
<223> OTHER INFORMATION: Mouse Anti-Human XCR1 Antibody (5G7) Light
      chain variable region

<400> SEQUENCE: 6

Asp Val Val Met Thr Gln Thr Pro Leu Ser Leu Pro Val Thr Leu Gly
1               5                   10                  15

Asn Gln Ala Ser Ile Phe Cys Arg Ser Ser Leu Gly Leu Val His Arg
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser His Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

<210> SEQ ID NO 7
<211> LENGTH: 363
<212> TYPE: DNA
<213> ORGANISM: Artificial
<220> FEATURE:
<223> OTHER INFORMATION: Mouse Anti-Human XCR1 Antibody (5G7) Heavy
      chain variable region

<400> SEQUENCE: 7
```

```
caggcttatc ttcagcagtc tgggctgaa ctggtgaggc tggggcctc agtgaagatg      60 tcctgcaagg cttctggcta cacattcacc agtcacaatt tgcactgggt aaagcagaca    120
cctagacagg gcctgcaatg gattggagct atttatccag gaaatggtaa tactgcctac    180
aatcagaagt tcaagggcaa ggccacgctg actgtagaca atcctccag tacagcctac     240 atgcagctca gcagcctgac atctgatgac tctgcggtct acttctgtgc aagatggggt    300
tcggttgtag agactggta cttcgacgtc tggggcacag ggaccacggt caccgtctcc     360
tca                                                                  363
```

```
<210> SEQ ID NO 8
<211> LENGTH: 336
<212> TYPE: DNA
<213> ORGANISM: Artificial
<220> FEATURE:
<223> OTHER INFORMATION: Mouse Anti-Human XCR1 Antibody (5G7) Light
      chain variable region

<400> SEQUENCE: 8
```

```
gatgttgtga tgacccaaac tccactctcc ctgcctgtca ctcttggaaa tcaagcctcc     60 atttttgta gatctagtct gggccttgta cacagaaatg gaaacaccta tttacattgg    120
tacctgcaga agccaggcca gtctccaaag ctcctgatct acaaagtttc ccaccgattt    180
tctggggtcc cagacaggtt cagtggcagt ggctcaggga cagatttcac actcaagatc    240
agcagagtgg aggctgagga tctgggggtt tatttctgct ctcaaagtac ccatgttccg    300
tggacgttcg gtggaggcac caagctggaa atcaaa                              336
```

```
<210> SEQ ID NO 9
<211> LENGTH: 122
<212> TYPE: PRT
<213> ORGANISM: Artificial
<220> FEATURE:
<223> OTHER INFORMATION: Mouse Anti-Human XCR1 Antibody (11H2) Heavy
      chain variable region

<400> SEQUENCE: 9
```

Glu Val Gln Leu Gln Gln Ser Gly Pro Val Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Val Asn Trp Val Lys Gln Ser His Gly Ala Ser Leu Glu Trp Ile
        35                  40                  45

Gly Val Ser Asn Pro Lys Asn Gly Asp Lys Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Asn Ser Leu Thr Ser Glu Asp Ser Ala Val Tyr Tyr Cys
                85                  90                  95

Ala Arg Gly Leu Tyr Tyr Ala Gly Thr Tyr Gly Tyr Phe Asp Val Trp
            100                 105                 110

Gly Thr Gly Thr Thr Val Thr Val Ser Ser
        115                 120

```
<210> SEQ ID NO 10
<211> LENGTH: 107
<212> TYPE: PRT
<213> ORGANISM: Artificial
<220> FEATURE:
<223> OTHER INFORMATION: Mouse Anti-Human XCR1 Antibody (11H2) Light
``` chain variable region

<400> SEQUENCE: 10

Asp Ile Gln Met Thr Gln Ala Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Arg Gly
    50                  55                  60

Ser Gly Ser Gly Thr Asp Phe Ser Leu Thr Ile Ser Asn Leu Glu Gln
65                  70                  75                  80

Glu Asp Ile Ala Thr Tyr Phe Cys Gln Gln Gly Lys Thr Leu Pro Arg
                85                  90                  95

Thr Leu Gly Gly Gly Thr Lys Leu Glu Ile Lys
            100                 105

<210> SEQ ID NO 11
<211> LENGTH: 366
<212> TYPE: DNA
<213> ORGANISM: Artificial
<220> FEATURE:
<223> OTHER INFORMATION: Mouse Anti-Human XCR1 Antibody (11H2) Heavy
      chain variable region

<400> SEQUENCE: 11
gaggtccagc ttcaacagtc tggacctgtg ctggtgaagc ctggggcttc agtgaagatg      60
tcctgtaagg cttctggata cacattcact gactactatg tgaactgggt gaaacagagc     120
catggagcga gccttgagtg gattggagtt agtaatccta agaacggtga taaaagttac     180
aaccagaagt tcaagggcaa ggccacattg actgttgaca gtcctccag tacagcctac      240 atggagctca acagcctgac atctgaggac tctgctgtct attactgtgc aagagggctt     300
tactacgctg gtacctacgg gtacttcgat gtctggggca cggggaccac ggtcaccgtc     360
tcctca                                                                366

<210> SEQ ID NO 12
<211> LENGTH: 321
<212> TYPE: DNA
<213> ORGANISM: Artificial
<220> FEATURE:
<223> OTHER INFORMATION: Mouse Anti-Human XCR1 Antibody (11H2) Light
      chain variable region

<400> SEQUENCE: 12
gatatccaga tgacacaggc tacatcctcc ctgtctgcct ctctgggaga cagagtcacc      60
atcagttgta gggcaagtca ggacattagc aattatttaa actggtatca gcagaagcca     120
gatggaactg ttaaactcct gatctactac acatcaagat acactcagg tgtcccatca      180 aggttcagag gcagtgggtc tgggacagat ttctctctca ccattagcaa cctggagcaa     240
gaagatattg ccacttattt ttgccaacag ggtaaaacgc ttcctcggac gctcggtgga     300
ggcaccaagc tggaaatcaa a                                               321

<210> SEQ ID NO 13
<211> LENGTH: 447
<212> TYPE: PRT
<213> ORGANISM: Artificial
<220> FEATURE:

<223> OTHER INFORMATION: Chimeric Anti-Human XCR1 Antibody Heavy chain

<400> SEQUENCE: 13

```
Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser His
            20                  25                  30

Asn Leu His Trp Val Lys Gln Thr Pro Arg Gln Gly Leu Gln Trp Ile
        35                  40                  45

Gly Ala Ile Tyr Pro Gly Asn Gly Asn Thr Ala Tyr Asn Gln Lys Phe
    50                  55                  60

Lys Gly Lys Ala Thr Leu Thr Val Asp Lys Ser Ser Thr Ala Tyr
65                  70                  75                  80

Met Gln Leu Ser Ser Leu Thr Ser Asp Asp Ser Ala Val Tyr Phe Cys
                85                  90                  95

Ala Arg Trp Gly Ser Val Val Gly Asp Trp Tyr Phe Asp Val Trp Gly
            100                 105                 110

Thr Gly Thr Thr Val Thr Val Ser Ala Ser Thr Lys Gly Pro Ser
            115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Ala Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400
```

```
Asp Gly Ser Phe Phe Leu Tyr Ser Lys Leu Thr Val Asp Lys Ser Arg
            405                 410                 415
Trp Gln Gln Gly Asn Val Phe Ser Cys Ser Val Met His Glu Ala Leu
        420                 425                 430
His Asn His Tyr Thr Gln Lys Ser Leu Ser Leu Ser Pro Gly Lys
        435                 440                 445

<210> SEQ ID NO 14
<211> LENGTH: 219
<212> TYPE: PRT
<213> ORGANISM: Artificial
<220> FEATURE:
<223> OTHER INFORMATION: Chimeric Anti-Human XCR1 Antibody Light chain

<400> SEQUENCE: 14

Asp Val Val Met Thr Gln Thr Pro Leu Ser Leu Pro Val Thr Leu Gly
1               5                   10                  15
Asn Gln Ala Ser Ile Phe Cys Arg Ser Ser Leu Gly Leu Val His Arg
            20                  25                  30
Asn Gly Asn Thr Tyr Leu His Trp Tyr Leu Gln Lys Pro Gly Gln Ser
        35                  40                  45
Pro Lys Leu Leu Ile Tyr Lys Val Ser His Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Leu Gly Val Tyr Phe Cys Ser Gln Ser
                85                  90                  95
Thr His Val Pro Trp Thr Phe Gly Gly Gly Thr Lys Leu Glu Ile Lys
            100                 105                 110
Arg Thr Val Ala Ala Pro Ser Val Phe Ile Phe Pro Pro Ser Asp Glu
        115                 120                 125
Gln Leu Lys Ser Gly Thr Ala Ser Val Val Cys Leu Leu Asn Asn Phe
    130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
            180                 185                 190
Lys His Lys Val Tyr Ala Cys Glu Val Thr His Gln Gly Leu Ser Ser
        195                 200                 205
Pro Val Thr Lys Ser Phe Asn Arg Gly Glu Cys
    210                 215

<210> SEQ ID NO 15
<211> LENGTH: 1344
<212> TYPE: DNA
<213> ORGANISM: Artificial
<220> FEATURE:
<223> OTHER INFORMATION: Chimeric Anti-Human XCR1 Antibody Heavy chain

<400> SEQUENCE: 15
caggcttatc ttcagcagtc tggggctgaa ctggtgaggc ctggggcctc agtgaagatg      60
tcctgcaagg cttctggcta cacattcacc agtcacaatt tgcactgggt aaagcagaca     120
cctagacagg gcctgcaatg gattggagct atttatccag aaatggtaa tactgcctac     180 aatcagaagt tcaagggcaa ggccacgctg actgtagaca atcctccag tacagcctac     240
```

```
atgcagctca gcagcctgac atctgatgac tctgcggtct acttctgtgc aagatggggt      300
tcggttgtag agactggta cttcgacgtc tggggcacag ggaccacggt caccgtctcc       360
tcagctagca ccaagggccc atcggtcttc cccctggcgc cctgctccag gagcacctcc      420
gagagcacag cggccctggg ctgcctggtc aaggactact ccccgaacc ggtgacggtg       480 tcgtggaact caggcgctct gaccagcggc gtgcacacct tcccggctgt cctacagtcc      540
tcaggactct actccctcag cagcgtggtg accgtgccct ccagcaactt cggcacccag      600
acctacacct gcaacgtaga tcacaagccc agcaacacca aggtggacaa gacagttgag      660
cgcaaatgtt gtgtcgagtg cccaccgtgc ccagcaccac ctgccgcagc ccgtcagtc       720 ttcctgttcc ccccaaaacc caaggacacc ctcatgatct cccggacccc tgaggtcacg      780
tgcgtggtgg tggacgtgag ccacgaagac cccgaggtcc agttcaactg gtacgtggac      840
ggcgtggagg tgcataatgc caagacaaag ccacgggagg agcagttcaa cagcacgttc      900
cgtgtggtca gcgtcctcac cgtcgtgcac caggactggc tgaacggcaa ggagtacaag      960
tgcaaggtct ccaacaaagg cctcccagcc cccatcgaga aaaccatctc caaaaccaaa      1020
gggcagcccc gagaaccaca ggtgtacacc ctgcccccat cccgggagga tgaccaag       1080 aaccaggtca gcctgacctg cctggtcaaa ggcttctacc ccagcgacat cgccgtggag      1140
tgggagagca atgggcagcc ggagaacaac tacaagacca cacctcccat gctggactcc      1200
gacggctcct tcttcctcta cagcaagctc accgtggaca gagcaggtg gcagcagggg      1260 aacgtcttct catgctccgt gatgcatgag gctctgcaca accactacac acagaagagc      1320 ctctcccctgt ctccgggtaa atga                                            1344
```

<210> SEQ ID NO 16
<211> LENGTH: 660
<212> TYPE: DNA
<213> ORGANISM: Artificial
<220> FEATURE:
<223> OTHER INFORMATION: Chimeric Anti-Human XCR1 Antibody Light chain

<400> SEQUENCE: 16

```
gatgttgtga tgacccaaac tccactctcc ctgcctgtca ctcttggaaa tcaagcctcc       60 atttttgta gatctagtct gggccttgta cacagaaatg gaaacaccta tttacattgg      120
tacctgcaga agccaggcca gtctccaaag ctcctgatct acaaagtttc caccgatt       180 tctggggtcc cagacaggtt cagtggcagt ggctcaggga cagatttcac actcaagatc      240
agcagagtgg aggctgagga tctggggggtt tatttctgct ctcaaagtac ccatgttccg      300
tggacgttcg gtggaggcac caagctggaa atcaaacgta cggtggctgc accatctgtc      360
ttcatcttcc cgccatctga tgagcagttg aaatctggaa ctgcctctgt tgtgtgcctg      420
ctgaataact tctatcccag agaggccaaa gtacagtgga aggtggataa cgccctccaa      480
tcgggtaact cccaggagag tgtcacagag caggacagca aggacagcac ctacagcctc      540
agcagcaccc tgacgctgag caaagcagac tacgagaaac acaaagtcta cgcctgcgaa      600
gtcacccatc agggcctgag ctcgcccgtc acaaagagct tcaacagggg agagtgttag      660
```

<210> SEQ ID NO 17
<211> LENGTH: 5
<212> TYPE: PRT
<213> ORGANISM: Artificial
<220> FEATURE:
<223> OTHER INFORMATION: Heavy chain CDR 1 of 5G7

<400> SEQUENCE: 17

Ser His Asn Leu His
1               5

<210> SEQ ID NO 18
<211> LENGTH: 17
<212> TYPE: PRT
<213> ORGANISM: Artificial
<220> FEATURE:
<223> OTHER INFORMATION: Heavy chain CDR 2 of 5G7

<400> SEQUENCE: 18

Ala Ile Tyr Pro Gly Asn Gly Asn Thr Ala Tyr Asn Gln Lys Phe Lys
1               5                   10                  15
Gly

<210> SEQ ID NO 19
<211> LENGTH: 12
<212> TYPE: PRT
<213> ORGANISM: Artificial
<220> FEATURE:
<223> OTHER INFORMATION: Heavy chain CDR 3 of 5G7

<400> SEQUENCE: 19

Trp Gly Ser Val Val Gly Asp Trp Tyr Phe Asp Val
1               5                   10

<210> SEQ ID NO 20
<211> LENGTH: 16
<212> TYPE: PRT
<213> ORGANISM: Artificial
<220> FEATURE:
<223> OTHER INFORMATION: Light chain CDR 1 of 5G7

<400> SEQUENCE: 20

Arg Ser Ser Leu Gly Leu Val His Arg Asn Gly Asn Thr Tyr Leu His
1               5                   10                  15

<210> SEQ ID NO 21
<211> LENGTH: 7
<212> TYPE: PRT
<213> ORGANISM: Artificial
<220> FEATURE:
<223> OTHER INFORMATION: Light chain CDR 2 of 5G7

<400> SEQUENCE: 21

Lys Val Ser His Arg Phe Ser
1               5

<210> SEQ ID NO 22
<211> LENGTH: 9
<212> TYPE: PRT
<213> ORGANISM: Artificial
<220> FEATURE:
<223> OTHER INFORMATION: Light chain CDR 3 of 5G7

<400> SEQUENCE: 22

Ser Gln Ser Thr His Val Pro Trp Thr
1               5

<210> SEQ ID NO 23
<211> LENGTH: 15
<212> TYPE: DNA
<213> ORGANISM: Artificial
<220> FEATURE:
<223> OTHER INFORMATION: Heavy chain CDR 1 of 5G7

<400> SEQUENCE: 23
agtcacaatt tgcac         15

<210> SEQ ID NO 24
<211> LENGTH: 51
<212> TYPE: DNA
<213> ORGANISM: Artificial
<220> FEATURE:
<223> OTHER INFORMATION: Heavy chain CDR 2 of 5G7

<400> SEQUENCE: 24
gctatttatc caggaaatgg taatactgcc tacaatcaga agttcaaggg c         51

<210> SEQ ID NO 25
<211> LENGTH: 36
<212> TYPE: DNA
<213> ORGANISM: Artificial
<220> FEATURE:
<223> OTHER INFORMATION: Heavy chain CDR 3 of 5G7

<400> SEQUENCE: 25
tggggttcgg ttgtaggaga ctggtacttc gacgtc         36

<210> SEQ ID NO 26
<211> LENGTH: 48
<212> TYPE: DNA
<213> ORGANISM: Artificial
<220> FEATURE:
<223> OTHER INFORMATION: Light chain CDR 1 of 5G7

<400> SEQUENCE: 26
agatctagtc tgggccttgt acacagaaat ggaaacacct atttacat         48

<210> SEQ ID NO 27
<211> LENGTH: 21
<212> TYPE: DNA
<213> ORGANISM: Artificial
<220> FEATURE:
<223> OTHER INFORMATION: Light chain CDR 2 of 5G7

<400> SEQUENCE: 27
aaagtttccc accgattttc t         21

<210> SEQ ID NO 28
<211> LENGTH: 27
<212> TYPE: DNA
<213> ORGANISM: Artificial
<220> FEATURE:
<223> OTHER INFORMATION: Light chain CDR 3 of 5G7

<400> SEQUENCE: 28
tctcaaagta cccatgttcc gtggacg         27

<210> SEQ ID NO 29
<211> LENGTH: 5
<212> TYPE: PRT
<213> ORGANISM: Artificial
<220> FEATURE:
<223> OTHER INFORMATION: Heavy chain CDR 1 of 2H6

<400> SEQUENCE: 29

Ser His Asn Met His
1               5

<210> SEQ ID NO 30

```
<211> LENGTH: 17
<212> TYPE: PRT
<213> ORGANISM: Artificial
<220> FEATURE:
<223> OTHER INFORMATION: Heavy chain CDR 2 of 2H6

<400> SEQUENCE: 30

Ala Ile Tyr Pro Gly Lys Gly Asn Thr Ser Tyr Asn Gln Lys Phe Lys
1               5                   10                  15
Gly

<210> SEQ ID NO 31
<211> LENGTH: 12
<212> TYPE: PRT
<213> ORGANISM: Artificial
<220> FEATURE:
<223> OTHER INFORMATION: Heavy chain CDR 3 of 2H6

<400> SEQUENCE: 31

Trp Gly Ser Val Val Gly Asp Trp Tyr Phe Asp Val
1               5                   10

<210> SEQ ID NO 32
<211> LENGTH: 16
<212> TYPE: PRT
<213> ORGANISM: Artificial
<220> FEATURE:
<223> OTHER INFORMATION: Light chain CDR 1 of 2H6

<400> SEQUENCE: 32

Arg Ser Ser Gln Ser Leu Val His Ser Asn Gly Asn Thr Tyr Leu His
1               5                   10                  15

<210> SEQ ID NO 33
<211> LENGTH: 7
<212> TYPE: PRT
<213> ORGANISM: Artificial
<220> FEATURE:
<223> OTHER INFORMATION: Light chain CDR 2 of 2H6

<400> SEQUENCE: 33

Arg Val Ser Asn Arg Phe Ser
1               5

<210> SEQ ID NO 34
<211> LENGTH: 9
<212> TYPE: PRT
<213> ORGANISM: Artificial
<220> FEATURE:
<223> OTHER INFORMATION: Light chain CDR 3 of 2H6

<400> SEQUENCE: 34

Ser Gln Ser Thr Phe Val Pro Trp Thr
1               5

<210> SEQ ID NO 35
<211> LENGTH: 15
<212> TYPE: DNA
<213> ORGANISM: Artificial
<220> FEATURE:
<223> OTHER INFORMATION: Heavy chain CDR 1 of 2H6

<400> SEQUENCE: 35
agtcacaata tgcac                                                  15

<210> SEQ ID NO 36
```

<210> SEQ ID NO 36
<211> LENGTH: 51
<212> TYPE: DNA
<213> ORGANISM: Artificial
<220> FEATURE:
<223> OTHER INFORMATION: Heavy chain CDR 2 of 2H6

<400> SEQUENCE: 36
gctatttatc caggaaaagg taatacttcc tacaatcaga agttcaaggg c    51

<210> SEQ ID NO 37
<211> LENGTH: 36
<212> TYPE: DNA
<213> ORGANISM: Artificial
<220> FEATURE:
<223> OTHER INFORMATION: Heavy chain CDR 3 of 2H6

<400> SEQUENCE: 37
tggggttcgg tagtaggaga ctggtacttc gatgtc    36

<210> SEQ ID NO 38
<211> LENGTH: 48
<212> TYPE: DNA
<213> ORGANISM: Artificial
<220> FEATURE:
<223> OTHER INFORMATION: Light chain CDR 1 of 2H6

<400> SEQUENCE: 38
agatctagtc agagccttgt acacagtaat ggaaacacct atttacat    48

<210> SEQ ID NO 39
<211> LENGTH: 21
<212> TYPE: DNA
<213> ORGANISM: Artificial
<220> FEATURE:
<223> OTHER INFORMATION: Light chain CDR 2 of 2H6

<400> SEQUENCE: 39
agagtttcca atcgattttc t    21

<210> SEQ ID NO 40
<211> LENGTH: 27
<212> TYPE: DNA
<213> ORGANISM: Artificial
<220> FEATURE:
<223> OTHER INFORMATION: Light chain CDR 3 of 2H6

<400> SEQUENCE: 40
tctcaaagta catttgttcc gtggacg    27

<210> SEQ ID NO 41
<211> LENGTH: 5
<212> TYPE: PRT
<213> ORGANISM: Artificial
<220> FEATURE:
<223> OTHER INFORMATION: Heavy chain CDR 1 of 11H2

<400> SEQUENCE: 41

Asp Tyr Tyr Val Asn
1               5

<210> SEQ ID NO 42
<211> LENGTH: 17
<212> TYPE: PRT
<213> ORGANISM: Artificial
<220> FEATURE:
<223> OTHER INFORMATION: Heavy chain CDR 2 of 11H2

```
<400> SEQUENCE: 42

Val Ser Asn Pro Lys Asn Gly Asp Lys Ser Tyr Asn Gln Lys Phe Lys
1               5                   10                  15

Gly

<210> SEQ ID NO 43
<211> LENGTH: 13
<212> TYPE: PRT
<213> ORGANISM: Artificial
<220> FEATURE:
<223> OTHER INFORMATION: Heavy chain CDR 3 of 11H2

<400> SEQUENCE: 43

Gly Leu Tyr Tyr Ala Gly Thr Tyr Gly Tyr Phe Asp Val
1               5                   10

<210> SEQ ID NO 44
<211> LENGTH: 11
<212> TYPE: PRT
<213> ORGANISM: Artificial
<220> FEATURE:
<223> OTHER INFORMATION: Light chain CDR 1 of 11H2

<400> SEQUENCE: 44

Arg Ala Ser Gln Asp Ile Ser Asn Tyr Leu Asn
1               5                   10

<210> SEQ ID NO 45
<211> LENGTH: 7
<212> TYPE: PRT
<213> ORGANISM: Artificial
<220> FEATURE:
<223> OTHER INFORMATION: Light chain CDR 2 of 11H2

<400> SEQUENCE: 45

Tyr Thr Ser Arg Leu His Ser
1               5

<210> SEQ ID NO 46
<211> LENGTH: 9
<212> TYPE: PRT
<213> ORGANISM: Artificial
<220> FEATURE:
<223> OTHER INFORMATION: Light chain CDR 3 of 11H2

<400> SEQUENCE: 46

Gln Gln Gly Lys Thr Leu Pro Arg Thr
1               5

<210> SEQ ID NO 47
<211> LENGTH: 15
<212> TYPE: DNA
<213> ORGANISM: Artificial
<220> FEATURE:
<223> OTHER INFORMATION: Heavy chain CDR 1 of 11H2

<400> SEQUENCE: 47
gactactatg tgaac                                                     15

<210> SEQ ID NO 48
<211> LENGTH: 51
<212> TYPE: DNA
<213> ORGANISM: Artificial
<220> FEATURE:
<223> OTHER INFORMATION: Heavy chain CDR 2 of 11H2
```

```
<400> SEQUENCE: 48
gttagtaatc ctaagaacgg tgataaaagt tacaaccaga agttcaaggg c          51

<210> SEQ ID NO 49
<211> LENGTH: 39
<212> TYPE: DNA
<213> ORGANISM: Artificial
<220> FEATURE:
<223> OTHER INFORMATION: Heavy chain CDR 3 of 11H2

<400> SEQUENCE: 49
gggctttact acgctggtac ctacgggtac ttcgatgtc                        39

<210> SEQ ID NO 50
<211> LENGTH: 33
<212> TYPE: DNA
<213> ORGANISM: Artificial
<220> FEATURE:
<223> OTHER INFORMATION: Light chain CDR 1 of 11H2

<400> SEQUENCE: 50
agggcaagtc aggacattag caattattta aac                              33

<210> SEQ ID NO 51
<211> LENGTH: 21
<212> TYPE: DNA
<213> ORGANISM: Artificial
<220> FEATURE:
<223> OTHER INFORMATION: Light chain CDR 2 of 11H2

<400> SEQUENCE: 51
tacacatcaa gattacactc a                                           21

<210> SEQ ID NO 52
<211> LENGTH: 27
<212> TYPE: DNA
<213> ORGANISM: Artificial
<220> FEATURE:
<223> OTHER INFORMATION: Light chain CDR 3 of 11H2

<400> SEQUENCE: 52
caacagggta aaacgcttcc tcggacg                                     27

<210> SEQ ID NO 53
<211> LENGTH: 5
<212> TYPE: PRT
<213> ORGANISM: Artificial
<220> FEATURE:
<223> OTHER INFORMATION: Generalized Amino Acid Sequences of
      Complementary Determining Regions of 5G7 and 2H6 (Heavy chain CDR
      1)
<220> FEATURE:
<221> NAME/KEY: MISC_FEATURE
<222> LOCATION: (4)..(4)
<223> OTHER INFORMATION: X is Ala, Arg, Asn, Asp, Cys, Gln, Glu, Gly,
      His, Ile, Leu, Lys, Met, Phe, Pro, Ser, Thr, Trp, Tyr, or Val.
<220> FEATURE:
<221> NAME/KEY: MISC_FEATURE
<222> LOCATION: (4)..(4)
<223> OTHER INFORMATION: Xaa is Ala, Arg, Asn, Asp, Cys, Gln, Glu, Gly,
      His, Ile, Leu, Lys, Met, Phe, Pro, Ser, Thr, Trp, Tyr, or Val.

<400> SEQUENCE: 53

Ser His Asn Xaa His
1               5

<210> SEQ ID NO 54
```

```
<211> LENGTH: 17
<212> TYPE: PRT
<213> ORGANISM: Artificial
<220> FEATURE:
<223> OTHER INFORMATION: Generalized Amino Acid Sequences of
      Complementary Determining Regions of 5G7 and 2H6 (Heavy chain
      CDR 2)
<220> FEATURE:
<221> NAME/KEY: MISC_FEATURE
<222> LOCATION: (6)..(6)
<223> OTHER INFORMATION: Xaa is Ala, Arg, Asn, Asp, Cys, Gln, Glu, Gly,
      His, Ile, Leu, Lys, Met, Phe, Pro, Ser, Thr, Trp, Tyr, or Val.
<220> FEATURE:
<221> NAME/KEY: MISC_FEATURE
<222> LOCATION: (10)..(10)
<223> OTHER INFORMATION: Xaa is Ala, Arg, Asn, Asp, Cys, Gln, Glu, Gly,
      His, Ile, Leu, Lys, Met, Phe, Pro, Ser, Thr, Trp, Tyr, or Val.

<400> SEQUENCE: 54

Ala Ile Tyr Pro Gly Xaa Gly Asn Thr Xaa Tyr Asn Gln Lys Phe Lys
1               5                   10                  15

Gly

<210> SEQ ID NO 55
<211> LENGTH: 12
<212> TYPE: PRT
<213> ORGANISM: Artificial
<220> FEATURE:
<223> OTHER INFORMATION: Generalized Amino Acid Sequences of
      Complementary Determining Regions of 5G7 and 2H6 (Heavy chain CDR
      3)

<400> SEQUENCE: 55

Trp Gly Ser Val Val Gly Asp Trp Tyr Phe Asp Val
1               5                   10

<210> SEQ ID NO 56
<211> LENGTH: 16
<212> TYPE: PRT
<213> ORGANISM: Artificial
<220> FEATURE:
<223> OTHER INFORMATION: Generalized Amino Acid Sequences of
      Complementary Determining Regions of 5G7 and 2H6 (Light chain CDR
      1)
<220> FEATURE:
<221> NAME/KEY: MISC_FEATURE
<222> LOCATION: (4)..(4)
<223> OTHER INFORMATION: Xaa is Ala, Arg, Asn, Asp, Cys, Gln, Glu, Gly,
      His, Ile, Leu, Lys, Met, Phe, Pro, Ser, Thr, Trp, Tyr, or Val.
<220> FEATURE:
<221> NAME/KEY: MISC_FEATURE
<222> LOCATION: (5)..(5)
<223> OTHER INFORMATION: Xaa is Ala, Arg, Asn, Asp, Cys, Gln, Glu, Gly,
      His, Ile, Leu, Lys, Met, Phe, Pro, Ser, Thr, Trp, Tyr, or Val.
<220> FEATURE:
<221> NAME/KEY: MISC_FEATURE
<222> LOCATION: (9)..(9)
<223> OTHER INFORMATION: Xaa is Ala, Arg, Asn, Asp, Cys, Gln, Glu, Gly,
      His, Ile, Leu, Lys, Met, Phe, Pro, Ser, Thr, Trp, Tyr, or Val.

<400> SEQUENCE: 56

Arg Ser Ser Xaa Xaa Leu Val His Xaa Asn Gly Asn Thr Tyr Leu His
1               5                   10                  15

<210> SEQ ID NO 57
<211> LENGTH: 7
<212> TYPE: PRT
<213> ORGANISM: Artificial
<220> FEATURE:
<223> OTHER INFORMATION: Generalized Amino Acid Sequences of
      Complementary Determining Regions of 5G7 and 2H6 (Light chain
      CDR 2)
```

```
<220> FEATURE:
<221> NAME/KEY: MISC_FEATURE
<222> LOCATION: (1)..(1)
<223> OTHER INFORMATION: Xaa is Ala, Arg, Asn, Asp, Cys, Gln, Glu, Gly,
      His, Ile, Leu, Lys, Met, Phe, Pro, Ser, Thr, Trp, Tyr, or Val.
<220> FEATURE:
<221> NAME/KEY: MISC_FEATURE
<222> LOCATION: (4)..(4)
<223> OTHER INFORMATION: Xaa is Ala, Arg, Asn, Asp, Cys, Gln, Glu, Gly,
      His, Ile, Leu, Lys, Met, Phe, Pro, Ser, Thr, Trp, Tyr, or Val.

<400> SEQUENCE: 57

Xaa Val Ser Xaa Arg Phe Ser
1               5

<210> SEQ ID NO 58
<211> LENGTH: 9
<212> TYPE: PRT
<213> ORGANISM: Artificial
<220> FEATURE:
<223> OTHER INFORMATION: Generalized Amino Acid Sequences of
      Complementary Determining Regions of 5G7 and 2H6 (Light chain
      CDR 3)
<220> FEATURE:
<221> NAME/KEY: MISC_FEATURE
<222> LOCATION: (5)..(5)
<223> OTHER INFORMATION: Xaa is Ala, Arg, Asn, Asp, Cys, Gln, Glu, Gly,
      His, Ile, Leu, Lys, Met, Phe, Pro, Ser, Thr, Trp, Tyr, or Val.

<400> SEQUENCE: 58

Ser Gln Ser Thr Xaa Val Pro Trp Thr
1               5

<210> SEQ ID NO 59
<211> LENGTH: 447
<212> TYPE: PRT
<213> ORGANISM: Artificial
<220> FEATURE:
<223> OTHER INFORMATION: Humanized Anti-Human XCR1 Antibody Heavy Chain
      (HK1)

<400> SEQUENCE: 59

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Asn Leu His Trp Val Arg Gln Ala Pro Gly Gln Arg Leu Glu Trp Met
        35                  40                  45

Gly Ala Ile Tyr Pro Gly Asn Gly Asn Thr Ala Tyr Asn Gln Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Ser Val Val Gly Asp Trp Tyr Phe Asp Val Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175
```

```
Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
            195                 200                 205

Lys Pro Ser Asn Thr Lys Val Asp Lys Thr Val Glu Arg Lys Cys Cys
210                 215                 220

Val Glu Cys Pro Pro Cys Pro Ala Pro Pro Ala Ala Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Phe Arg Val Val Ser
290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 60
<211> LENGTH: 121
<212> TYPE: PRT
<213> ORGANISM: Artificial
<220> FEATURE:
<223> OTHER INFORMATION: Humanized Anti-Human XCR1 Antibody Heavy
      Chain (HK1) variable region

<400> SEQUENCE: 60

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Asn Leu His Trp Val Arg Gln Ala Pro Gly Gln Arg Leu Glu Trp Met
        35                  40                  45

Gly Ala Ile Tyr Pro Gly Asn Gly Asn Thr Ala Tyr Asn Gln Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
```

```
                  85                  90                  95
Ala Arg Trp Gly Ser Val Val Gly Asp Trp Tyr Phe Asp Val Trp Gly
               100                 105                 110
Gln Gly Thr Leu Val Thr Val Ser Ser
               115                 120
```

<210> SEQ ID NO 61
<211> LENGTH: 1344
<212> TYPE: DNA
<213> ORGANISM: Artificial
<220> FEATURE:
<223> OTHER INFORMATION: Humanized Anti-Human XCR1 Antibody Heavy Chain
      (HK1)

<400> SEQUENCE: 61

| | | | | | |
|---|---|---|---|---|---|
| caggtgcagc | tggtgcagtc | tggagccgaa | gtgaagaaac | aggggcctc | tgtcaaggtg | 60 |
| agttgcaagg | cctccggtta | cactttcacc | tcccacaacc | tgcattgggt | gagacaggct | 120 |
| cctggacagc | gactggagtg | gatgggagca | atctacccag | gcaacggaaa | tactgcctat | 180 |
| aatcagaagt | ttaaaggcag | ggtgacaatt | actcgggaca | cttccgcaag | caccgcctac | 240 |
| atggagctgt | ccagcctgag | gagtgaagat | accgctgtgt | actattgtgc | acgatgggga | 300 |
| tccgtggtcg | gagactggta | tttcgatgtg | tggggggcagg | gtaccctggt | cacagtgtct | 360 |
| agtgcctcca | caagggccc | cagcgtgttt | ccactggctc | cctgctctag | gagtacatca | 420 |
| gagtccactg | ccgctctggg | atgtctggtg | aaggactatt | tccctgaacc | agtcaccgtg | 480 |
| agttggaact | caggggctct | gacatctggt | gtccacactt | tcctgcagt | gctgcagtca | 540 |
| tccggcctgt | actccctgag | ctctgtggtc | acagtcccaa | gttcaaattt | cggaacccag | 600 |
| acatatactt | gcaacgtgga | ccataagccc | agcaatacca | aggtcgataa | aacagtggag | 660 |
| cgaaagtgct | gtgtcgaatg | cccaccttgt | ccagctccac | cagcagcagc | tccttctgtg | 720 |
| ttcctgtttc | ctccaaagcc | aaaagacact | ctgatgatca | gccggacccc | cgaggtcaca | 780 |
| tgtgtggtcg | tggacgtgtc | tcacgaggat | cctgaagtcc | agtttaactg | gtacgtggat | 840 |
| ggggtcgaag | tgcataatgc | aaagacaaaa | ccacgagagg | aacagttcaa | ctctacattt | 900 |
| cgtgtcgtga | gtgtgctgac | tgtcgtgcac | caggattggc | tgaacggcaa | ggagtataag | 960 |
| tgcaaagtgt | ccaataaggg | actgccccgcc | cctatcgaga | aaactattag | caagaccaaa | 1020 |
| ggccagccta | gagaaccaca | ggtgtacacc | ctgccccccta | gtcgcgagga | aatgactaag | 1080 |
| aaccaggtct | cactgacctg | tctggtgaaa | gggttctatc | ccagcgacat | tgccgtggag | 1140 |
| tgggaatcta | atggtcagcc | tgagaacaat | tacaagacca | caccacccat | gctggactcc | 1200 |
| gatgggagct | tctttctgta | ttcaaagctg | accgtggata | atccaggtg | gcagcagggt | 1260 |
| aatgtctttta | gctgctctgt | gatgcacgaa | gccctgcaca | accattacac | tcagaagtcc | 1320 |
| ctgtccctgt | cacctggaaa | gtga | | | | 1344 |

<210> SEQ ID NO 62
<211> LENGTH: 363
<212> TYPE: DNA
<213> ORGANISM: Artificial
<220> FEATURE:
<223> OTHER INFORMATION: Humanized Anti-Human XCR1 Antibody Heavy Chain
      (HK1) variable region

<400> SEQUENCE: 62

| | | | | | |
|---|---|---|---|---|---|
| caggtgcagc | tggtgcagtc | tggagccgaa | gtgaagaaac | aggggcctc | tgtcaaggtg | 60 |
| agttgcaagg | cctccggtta | cactttcacc | tcccacaacc | tgcattgggt | gagacaggct | 120 |

```
cctggacagc gactggagtg gatgggagca atctacccag gcaacggaaa tactgcctat    180
aatcagaagt ttaaaggcag ggtgacaatt actcgggaca cttccgcaag caccgcctac    240
atggagctgt ccagcctgag gagtgaagat accgctgtgt actattgtgc acgatgggga    300
tccgtggtcg gagactggta tttcgatgtg tggggcagg gtaccctggt cacagtgtct    360
agt                                                                 363
```

<210> SEQ ID NO 63
<211> LENGTH: 447
<212> TYPE: PRT
<213> ORGANISM: Artificial
<220> FEATURE:
<223> OTHER INFORMATION: Humanized Anti-Human XCR1 Antibody Heavy Chain (HK5)

<400> SEQUENCE: 63

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Asn Leu His Trp Val Arg Gln Ala Pro Gly Gln Gly Leu Glu Trp Met
        35                  40                  45

Gly Ala Ile Tyr Pro Gly Asn Gly Asn Thr Ala Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Trp Gly Ser Val Val Gly Asp Trp Tyr Phe Asp Val Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Pro Ala Ala Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300
```

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
            325                 330                 335

Ser Lys Thr Lys Gly Gln Pro Arg Glu Pro Gln Val Tyr Thr Leu Pro
        340                 345                 350

Pro Ser Arg Glu Glu Met Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly Lys
    435                 440                 445

<210> SEQ ID NO 64
<211> LENGTH: 121
<212> TYPE: PRT
<213> ORGANISM: Artificial
<220> FEATURE:
<223> OTHER INFORMATION: Humanized Anti-Human XCR1 Antibody Heavy
      Chain (HK5) variable region

<400> SEQUENCE: 64

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Asn Leu His Trp Val Arg Gln Ala Pro Gly Gln Gly Leu Glu Trp Met
        35                  40                  45

Gly Ala Ile Tyr Pro Gly Asn Gly Asn Thr Ala Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Trp Gly Ser Val Val Gly Asp Trp Tyr Phe Asp Val Trp Gly
            100                 105                 110

Gln Gly Thr Leu Val Thr Val Ser Ser
        115                 120

<210> SEQ ID NO 65
<211> LENGTH: 1344
<212> TYPE: DNA
<213> ORGANISM: Artificial
<220> FEATURE:
<223> OTHER INFORMATION: Humanized Anti-Human XCR1 Antibody Heavy Chain
      (HK5)

<400> SEQUENCE: 65
caggtgcagc tggtgcagtc tggggccgaa gtgaagaaac caggggcttc tgtcaaggtg      60
agttgcaaag catcaggtta cactttcacc tcccacaacc tgcattgggt gcgacaggct     120
cctggacagg gactggagtg gatgggagca atctacccag gaacggtaa taccgcttat     180

```
aatcagaagt ttaaaggcag ggtcacaatg actcgggaca cctccacaag cactgtgtac      240
atggagctgt ccagcctgcg aagtgaagat acagcagtgt actattgtgc acgttgggga      300
tccgtggtcg gtgactggta tttcgatgtg tggggccagg gaaccctggt cacagtgtct      360
agtgcttcca ctaaggggcc cagcgtgttt ccactggcac cctgctctcg gagtacttca      420
gagtccaccg ccgctctggg ctgtctggtg aaggactatt tccctgaacc agtcacagtg      480
agttggaact caggcgcact gacttctgga gtccacacct ttcctgccgt gctgcagtca      540
tccggcctgt actccctgag ctctgtggtc actgtcccaa gttcaaattt cggaacccag      600
acatatactt gcaacgtgga ccataagccc agcaatacaa aggtcgataa aactgtggag      660
agaaagtgct gtgtggaatg cccaccttgt ccagcaccac cagcagcagc tccttctgtg      720
ttcctgtttc ctccaaagcc aaaagacaca ctgatgatca gccgcacacc cgaggtcact      780
tgtgtggtcg tggacgtgtc tcacgaggat cctgaagtcc agtttaactg gtacgtggat      840
ggcgtcgaag tgcataatgc caagaccaaa ccaagagagg aacagttcaa ctctactttt      900
cgcgtcgtga gtgtgctgac cgtcgtgcac caggattggc tgaacggcaa ggagtataag      960
tgcaaagtgt ccaataaggg actgcccgct cctatcgaga aaccattagg caagacaaaa     1020
ggacagccta gggaaccaca ggtgtacacc ctgcccccta gtcgggagga aatgaccaag     1080
aaccaggtct cactgacatg tctggtgaaa gggttctatc ccagcgacat tgccgtggag     1140
tgggaatcta atggtcagcc tgagaacaat tacaagacca caccaccat gctggactcc      1200 gatggcagct tctttctgta ttcaaagctg accgtggata atccaggtg gcagcaggga     1260 aatgtcttta gctgctctgt gatgcacgaa gcactgcata tcactacac tcagaagagc     1320 ctgtccctgt cacctggtaa atga                                            1344

<210> SEQ ID NO 66
<211> LENGTH: 363
<212> TYPE: DNA
<213> ORGANISM: Artificial
<220> FEATURE:
<223> OTHER INFORMATION: Humanized Anti-Human XCR1 Antibody Heavy Chain
      (HK5) variable region

<400> SEQUENCE: 66
caggtgcagc tggtgcagtc tggggccgaa gtgaagaaac caggggcttc tgtcaaggtg       60
agttgcaaag catcaggtta cactttcacc tcccacaacc tgcattgggt gcgacaggct      120
cctggacagg gactggagtg gatgggagca atctacccag ggaacggtaa taccgcttat      180
aatcagaagt ttaaaggcag ggtcacaatg actcgggaca cctccacaag cactgtgtac      240
atggagctgt ccagcctgcg aagtgaagat acagcagtgt actattgtgc acgttgggga      300
tccgtggtcg gtgactggta tttcgatgtg tggggccagg gaaccctggt cacagtgtct      360
agt                                                                    363

<210> SEQ ID NO 67
<211> LENGTH: 219
<212> TYPE: PRT
<213> ORGANISM: Artificial
<220> FEATURE:
<223> OTHER INFORMATION: Humanized Anti-Human XCR1 Antibody Light Chain
      (L2)

<400> SEQUENCE: 67

Asp Val Val Met Thr Gln Ser Pro Leu Ser Leu Pro Val Thr Leu Gly
1               5                   10                  15
```

```
Gln Pro Ala Ser Ile Ser Cys Arg Ser Ser Leu Gly Leu Val His Arg
                20                  25                  30

Asn Gly Asn Thr Tyr Leu His Trp Phe Gln Gln Arg Pro Gly Gln Ser
            35                  40                  45

Pro Arg Leu Leu Ile Tyr Lys Val Ser His Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr His Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 68
<211> LENGTH: 112
<212> TYPE: PRT
<213> ORGANISM: Artificial
<220> FEATURE:
<223> OTHER INFORMATION: Humanized Anti-Human XCR1 Antibody Light Chain
      (L2) variable region

<400> SEQUENCE: 68

Asp Val Val Met Thr Gln Ser Pro Leu Ser Leu Pro Val Thr Leu Gly
 1               5                  10                  15

Gln Pro Ala Ser Ile Ser Cys Arg Ser Ser Leu Gly Leu Val His Arg
                20                  25                  30

Asn Gly Asn Thr Tyr Leu His Trp Phe Gln Gln Arg Pro Gly Gln Ser
            35                  40                  45

Pro Arg Leu Leu Ile Tyr Lys Val Ser His Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr His Val Pro Trp Thr Phe Gly Gln Gly Thr Lys Val Glu Ile Lys
            100                 105                 110

<210> SEQ ID NO 69
<211> LENGTH: 660
<212> TYPE: DNA
<213> ORGANISM: Artificial
<220> FEATURE:
<223> OTHER INFORMATION: Humanized Anti-Human XCR1 Antibody Light Chain
      (L2)
```

<400> SEQUENCE: 69

```
gatgtcgtga tgacccagtc tcctctgagc ctgcctgtga ctctgggcca gccagcatca      60
atctcctgcc gatccagcct gggactggtg caccgtaacg ggaataccta cctgcattgg    120
ttccagcaga ggcctggtca gagtccccgg ctgctgatct ataaggtgtc tcacagattc    180
agtggcgtcc cagaccgctt tagcggctct ggaagtggga ctgatttcac cctgaaaatt    240
tcccgagtgg aggcagaaga cgtgggagtc tactattgct cacagtccac acatgtgccc    300
tggacttttg gtcagggcac caaggtcgag atcaaacgca ccgtggccgc tcctagcgtc    360
ttcattttc ccccttctga cgaacagctg aagtcaggaa cagcttccgt ggtctgtctg    420
ctgaacaatt tttaccccag agaggcaaag gtgcagtgga agtcgataa cgccctgcag     480
agcggcaact cccaggagag tgtgacagaa caggactcaa aggattccac ttatagcctg    540
tctagtaccc tgacactgtc taaagctgat tacgagaagc acaaagtgta tgcatgtgaa    600
gtcacccacc agggctgtc atcacccgtc accaagtcct taatagagg ggagtgttga     660
```

<210> SEQ ID NO 70
<211> LENGTH: 336
<212> TYPE: DNA
<213> ORGANISM: Artificial
<220> FEATURE:
<223> OTHER INFORMATION: Humanized Anti-Human XCR1 Antibody Light Chain
      (L2) variable region

<400> SEQUENCE: 70

```
gatgtcgtga tgacccagtc tcctctgagc ctgcctgtga ctctgggcca gccagcatca      60
atctcctgcc gatccagcct gggactggtg caccgtaacg ggaataccta cctgcattgg    120
ttccagcaga ggcctggtca gagtccccgg ctgctgatct ataaggtgtc tcacagattc    180
agtggcgtcc cagaccgctt tagcggctct ggaagtggga ctgatttcac cctgaaaatt    240
tcccgagtgg aggcagaaga cgtgggagtc tactattgct cacagtccac acatgtgccc    300
tggacttttg gtcagggcac caaggtcgag atcaaa                              336
```

<210> SEQ ID NO 71
<211> LENGTH: 219
<212> TYPE: PRT
<213> ORGANISM: Artificial
<220> FEATURE:
<223> OTHER INFORMATION: Humanized Anti-Human XCR1 Antibody Light Chain
      (L5)

<400> SEQUENCE: 71

```
Asp Ile Val Met Thr Gln Thr Pro Leu Ser Leu Pro Val Thr Pro Gly
1               5                   10                  15

Gln Pro Ala Ser Ile Ser Cys Arg Ser Ser Leu Gly Leu Val His Arg
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser His Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
            100                 105                 110
```

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
        180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215

<210> SEQ ID NO 72
<211> LENGTH: 112
<212> TYPE: PRT
<213> ORGANISM: Artificial
<220> FEATURE:
<223> OTHER INFORMATION: Humanized Anti-Human XCR1 Antibody Light Chain
      (L5) variable Region

<400> SEQUENCE: 72

Asp Ile Val Met Thr Gln Thr Pro Leu Ser Leu Pro Val Thr Pro Gly
1               5                   10                  15

Gln Pro Ala Ser Ile Ser Cys Arg Ser Ser Leu Gly Leu Val His Arg
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser His Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
            100                 105                 110

<210> SEQ ID NO 73
<211> LENGTH: 660
<212> TYPE: DNA
<213> ORGANISM: Artificial
<220> FEATURE:
<223> OTHER INFORMATION: Humanized Anti-Human XCR1 Antibody Light Chain
      (L5)

<400> SEQUENCE: 73
gatattgtga tgactcagac tccactgagc ctgccagtga ctcccggcca gcctgcatca      60
atctcctgca gatccagcct gggactggtg caccgcaacg gaataccta cctgcattgg     120 tatctgcaga agcctggtca gagtccccag ctgctgatct acaaagtgtc tcacaggttc    180
agtggcgtcc ccgaccggtt tagcggctct ggaagtggga ctgatttcac cctgaagatt    240
tcccgagtgg aggccgaaga cgtgggcgtc tactattgct cacagtccac acatgtgcct    300 tggactttg gtcagggcac caaggtcgag atcaaaagga ccgtggccgc tccaagcgtc    360
ttcatttttc cccttctga cgaacagctg aagtcaggaa cagcttccgt ggtctgtctg    420

```
ctgaacaatt tctaccccag agaggcaaag gtgcagtgga aagtcgataa cgccctgcag    480
agcggcaact cccaggagag tgtgacagaa caggactcaa aggattccac ttatagcctg    540
tctagtaccc tgacactgtc taaagctgat tacgagaagc acaaagtgta tgcatgtgaa    600
gtcacacacc agggtctgag ttcccccgtc accaaatcct ttaatcgtgg agagtgctga    660
```

<210> SEQ ID NO 74
<211> LENGTH: 336
<212> TYPE: DNA
<213> ORGANISM: Artificial
<220> FEATURE:
<223> OTHER INFORMATION: Humanized Anti-Human XCR1 Antibody Light Chain
      (L5) variable Region

<400> SEQUENCE: 74

```
gatattgtga tgactcagac tccactgagc ctgccagtga ctcccggcca gcctgcatca     60
atctcctgca gatccagcct gggactggtg caccgcaacg gaataccta cctgcattgg    120 tatctgcaga agcctggtca gagtccccag ctgctgatct acaaagtgtc tcacaggttc    180
agtggcgtcc ccgaccggtt tagcggctct ggaagtggga ctgatttcac cctgaagatt    240
tcccgagtgg aggccgaaga cgtgggcgtc tactattgct cacagtccac acatgtgcct    300 tggactttg gtcagggcac caaggtcgag atcaaa                              336
```

<210> SEQ ID NO 75
<211> LENGTH: 57
<212> TYPE: DNA
<213> ORGANISM: Artificial
<220> FEATURE:
<223> OTHER INFORMATION: Signal sequence

<400> SEQUENCE: 75

```
atgggattca gcaggatctt tctcttcctc ctgtcagtaa ctacaggtgt ccactcc        57
```

<210> SEQ ID NO 76
<211> LENGTH: 57
<212> TYPE: DNA
<213> ORGANISM: Artificial
<220> FEATURE:
<223> OTHER INFORMATION: Signal sequence

<400> SEQUENCE: 76

```
atgaagttgc ctgttaggct gttggtgctg ctgttctggt tcctgcttcc caacact        57
```

<210> SEQ ID NO 77
<211> LENGTH: 57
<212> TYPE: DNA
<213> ORGANISM: Artificial
<220> FEATURE:
<223> OTHER INFORMATION: Signal sequence

<400> SEQUENCE: 77

```
atggaatggt catgggtctt tctgttcttt ctgagtgtca caaccggggt gcatagc        57
```

<210> SEQ ID NO 78
<211> LENGTH: 57
<212> TYPE: DNA
<213> ORGANISM: Artificial
<220> FEATURE:
<223> OTHER INFORMATION: Signal sequence

<400> SEQUENCE: 78

```
atggaatggt cttgggtctt tctgttcttt ctgtccgtca ctaccggggt ccactct        57
```

<210> SEQ ID NO 79
<211> LENGTH: 60
<212> TYPE: DNA
<213> ORGANISM: Artificial
<220> FEATURE:
<223> OTHER INFORMATION: Signal sequence

<400> SEQUENCE: 79
atgtccgtgc ctactcaggt gctggggctg ctgctgctgt ggctgaccga tgctcgttgc    60

<210> SEQ ID NO 80
<211> LENGTH: 60
<212> TYPE: DNA
<213> ORGANISM: Artificial
<220> FEATURE:
<223> OTHER INFORMATION: Signal sequence

<400> SEQUENCE: 80
atgtccgtgc ctactcaggt gctggggctg ctgctgctgt ggctgaccga tgctcgttgt    60

<210> SEQ ID NO 81
<211> LENGTH: 12
<212> TYPE: DNA
<213> ORGANISM: Artificial
<220> FEATURE:
<223> OTHER INFORMATION: 5' adaptor ad29S

<400> SEQUENCE: 81
acatcactcc gt                                                        12

<210> SEQ ID NO 82
<211> LENGTH: 50
<212> TYPE: DNA
<213> ORGANISM: Artificial
<220> FEATURE:
<223> OTHER INFORMATION: 5' adaptor obtained 29AS

<400> SEQUENCE: 82
acggagtgat gtccgtcgac gtatctctgc gttgatactt cagcgtagct               50

<210> SEQ ID NO 83
<211> LENGTH: 26
<212> TYPE: DNA
<213> ORGANISM: Artificial
<220> FEATURE:
<223> OTHER INFORMATION: Primer

<400> SEQUENCE: 83
agctacgctg aagtatcaac gcagag                                         26

<210> SEQ ID NO 84
<211> LENGTH: 21
<212> TYPE: DNA
<213> ORGANISM: Artificial
<220> FEATURE:
<223> OTHER INFORMATION: Primer

<400> SEQUENCE: 84
aggacagggg ttgattgttg a                                              21

<210> SEQ ID NO 85
<211> LENGTH: 26
<212> TYPE: DNA
<213> ORGANISM: Artificial
<220> FEATURE:
<223> OTHER INFORMATION: Primer

<400> SEQUENCE: 85
ctcaagtttt ttgtccaccg tggtgc                                          26

<210> SEQ ID NO 86
<211> LENGTH: 26
<212> TYPE: DNA
<213> ORGANISM: Artificial
<220> FEATURE:
<223> OTHER INFORMATION: Primer

<400> SEQUENCE: 86
ctcaattttc ttgtccacct tggtgc                                          26

<210> SEQ ID NO 87
<211> LENGTH: 19
<212> TYPE: DNA
<213> ORGANISM: Artificial
<220> FEATURE:
<223> OTHER INFORMATION: Primer

<400> SEQUENCE: 87
gccagtggat agactgatg                                                  19

<210> SEQ ID NO 88
<211> LENGTH: 27
<212> TYPE: DNA
<213> ORGANISM: Artificial
<220> FEATURE:
<223> OTHER INFORMATION: Primer

<400> SEQUENCE: 88
ctcattcctg ttgaagctct tgacaat                                         27

<210> SEQ ID NO 89
<211> LENGTH: 21
<212> TYPE: DNA
<213> ORGANISM: Artificial
<220> FEATURE:
<223> OTHER INFORMATION: Primer

<400> SEQUENCE: 89
gatggataca gttggtgcag c                                               21

<210> SEQ ID NO 90
<211> LENGTH: 24
<212> TYPE: DNA
<213> ORGANISM: Artificial
<220> FEATURE:
<223> OTHER INFORMATION: Primer

<400> SEQUENCE: 90
cagatcctca gcctccactc tgct                                            24

<210> SEQ ID NO 91
<211> LENGTH: 333
<212> TYPE: PRT
<213> ORGANISM: Abramis brama

<400> SEQUENCE: 91

Met Glu Ser Ser Gly Asn Pro Glu Ser Thr Thr Phe Phe Tyr Tyr Asp
1               5                   10                  15

Leu Gln Ser Gln Pro Cys Glu Asn Gln Ala Trp Val Phe Ala Thr Leu
            20                  25                  30

Ala Thr Thr Val Leu Tyr Cys Leu Val Phe Leu Ser Leu Val Gly
            35              40              45

Asn Ser Leu Val Leu Trp Val Leu Val Lys Tyr Glu Ser Leu Glu Ser
 50              55              60

Leu Thr Asn Ile Phe Ile Leu Asn Leu Cys Leu Ser Asp Leu Val Phe
 65              70              75              80

Ala Cys Leu Leu Pro Val Trp Ile Ser Pro Tyr His Trp Gly Trp Val
            85              90              95

Leu Gly Asp Phe Leu Cys Lys Leu Leu Asn Met Ile Phe Ser Ile Ser
            100             105             110

Leu Tyr Ser Ser Ile Phe Phe Leu Thr Ile Met Thr Ile His Arg Tyr
            115             120             125

Leu Ser Val Val Ser Pro Leu Ser Thr Leu Arg Val Pro Thr Leu Arg
            130             135             140

Cys Arg Val Leu Val Thr Met Ala Val Trp Val Ala Ser Ile Leu Ser
145             150             155             160

Ser Ile Leu Asp Thr Ile Phe His Lys Val Leu Ser Ser Gly Cys Asp
                165             170             175

Tyr Ser Glu Leu Thr Trp Tyr Leu Thr Ser Val Tyr Gln His Asn Leu
            180             185             190

Phe Phe Leu Leu Ser Leu Gly Ile Ile Leu Phe Cys Tyr Val Glu Ile
            195             200             205

Leu Arg Thr Leu Phe Arg Ser Arg Ser Lys Arg Arg His Arg Thr Val
            210             215             220

Lys Leu Ile Phe Ala Ile Val Val Ala Tyr Phe Leu Ser Trp Gly Pro
225             230             235             240

Tyr Asn Phe Thr Leu Phe Leu Gln Thr Leu Phe Arg Thr Gln Ile Ile
            245             250             255

Arg Ser Cys Glu Ala Lys Gln Gln Leu Glu Tyr Ala Leu Leu Ile Cys
            260             265             270

Arg Asn Leu Ala Phe Ser His Cys Cys Phe Asn Pro Val Leu Tyr Val
            275             280             285

Phe Val Gly Val Lys Phe Arg Thr His Leu Lys His Val Leu Arg Gln
            290             295             300

Phe Trp Phe Cys Arg Leu Gln Ala Pro Ser Pro Ala Ser Ile Pro His
305             310             315             320

Ser Pro Gly Ala Phe Ala Tyr Glu Gly Ala Ser Phe Tyr
            325             330

<210> SEQ ID NO 92
<211> LENGTH: 12
<212> TYPE: PRT
<213> ORGANISM: Artificial
<220> FEATURE:
<223> OTHER INFORMATION: Peptide_extracellular region

<400> SEQUENCE: 92

Met Glu Ser Ser Gly Asn Pro Glu Ser Thr Thr Phe
1               5                   10

<210> SEQ ID NO 93
<211> LENGTH: 12
<212> TYPE: PRT
<213> ORGANISM: Artificial
<220> FEATURE:
<223> OTHER INFORMATION: Peptide_extracellular region

<400> SEQUENCE: 93

Ser Ser Gly Asn Pro Glu Ser Thr Thr Phe Phe Tyr
1               5                   10

<210> SEQ ID NO 94
<211> LENGTH: 12
<212> TYPE: PRT
<213> ORGANISM: Artificial
<220> FEATURE:
<223> OTHER INFORMATION: Peptide_extracellular region

<400> SEQUENCE: 94

Gly Asn Pro Glu Ser Thr Thr Phe Phe Tyr Tyr Asp
1               5                   10

<210> SEQ ID NO 95
<211> LENGTH: 12
<212> TYPE: PRT
<213> ORGANISM: Artificial
<220> FEATURE:
<223> OTHER INFORMATION: Peptide_extracellular region

<400> SEQUENCE: 95

Pro Glu Ser Thr Thr Phe Phe Tyr Tyr Asp Leu Gln
1               5                   10

<210> SEQ ID NO 96
<211> LENGTH: 12
<212> TYPE: PRT
<213> ORGANISM: Artificial
<220> FEATURE:
<223> OTHER INFORMATION: Peptide_extracellular region

<400> SEQUENCE: 96

Ser Thr Thr Phe Phe Tyr Tyr Asp Leu Gln Ser Gln
1               5                   10

<210> SEQ ID NO 97
<211> LENGTH: 12
<212> TYPE: PRT
<213> ORGANISM: Artificial
<220> FEATURE:
<223> OTHER INFORMATION: Peptide_extracellular region

<400> SEQUENCE: 97

Thr Phe Phe Tyr Tyr Asp Leu Gln Ser Gln Pro Cys
1               5                   10

<210> SEQ ID NO 98
<211> LENGTH: 12
<212> TYPE: PRT
<213> ORGANISM: Artificial
<220> FEATURE:
<223> OTHER INFORMATION: Peptide_extracellular region

<400> SEQUENCE: 98

Phe Tyr Tyr Asp Leu Gln Ser Gln Pro Cys Glu Asn
1               5                   10

<210> SEQ ID NO 99
<211> LENGTH: 12
<212> TYPE: PRT
<213> ORGANISM: Artificial
<220> FEATURE:
<223> OTHER INFORMATION: Peptide_extracellular region

<400> SEQUENCE: 99

```
Tyr Asp Leu Gln Ser Gln Pro Cys Glu Asn Gln Ala
1               5                   10
```

<210> SEQ ID NO 100
<211> LENGTH: 12
<212> TYPE: PRT
<213> ORGANISM: Artificial
<220> FEATURE:
<223> OTHER INFORMATION: Peptide_extracellular region

<400> SEQUENCE: 100

```
Leu Gln Ser Gln Pro Cys Glu Asn Gln Ala Trp Val
1               5                   10
```

<210> SEQ ID NO 101
<211> LENGTH: 12
<212> TYPE: PRT
<213> ORGANISM: Artificial
<220> FEATURE:
<223> OTHER INFORMATION: Peptide_extracellular region

<400> SEQUENCE: 101

```
Ser Gln Pro Cys Glu Asn Gln Ala Trp Val Phe Ala
1               5                   10
```

<210> SEQ ID NO 102
<211> LENGTH: 12
<212> TYPE: PRT
<213> ORGANISM: Artificial
<220> FEATURE:
<223> OTHER INFORMATION: Peptide_extracellular region

<400> SEQUENCE: 102

```
Pro Cys Glu Asn Gln Ala Trp Val Phe Ala Thr Leu
1               5                   10
```

<210> SEQ ID NO 103
<211> LENGTH: 12
<212> TYPE: PRT
<213> ORGANISM: Artificial
<220> FEATURE:
<223> OTHER INFORMATION: Peptide_extracellular region

<400> SEQUENCE: 103

```
Glu Asn Gln Ala Trp Val Phe Ala Thr Leu Ala Thr
1               5                   10
```

<210> SEQ ID NO 104
<211> LENGTH: 12
<212> TYPE: PRT
<213> ORGANISM: Artificial
<220> FEATURE:
<223> OTHER INFORMATION: Peptide_extracellular region

<400> SEQUENCE: 104

```
Gln Ala Trp Val Phe Ala Thr Leu Ala Thr Thr Val
1               5                   10
```

<210> SEQ ID NO 105
<211> LENGTH: 12
<212> TYPE: PRT
<213> ORGANISM: Artificial
<220> FEATURE:
<223> OTHER INFORMATION: Peptide_extracellular region

<400> SEQUENCE: 105

```
Ile Ser Pro Tyr His Trp Gly Trp Val Leu Gly Asp
```

```
                 1               5                   10

<210> SEQ ID NO 106
<211> LENGTH: 12
<212> TYPE: PRT
<213> ORGANISM: Artificial
<220> FEATURE:
<223> OTHER INFORMATION: Peptide_extracellular region

<400> SEQUENCE: 106

Tyr His Trp Gly Trp Val Leu Gly Asp Phe Leu Cys
1               5                   10

<210> SEQ ID NO 107
<211> LENGTH: 12
<212> TYPE: PRT
<213> ORGANISM: Artificial
<220> FEATURE:
<223> OTHER INFORMATION: Peptide_extracellular region

<400> SEQUENCE: 107

Gly Trp Val Leu Gly Asp Phe Leu Cys Lys Leu Leu
1               5                   10

<210> SEQ ID NO 108
<211> LENGTH: 12
<212> TYPE: PRT
<213> ORGANISM: Artificial
<220> FEATURE:
<223> OTHER INFORMATION: Peptide_extracellular region

<400> SEQUENCE: 108

Ile Phe His Lys Val Leu Ser Ser Gly Cys Asp Tyr
1               5                   10

<210> SEQ ID NO 109
<211> LENGTH: 12
<212> TYPE: PRT
<213> ORGANISM: Artificial
<220> FEATURE:
<223> OTHER INFORMATION: Peptide_extracellular region

<400> SEQUENCE: 109

Lys Val Leu Ser Ser Gly Cys Asp Tyr Ser Glu Leu
1               5                   10

<210> SEQ ID NO 110
<211> LENGTH: 12
<212> TYPE: PRT
<213> ORGANISM: Artificial
<220> FEATURE:
<223> OTHER INFORMATION: Peptide_extracellular region

<400> SEQUENCE: 110

Ser Ser Gly Cys Asp Tyr Ser Glu Leu Thr Trp Tyr
1               5                   10

<210> SEQ ID NO 111
<211> LENGTH: 12
<212> TYPE: PRT
<213> ORGANISM: Artificial
<220> FEATURE:
<223> OTHER INFORMATION: Peptide_extracellular region

<400> SEQUENCE: 111

Cys Asp Tyr Ser Glu Leu Thr Trp Tyr Leu Thr Ser
1               5                   10
```

<210> SEQ ID NO 112
<211> LENGTH: 12
<212> TYPE: PRT
<213> ORGANISM: Artificial
<220> FEATURE:
<223> OTHER INFORMATION: Peptide_extracellular region

<400> SEQUENCE: 112

Ser Glu Leu Thr Trp Tyr Leu Thr Ser Val Tyr Gln
1               5                   10

<210> SEQ ID NO 113
<211> LENGTH: 12
<212> TYPE: PRT
<213> ORGANISM: Artificial
<220> FEATURE:
<223> OTHER INFORMATION: Peptide_extracellular region

<400> SEQUENCE: 113

Leu Gln Thr Leu Phe Arg Thr Gln Ile Ile Arg Ser
1               5                   10

<210> SEQ ID NO 114
<211> LENGTH: 12
<212> TYPE: PRT
<213> ORGANISM: Artificial
<220> FEATURE:
<223> OTHER INFORMATION: Peptide_extracellular region

<400> SEQUENCE: 114

Leu Phe Arg Thr Gln Ile Ile Arg Ser Cys Glu Ala
1               5                   10

<210> SEQ ID NO 115
<211> LENGTH: 12
<212> TYPE: PRT
<213> ORGANISM: Artificial
<220> FEATURE:
<223> OTHER INFORMATION: Peptide_extracellular region

<400> SEQUENCE: 115

Thr Gln Ile Ile Arg Ser Cys Glu Ala Lys Gln Gln
1               5                   10

<210> SEQ ID NO 116
<211> LENGTH: 12
<212> TYPE: PRT
<213> ORGANISM: Artificial
<220> FEATURE:
<223> OTHER INFORMATION: Peptide_extracellular region

<400> SEQUENCE: 116

Ile Arg Ser Cys Glu Ala Lys Gln Gln Leu Glu Tyr
1               5                   10

<210> SEQ ID NO 117
<211> LENGTH: 12
<212> TYPE: PRT
<213> ORGANISM: Artificial
<220> FEATURE:
<223> OTHER INFORMATION: Peptide_extracellular region

<400> SEQUENCE: 117

Cys Glu Ala Lys Gln Gln Leu Glu Tyr Ala Leu Leu
1               5                   10

```
<210> SEQ ID NO 118
<211> LENGTH: 24
<212> TYPE: PRT
<213> ORGANISM: Artificial
<220> FEATURE:
<223> OTHER INFORMATION: Candidate epitope

<400> SEQUENCE: 118

Pro Glu Ser Thr Thr Phe Phe Tyr Tyr Asp Leu Gln Ser Gln Pro Cys
1               5                   10                  15

Glu Asn Gln Ala Trp Val Phe Ala
            20

<210> SEQ ID NO 119
<211> LENGTH: 12
<212> TYPE: PRT
<213> ORGANISM: Artificial
<220> FEATURE:
<223> OTHER INFORMATION: Candidate epitope

<400> SEQUENCE: 119

Cys Asp Tyr Ser Glu Leu Thr Trp Tyr Leu Thr Ser
1               5                   10
```